(12) United States Patent  
Edwards et al.

(10) Patent No.: US 9,022,980 B2  
(45) Date of Patent: May 5, 2015

(54) MEDICAL INJECTOR SIMULATION DEVICE

(75) Inventors: Eric S. Edwards, Mosely, VA (US); Evan T. Edwards, Charlottesville, VA (US); Mark J. Licata, Doswell, VA (US); Paul F. Meyers, Fishers, IN (US); T. Spencer Williamson, Richmond, VA (US); Kai R. Worrell, Hopkins, MN (US); David A. Weinzierl, Andover, MN (US)

(73) Assignee: kaleo, Inc., Richmond, VA (US)

( * ) Notice: Subject to any disclaimer, the term of this patent is extended or adjusted under 35 U.S.C. 154(b) by 1795 days.

(21) Appl. No.: 11/679,331

(22) Filed: Feb. 27, 2007

(65) Prior Publication Data

US 2008/0059133 A1 Mar. 6, 2008

(51) Int. Cl.
| | |
|---|---|
| *A61M 37/00* | (2006.01) |
| *G09B 23/28* | (2006.01) |
| *G06Q 10/00* | (2012.01) |
| *A61M 5/19* | (2006.01) |
| *A61M 5/20* | (2006.01) |
| *A61M 5/24* | (2006.01) |

(52) U.S. Cl.
CPC ............. *G09B 23/285* (2013.01); *A61M 5/19* (2013.01); *A61M 5/2053* (2013.01); *A61M 5/24* (2013.01); *G06Q 10/00* (2013.01)

(58) Field of Classification Search
CPC .. G09B 23/285; A61M 5/20; A61M 2205/18; A61M 2205/183; A61M 2205/186; A61M 2205/43; A61M 2205/44; A61M 2205/50; A61M 2205/502; A61M 2205/505; A61M 2205/6018

USPC .............. 604/65–67, 503–505, 890.1–892.1, 604/137; 434/262

See application file for complete search history.

(56) References Cited

U.S. PATENT DOCUMENTS

| | | | |
|---|---|---|---|
| 2,960,087 | A | 11/1960 | Uytenbogaart |
| 3,055,362 | A | 9/1962 | Uytenbogaart |
| 3,115,133 | A | 12/1963 | Morando |
| 3,426,448 | A | 2/1969 | Sarnoff |
| 3,688,765 | A | 9/1972 | Gasaway |
| 3,768,472 | A | 10/1973 | Hodosh et al. |
| 3,795,061 | A | 3/1974 | Sarnoff et al. |
| 3,945,379 | A | 3/1976 | Pritz et al. |
| 4,108,177 | A | 8/1978 | Pistor |
| 4,360,019 | A | 11/1982 | Portner et al. |
| 4,424,057 | A | 1/1984 | House |
| 4,441,629 | A | 4/1984 | Mackal |

(Continued)

FOREIGN PATENT DOCUMENTS

| | | |
|---|---|---|
| AU | 2004231230 | 6/2006 |
| EP | 1043037 A2 | 10/2000 |

(Continued)

OTHER PUBLICATIONS

Combined Search and Examination Report for GB 0818178.6, mailed Dec. 1, 2008.

(Continued)

*Primary Examiner* — Nathan R Price  
(74) *Attorney, Agent, or Firm* — Cooley LLP

(57) ABSTRACT

An apparatus includes a simulated medicament delivery device and an electronic circuit system coupled to the simulated medicament delivery device. The electronic circuit system is configured to output an electronic output associated with a use of the simulated medicament delivery device.

31 Claims, 33 Drawing Sheets

(56) References Cited

U.S. PATENT DOCUMENTS

| | | |
|---|---|---|
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,865,582 A | 9/1989 | Sibalis |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,244,465 A | 9/1993 | Michel |
| 5,271,527 A | 12/1993 | Haber et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,399,163 A | 3/1995 | Peterson et al. |
| 5,405,362 A | 4/1995 | Kramer et al. |
| 5,417,660 A | 5/1995 | Martin |
| 5,466,217 A | 11/1995 | Myers et al. |
| 5,514,135 A | 5/1996 | Earle |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,740,794 A | 4/1998 | Smith et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,346 A | 10/1998 | Weiner |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,249,717 B1 | 6/2001 | Nicholson et al. |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,312,412 B1 | 11/2001 | Saied et al. |
| 6,317,630 B1 | 11/2001 | Gross et al. |
| 6,321,654 B1 | 11/2001 | Robinson |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,411,567 B1 | 6/2002 | Niemiec et al. |
| 6,413,236 B1 | 7/2002 | Van Dyke |
| 6,425,897 B2 | 7/2002 | Overes et al. |

(56) References Cited

U.S. PATENT DOCUMENTS

| | | |
|---|---|---|
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,478,771 B1 | 11/2002 | Lavi et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,633,796 B1 | 10/2003 | Pool et al. |
| 6,641,566 B2 | 11/2003 | Douglas et al. |
| 6,645,181 B1 | 11/2003 | Lavi et al. |
| 6,648,850 B2 | 11/2003 | Landau |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,963,280 B2 | 11/2005 | Eskildsen |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,093,595 B2 | 8/2006 | Nesbitt |
| 7,104,972 B2 | 9/2006 | Moller et al. |
| 7,113,101 B2 | 9/2006 | Peterson et al. |
| 7,116,233 B2 | 10/2006 | Zhurin |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,351,223 B2 | 4/2008 | Call |
| 7,635,348 B2 | 12/2009 | Raven et al. |
| 7,682,155 B2 | 3/2010 | Raven et al. |
| 7,850,662 B2 | 12/2010 | Veasey et al. |
| 7,871,393 B2 | 1/2011 | Monroe |
| 7,918,832 B2 | 4/2011 | Veasey et al. |
| 7,938,802 B2 | 5/2011 | Bicknell et al. |
| 8,544,645 B2 | 10/2013 | Edwards et al. |
| 8,622,973 B2 | 1/2014 | Edwards et al. |
| 8,899,987 B2 | 12/2014 | Edwards et al. |
| 8,926,594 B2 | 1/2015 | Edwards et al. |
| 2001/0005781 A1 | 6/2001 | Bergens et al. |
| 2002/0016567 A1* | 2/2002 | Hochman et al. ............ 604/131 |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1* | 7/2002 | Juselius ........................ 222/631 |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0100862 A1 | 5/2003 | Edwards et al. |
| 2003/0106824 A1 | 6/2003 | Wilmot et al. |
| 2003/0130853 A1 | 7/2003 | Maire |
| 2003/0132128 A1 | 7/2003 | Mazur |
| 2003/0135388 A1 | 7/2003 | Martucci et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0069667 A1 | 4/2004 | Tomellini et al. |
| 2004/0078001 A1 | 4/2004 | Langley et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1* | 10/2004 | Atterbury et al. ............ 604/224 |
| 2004/0220524 A1 | 11/2004 | Sadowski et al. |
| 2004/0225255 A1 | 11/2004 | Ono |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0090782 A1 | 4/2005 | Marshall et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |

(56) References Cited

U.S. PATENT DOCUMENTS

| | | |
|---|---|---|
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0186221 A1 | 8/2005 | Reynolds et al. |
| 2005/0197654 A1 | 9/2005 | Edman et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0074519 A1 | 4/2006 | Barker et al. |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0247578 A1 | 11/2006 | Arguendas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0049998 A1* | 3/2007 | Conrad et al. .................. 607/96 |
| 2007/0074722 A1 | 4/2007 | Giroux et al. |
| 2007/0088268 A1 | 4/2007 | Edwards et al. |
| 2007/0100288 A1 | 5/2007 | Bozeman et al. |
| 2007/0111175 A1 | 5/2007 | Raven et al. |
| 2007/0129708 A1 | 6/2007 | Edwards et al. |
| 2007/0149925 A1 | 6/2007 | Edwards et al. |
| 2007/0184847 A1 | 8/2007 | Hansen et al. |
| 2007/0203247 A1 | 8/2007 | Phillips et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0239114 A1 | 10/2007 | Edwards et al. |
| 2007/0239116 A1 | 10/2007 | Follman et al. |
| 2007/0260210 A1 | 11/2007 | Conroy |
| 2008/0033393 A1 | 2/2008 | Edwards et al. |
| 2008/0058719 A1 | 3/2008 | Edwards et al. |
| 2008/0103490 A1 | 5/2008 | Edwards et al. |
| 2008/0111685 A1 | 5/2008 | Olson et al. |
| 2008/0160492 A1 | 7/2008 | Campbell et al. |
| 2008/0230057 A1 | 9/2008 | Sutherland |
| 2008/0249468 A1 | 10/2008 | Edwards et al. |
| 2008/0269689 A1 | 10/2008 | Edwards et al. |
| 2008/0298188 A1 | 12/2008 | Edwards et al. |
| 2009/0024112 A1 | 1/2009 | Edwards et al. |
| 2009/0030285 A1 | 1/2009 | Andersen |
| 2009/0062728 A1 | 3/2009 | Woo |
| 2009/0143761 A1 | 6/2009 | Cantor et al. |
| 2010/0022963 A1 | 1/2010 | Edwards et al. |
| 2010/0211005 A1 | 8/2010 | Edwards et al. |
| 2010/0309012 A1 | 12/2010 | Edwards et al. |
| 2010/0318035 A1 | 12/2010 | Edwards et al. |
| 2012/0015335 A1 | 1/2012 | Smith et al. |
| 2012/0046613 A1 | 2/2012 | Plumptre |
| 2012/0107783 A1 | 5/2012 | Julian et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2013/0110050 A1 | 5/2013 | Boyd et al. |
| 2013/0184649 A1 | 7/2013 | Edwards et al. |
| 2013/0190692 A1 | 7/2013 | Edwards et al. |
| 2013/0266919 A1 | 10/2013 | Baker et al. |
| 2013/0280687 A1 | 10/2013 | Edwards et al. |
| 2014/0309616 A1 | 10/2014 | Edwards et al. |
| 2014/0371714 A1 | 12/2014 | Edwards et al. |

FOREIGN PATENT DOCUMENTS

| | | |
|---|---|---|
| EP | 1287840 A1 | 5/2003 |
| EP | 1462134 A1 | 9/2004 |
| EP | 1 712 178 A2 | 10/2006 |
| MX | PA04009276 | 1/2005 |
| WO | WO 91/04760 A1 | 4/1991 |
| WO | WO 93/02720 | 2/1993 |
| WO | WO 95/26009 | 9/1995 |
| WO | WO 96/25965 | 8/1996 |
| WO | WO 97/30742 | 8/1997 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 01/24690 A2 | 4/2001 |
| WO | WO 01/26020 A1 | 4/2001 |
| WO | WO 01/41849 A3 | 6/2001 |
| WO | WO 01/88828 | 11/2001 |
| WO | WO 01/93926 A2 | 12/2001 |
| WO | WO 02/24257 A1 | 3/2002 |
| WO | WO 02/051471 A1 | 7/2002 |
| WO | WO 03/057283 A1 | 7/2003 |
| WO | WO 03/095001 A1 | 11/2003 |
| WO | WO 03/097133 A1 | 11/2003 |
| WO | WO 2004/041330 A2 | 5/2004 |
| WO | WO 2005/050526 A2 | 6/2005 |
| WO | WO 2006/045525 A1 | 5/2006 |
| WO | WO 2006/109778 A1 | 10/2006 |
| WO | WO 2006/123956 | 11/2006 |
| WO | WO 2006/125692 A1 | 11/2006 |
| WO | WO 2008/005315 | 1/2008 |
| WO | WO 2008/148864 | 12/2008 |
| WO | WO 2010/114392 | 10/2010 |
| WO | WO 2013/043063 | 3/2013 |

OTHER PUBLICATIONS

Office Action for U.S. Appl. No. 11/621,236, mailed Feb. 3, 2009.
Examination Report for GB 0818178.6, mailed Mar. 23, 2009.
Examination Report for GB 0905194.7, mailed May 8, 2009.
Final Office Action for U.S. Appl. No. 11/621,236, mailed Jul. 1, 2009.
Examination Report for GB 0818178.6, mailed Jul. 9, 2009.
International Search Report and Written Opinion for International Patent Application No. PCT/US07/007626 mailed Sep. 29, 2008.
"Solutions for Medical Devices," 3M Brochure, © 3M 2006 80-6201-3490-0.
Merle Tingelstad, "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&Article ID=CA6332947>.
"Flexible circuits / Flex circuits / Flexible Technology Ltd.," Flexible Technology Limited [online] [retrieved on Aug. 28, 2006] Retrieved from the Internet <URL: http://www.flexibletechnology.com/>.
"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible_circuits_Capability.htm>.
"Flex Circuits/flexible circuits design guide," [online] [retrieved on Aug. 28, 2006] Retrieved from the Internet <URL: http://flexiblecircuit.co.uk/Flex_Circuits_Design_Guide.htm>.
"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto_Injector_Pouches.html>.
"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/productcatalogue.asp>.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1>.

(56) References Cited

OTHER PUBLICATIONS

Roger Allan, "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart_labels_in.html>.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8.

Dr. Oliver Scholz, "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true.

Heartsine Technology, samaritan™ PAD Accessories [online] [retrieved on Jun. 1, 2007] Retrieved from the Internet <URL: http://www.heartsine.com/aboutsam-accessories.htm>.

CliniSense Corporation, "Drug delivery devices A potentially harsh environment for drugs," Stability [online] [retrieved on Jun. 1, 2007] Retrieved from the Internet <URL: http://www.clinisense.com/devices.htm>.

CliniSense Corporation, "LifeTrack Technology A new method to detect improper storage." Stability [online] [retrieved on Jun. 1, 2007] Retrieved from the Internet <URL: http://www.clinisense.com/tech.htm>.

AED Professionals™ Brochure [online] [retrieved on Jun. 1, 2007] Retrieved from the Internet <URL: http://www.aedprofessionals.com/>.

Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8>.

Search Report and Written Opinion for International Patent Application No. PCT/US07/007626 mailed Sep. 29, 2008.

Search Report and Written Opinion for International Patent Application No. PCT/US09/63983, mailed Feb. 25, 2010.

Search Report for European Patent Application No. EP 09150135.3, mailed Mar. 15, 2010.

Office Action for Israel Patent Application No. 184552, mailed Jul. 28, 2011.

Final Office Action for U.S. Appl. No. 11/671,025, mailed Sep. 8, 2011.

Office Action for U.S. Appl. No. 12/794,020, mailed Oct. 25, 2011.

Office Action for U.S. Appl. No. 12/119,016, mailed Nov. 3, 2011.

Office Action for U.S. Appl. No. 12/017,405, mailed Dec. 7, 2011.

Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamcl_trainer.html/>.

Laura Lin Gosbee, "Nuts! I Can't Figure Out How to Use My Life-Saving Epinephrine Auto-Injector," Joint Commision Journal on Quality and Safety, vol. 30, No. 4, Apr. 2004.

Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>.

Office Action for Japanese Patent Application No. JP2007-553358, mailed Mar. 17, 2011.

Search and Examination Report for British Patent Application No. 1104754.5, mailed May 20, 2011.

Office Action for Japanese Patent Application No. JP2009-502964, mailed May 23, 2011.

Search and Examination Report for British Patent Application No. 1108993.5, mailed Jun. 17, 2011.

Office Action for Japanese Patent Application No. 2009-502964, mailed May 21, 2012.

Office Action for Japanese Patent Application No. 2011-509613, mailed Mar. 26, 2014.

Office Action for U.S. Appl. No. 13/962,336, mailed Nov. 20, 2013.

Office Action for U.S. Appl. No. 13/962,336, mailed May 27, 2014.

Non-Final Office Action for U.S. Appl. No. 13/234,649, mailed May 28, 2013.

\* cited by examiner

MEDICAL INJECTOR SIMULATION DEVICE

CROSS-REFERENCE TO RELATED APPLICATIONS

This application is related to U.S. patent application Ser. No. 11/671,025 (now U.S. Pat. No. 8,172,082), entitled "Devices, Systems and Methods for Medicament Delivery," filed Feb. 5, 2007, which is a continuation-in-part of U.S. patent application Ser. No. 11/621,236 (now U.S. Pat. No. 7,731,686), entitled "Devices, Systems and Methods for Medicament Delivery," filed Jan. 9, 2007, which is a continuation-in-part of U.S. patent application Ser. No. 10/572,148 (now U.S. Pat. No. 7,749,194), entitled "Devices, Systems and Methods for Medicament Delivery," filed Mar. 16, 2006, which is a national stage filing under 35 U.S.C. §371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005, each of which is incorporated herein by reference in its entirety. This application claims priority to U.S. Provisional Application Ser. No. 60/787,046, entitled "Devices, Systems and Methods for Medicament Delivery," filed Mar. 29, 2006, which is incorporated herein by reference in its entirety.

BACKGROUND

The invention relates generally to a medical device, and more particularly to a simulated medicament delivery device.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, an auto-injector, to rapidly self-administer a medicament in response to an allergic reaction.

To actuate such a medicament delivery device, however, the user may be required to execute a series of operations. For example, to actuate some known auto-injectors, the user must remove a protective cap, remove a locking device, place the auto-injector in a proper position against the body and then press a button to actuate the auto-injector. Failure to complete these operations properly can result in an incomplete injection and/or injection into an undesired location of the body. In certain instances, for example, users who have become confused in the operation of some known auto-injectors have inadvertently injected the medicament into their thumb by improperly positioning the auto-injector.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, and may therefore have no experience with the medicament delivery device. Similarly, because some known medicament delivery devices are configured to be used relatively infrequently in response to an allergic reaction or the like, even those users familiar with the device and/or who have been trained may not be well practiced at operating the device. Finally, such devices are often used during an emergency situation, during which even experienced and/or trained users may be subject to confusion, panic and/or the physiological effects of the condition requiring treatment.

Some known medicament delivery devices include printed instructions to inform the user of the steps required to properly deliver the medicament. Such printed instructions, however, can be inadequate for the class of users and/or the situations described above. Moreover, because some known medicament delivery devices, such as, for example, auto-injectors, pen injectors, inhalers or the like, can be compact, such printed instructions may be too small to read and comprehend during an emergency situation.

Some known medicament delivery devices are associated with simulated medicament delivery devices (e.g., "trainers") to provide a method for users to practice using the medicament delivery device without being exposed to the medicament or needles typically contained therein. Such simulated medicament delivery devices, however, can also include inadequate use instructions as described above. Moreover, some known simulated medicament delivery devices can be difficult to reset for subsequent use.

Thus, a need exists for a simulated medicament delivery device that provides instructions that can be easily understood by an untrained user in any type of situation. Additionally, a need exists for a simulated medicament delivery device that can be easily reset for subsequent use.

SUMMARY

Medicament delivery devices are described herein. In some embodiments, an apparatus includes a simulated medicament delivery device and an electronic circuit system coupled to the simulated medicament delivery device. The electronic circuit system is configured to output an electronic output associated with a use of the simulated medicament delivery device.

DETAILED DESCRIPTION

Figure 1:
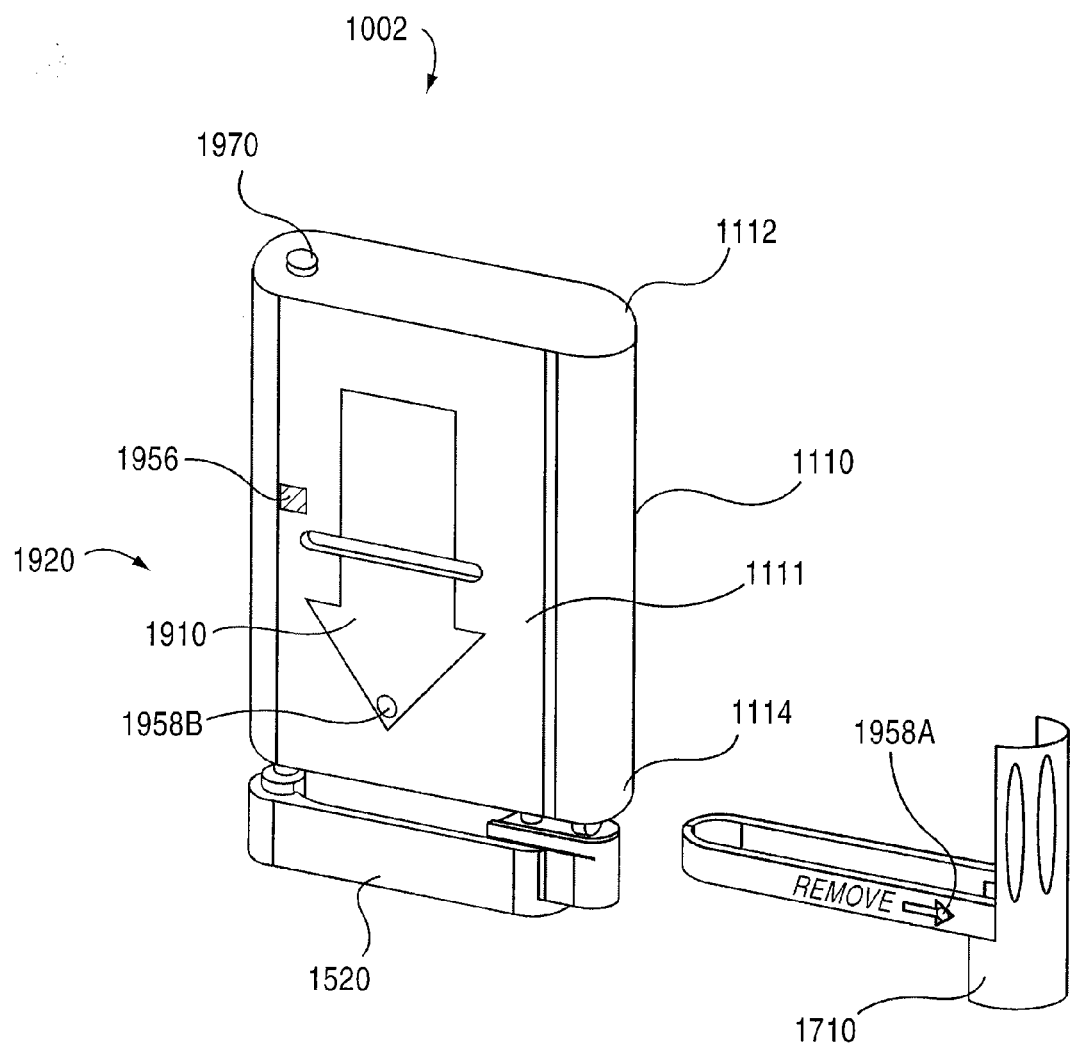
FIG. 1 is a perspective view of a medicament delivery device according to an embodiment of the invention.

In some embodiments, an apparatus includes a label configured to be coupled to a medicament delivery device and/or a simulated medicament delivery device. The label includes a first surface and a second surface. The first surface is configured to be coupled to an outer surface of the medicament delivery device and/or the simulated medicament delivery device. In some embodiments, for example, the first surface can include an adhesive. The second surface includes a textual indicia, such as, for example, a description of the medicament delivery device, a mark indicating the manufacturer or distributor of the medicament delivery device and/or an instruction associated with the use of the medicament delivery device. The label further includes an electronic circuit system configured to output an electronic signal. In some embodiments, the electronic signal can include an instruction associated with the use of the medicament delivery device and/or the simulated medicament delivery device.

In some embodiments, an apparatus includes a printed circuit board configured to be coupled to a medicament delivery device and/or a simulated medicament delivery device. The printed circuit board includes a substrate and an electrical conductor disposed on the substrate. The substrate includes an actuation portion configured to receive an actuator. The actuator is configured to deform the actuation portion of the substrate, thereby separating the electrical conductor.

In some embodiments, an apparatus includes a printed circuit board configured to be coupled to a medicament delivery device and/or a simulated medicament delivery device. The printed circuit board includes a substrate and an electrical conductor disposed on the substrate. The substrate includes an actuation portion configured to receive an actuator. The actuation portion of the substrate defines an opening adjacent the electrical conductor, the opening being configured to receive the actuator. The actuator is configured to move substantially parallel to a plane defined by a surface of the actuation portion of the substrate to produce a tear in the actuation portion of the substrate, thereby severing the electrical conductor. In some embodiments, the opening can be configured to propagate the tear in a predetermined direction.

In some embodiments, an apparatus includes a medicament delivery device configured to deliver a medicament into a body. The medicament delivery device, which can be, for example, a pen injector, an auto-injector, an inhaler or a transdermal delivery device, includes an electronic circuit system and a locking member. The electronic circuit system is configured to output an electronic signal associated with a use of the medicament delivery device. In some embodiments, the electronic signal can be, for example, associated with recorded speech. The locking member is configured to prevent the medicament from being delivered into the body. The locking member includes an actuator configured to actuate the electronic circuit system.

In some embodiments, an apparatus includes a medicament delivery device configured to deliver a medicament into a body. The medicament delivery device includes an electronic circuit system and a locking member. The electronic circuit system includes a switch and is configured to output a signal when the switch is moved from a first state to a second state. The locking member is configured to prevent the medicament from being delivered into the body when in a first position and to allow the medicament to be delivered into the body when in a second position. A portion of the locking member is configured to move the switch from the first state to the second state when the locking member is moved from the first position to the second position.

In some embodiments, an apparatus includes a housing configured to contain a medicament, a flexible printed circuit board, an energy storage member and a label. The flexible printed circuit board is disposed on an outer surface of the housing and includes a first electrical contact portion and a second electrical contact portion. The label is coupled to the flexible printed circuit board and the housing and is configured to maintain a first surface of the energy storage member in electrical communication with the first electrical contact portion and maintain a second surface of the energy storage member in electrical communication with the second electrical contact portion. The energy storage member, can be, for example, a battery.

In some embodiments, a method includes assembling a medicament delivery device and/or a simulated medicament delivery device, such as, for example, an auto-injector or an auto-injector simulator. An electronic circuit system is then placed against an outer surface of the medicament delivery device and/or the simulated medicament delivery device. A label is then coupled to the medicament delivery device and/or the simulated medicament delivery device such that the label is disposed about a portion of the electronic circuit system.

In some embodiments, an apparatus includes a container defining an internal region configured to contain multiple medicament delivery devices, such as, for example, pen injectors, auto-injectors, inhalers or the like. The container includes an electronic circuit system configured to output a first electronic output associated with a first medicament delivery device contained within the internal region when the first medicament delivery device is removed from the internal region of the container. The electronic circuit system is further configured to output a second electronic output associated with a second medicament delivery device contained within the internal region when the second medicament delivery device is removed from the internal region of the container. The second electronic output is different than the first electronic output. At least one of the first electronic output or the second electronic output is associated with a use instruction of the first medicament delivery device and/or the second medicament delivery device.

In some embodiments, an apparatus includes a container defining an internal region configured to contain multiple medicament delivery devices. The container includes an electronic circuit system configured to output a first electronic output associated with a first medicament delivery device contained within the internal region when the first medicament delivery device is removed from the internal region of the container. The first medicament delivery device includes a label configured to output a signal associated with at least one of a contents of the first medicament delivery device, an expiration date of the first medicament delivery device, a dosage of the first medicament delivery device or a use instruction associated with the first medicament delivery device. In this manner, the first electronic output can be associated with the signal received by the electronic circuit system. The electronic circuit system is further configured to output a second electronic output associated with a second medicament delivery device contained within the internal region when the second medicament delivery device is removed from the internal region of the container. The second electronic output is different than the first electronic output. At least one of the first electronic output or the second electronic output is associated with a use instruction of the first medicament delivery device and/or the second medicament delivery device.

In some embodiments, a kit includes a medicament delivery device and a container. The container defines an internal region configured to contain the medicament delivery device. The container includes a movable portion, an electronic circuit system, a first switch and a second switch. The movable portion has a first position, in which the movable portion covers the internal region of the container, and a second position, in which the internal region of the container is exposed to an area outside the container. The first switch is configured to move between a first state and a second state when the movable portion moves between its first position and its second position. The first switch is operatively coupled to the electronic circuit system such that the electronic circuit system is configured to output a first electronic output when the first switch is moved from its first state to its second state. The first electronic output can be, for example, a visual output, an audible output or a haptic output. The second switch is configured to move between a first state and a second state when the medicament delivery device is removed from the internal region of the container. The second switch is operatively coupled to the electronic circuit system such that the electronic circuit system is configured to output a second electronic output when the second switch is moved from its first state to its second state. The second electronic output, which includes an instruction for using the medicament delivery device, can be, for example, a visual output (e.g. a video showing the proper use of the medicament delivery device), an audible output (e.g., a voice recording providing instructions for use) or a haptic output (e.g., a vibration indicating the location of a particular item).

In some embodiments, an apparatus includes a container, a retainer and an electronic circuit system. The container defines an internal region configured to contain at least a portion of a medicament delivery device, such as, for example a pen injector. The retainer is configured to be movably coupled to the container and to retain the portion of the medicament delivery device within the internal region defined by the container. The electronic circuit system is configured to output a first electronic output when the retainer is moved relative to the container and a second electronic output when the medicament delivery device is removed from the internal region. At least one of the first electronic output or the second electronic output is associated with an instruction for using the medicament delivery device.

In some embodiments, an apparatus includes a container, a retainer, an electronic circuit system and a label. The container defines an internal region configured to contain at least a portion of a medicament delivery device, such as, for example a pen injector. The retainer is configured to be movably coupled to the container and to retain the portion of the medicament delivery device within the internal region defined by the container. The label is configured to be coupled to the medicament delivery device and contain information associated with the medicament delivery device in a machine-readable format. The electronic circuit system is configured to output a first electronic output when the retainer is moved relative to the container and a second electronic output when the medicament delivery device is removed from the internal region. The electronic circuit system is further configured to receive the information contained on the label include at least a portion of the information in the first electronic output and/or the second electronic output. At least one of the first electronic output or the second electronic output is associated with an instruction for using the medicament delivery device.

In some embodiments, an apparatus includes a simulated medicament delivery device and an electronic circuit system coupled to the simulated medicament delivery device. The simulated medicament delivery device can be configured, for example, to simulate the look, feel and/or functionality associated with a pen injector, an auto-injector, an inhaler and/or a transdermal delivery device. The electronic circuit system is configured to output an electronic output associated with a use of the simulated medicament delivery device. The electronic output can include, for example, a signal associated with a visual output, an audible output, a haptic output, an olfactory output and/or a taste output. Moreover, the electronic output can include, for example, an instruction for using the simulated medicament delivery device and/or a medicament delivery device.

In some embodiments, an apparatus includes a housing associated with a medicament delivery device and an electronic circuit system. The electronic circuit system is coupled to the housing. The housing and the electronic circuit system are configured to cooperatively simulate the medicament delivery device. The electronic circuit system is configured to output an electronic output to simulate a tactile sensation, an audible sensation, a visual sensation, an olfactory sensation and/or a taste sensation associated with a use of the medicament delivery device.

In some embodiments, a kit includes a medicament delivery device and a simulated medicament delivery device. The simulated medicament delivery device includes an electronic circuit system configured to output an electronic output associated with a use of the simulated medicament delivery device and/or the medicament delivery device.

In some embodiments, a kit includes a medicament delivery device, a simulated medicament delivery device and a container. The container is configured to contain the medicament delivery device and the simulated medicament delivery device. The simulated medicament delivery device includes an electronic circuit system configured to output a first electronic output associated with a use of at least one of the simulated medicament delivery device or the medicament delivery device. The container includes an electronic circuit system. The electronic circuit system of the container and the electronic circuit system of the simulated medicament delivery device are configured to cooperatively output a second electronic output associated with a use of at least one of the simulated medicament delivery device or the medicament delivery device.

In some embodiments, an apparatus includes a label configured to be coupled to a simulated medicament delivery device. The label includes a first surface, a second surface and an electronic circuit system. The first surface is configured to be coupled to a housing of the simulated medicament delivery device. The second surface includes a textual indicia. The electronic circuit system configured to output an electronic signal.

Figure 2:
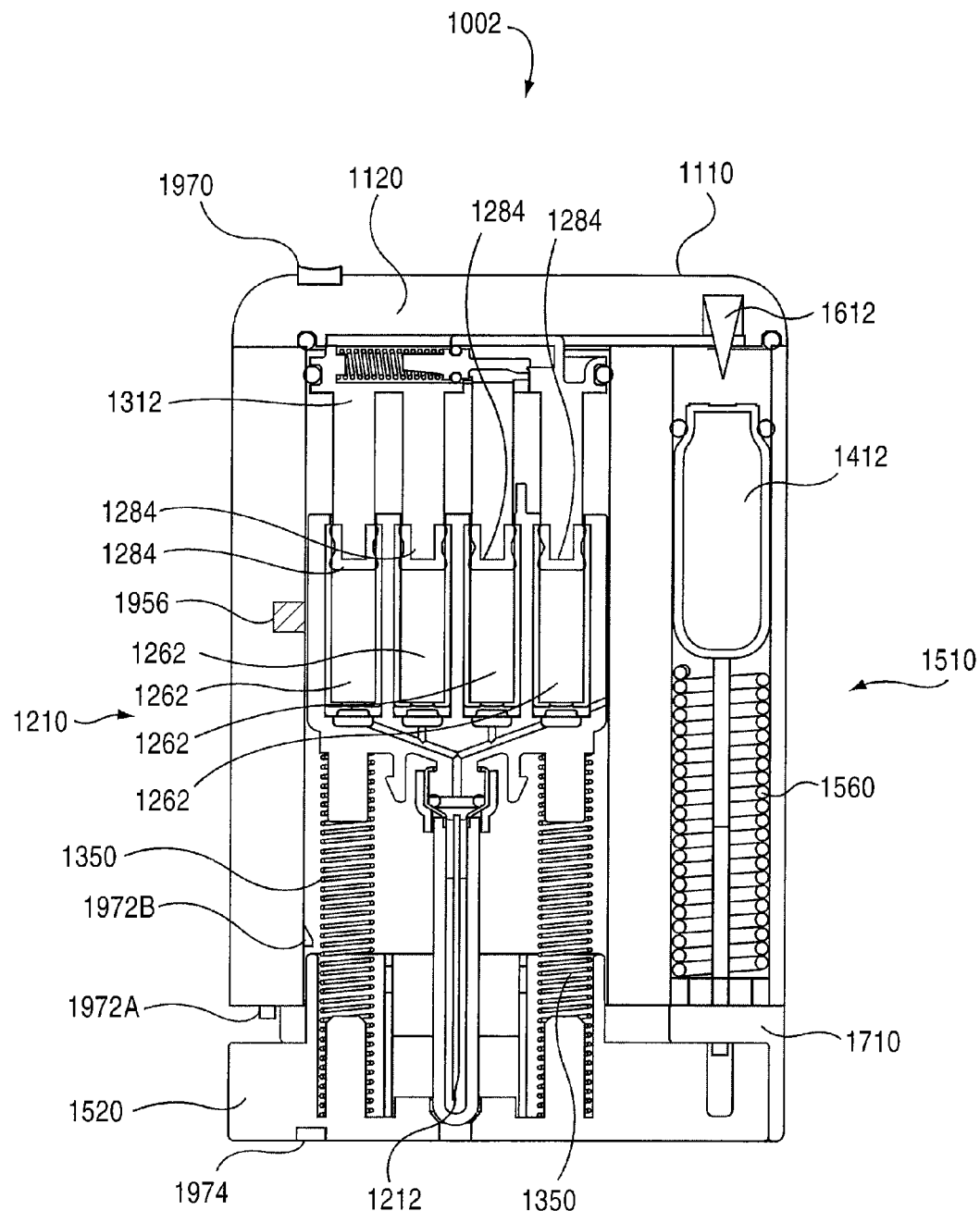
FIG. 2 is a front cross-sectional view of the medicament delivery device shown in FIG. 1.

FIGS. 1 and 2 are a perspective view and a partial cutaway front view, respectively, of an auto-injector 1002 according to an embodiment of the invention. The auto-injector 1002 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, only an overview of the mechanical components and related operation of the auto-injector 1002 is included below.

The auto-injector 1002 includes a housing 1110 that defines a gas chamber 1120. The housing 1110 has a proximal end portion 1112 and a distal end portion 1114. A base 1520 is movably coupled to the distal end portion 1114 of the housing 1110. A safety lock 1710 is removably coupled to the base 1520. As discussed in more detail herein, when the safety lock 1710 is coupled to the base 1520, the auto-injector 1002 cannot be actuated. When the safety lock 1710 is removed from the base 1520, the base 1520 can be moved relative to the housing 1110, thereby actuating the auto-injector 1002. Accordingly, to inject a medicament into the body, the distal end portion 1114 of the housing 1110 is oriented towards the user such that the base 1520 is in contact with the portion of the body where the injection is to be made. The base 1520 is then moved towards the proximal end 1112 of the housing 1110 to actuate the auto-injector 1002.

The auto-injector 1002 includes a medicament injector 1210 and a system actuator 1510 disposed non-coaxially within the housing 1110. The medicament injector 1210 includes multiple medicament vials 1262, a plunger 1284 movably disposed within each medicament vial 1262, a movable member 1312 engaged with each plunger 1284 and a needle 1212. Retraction springs 1350 located within a portion of the base 1520 and the housing 1110 can push the needle 1212 back within the housing 1110 after injection. The system actuator 1510 includes a compressed spring 1560, a compressed gas cylinder 1412, and a puncturing mechanism 1612 to dispel the contents of the compressed gas cylinder 1412.

In use, when the auto-injector 1002 is actuated, the puncturing mechanism 1612 punctures the compressed gas cylinder 1412 allowing a pressurized gas to flow into the gas chamber 1120. In response to a force produced by the pressurized gas on the movable member 1312, the movable member 1312 moves distally within the housing 1110. As a result, the needle 1212 is extended through the housing 1110. The movement of the movable member 1312 also causes the plungers 1284 to move within the vials 1262, thereby expelling a medicament from the vials 1262.

The auto-injector 1002 includes an electronic circuit system 1920 to provide a predetermined sequence of electronic outputs during the use of the auto-injector 1002. The electronic circuit system 1920 is powered by a battery (not shown in FIGS. 1 and 2) and includes a processor (not shown in FIGS. 1 and 2), a start button 1970, two switches 1972A and 1972B, a proximity sensor 1974, two visual output devices 1958A and 1958B and an audio output device 1956. The components of the electronic circuit system 1920 are operatively coupled by any suitable mechanism, such as, for example, a printed circuit board (not shown in FIGS. 1 and 2) having conductive traces.

The start button 1970 is disposed on the proximal end of the housing 1110 and can be manually actuated by the user to begin the sequence of electronic outputs. The first switch 1972A is disposed on the distal portion 1114 of the housing 1110 adjacent the base 1520 and the locking member 1710. The locking member 1710 is configured to engage the first switch 1972A such that when the locking member 1710 is removed, as shown in FIG. 1, the first switch 1972A changes states. In this manner, removal of the locking member 1710 can trigger the processor to output a predetermined electronic output.

Similarly, the second switch 1972B is disposed on the housing 1110 adjacent the medicament injector 1210. The medicament injector 1210 is configured to engage the second switch 1972B such that when the medicament injector 1210 is moved distally within the housing 1110 the second switch 1972B changes states. In this manner, the processor can be prompted to output a predetermined electronic output based on the position of the medicament injector 1210.

The proximity sensor 1974 is disposed on the base 1520 and is configured to produce an output when the base 1520 engages the body. The proximity sensor can be, for example, a temperature sensor, an optical sensor or the like. In this manner, the processor can be prompted to output a predetermined electronic output when the base 1520 is positioned against the body.

The first visual output device 1958A is disposed on the locking member 1710. Similarly, the second visual output device 1958B is disposed on the outer surface 1111 of the housing 1110. The visual output devices 1958A and 1958B are in electronic communication with the processor and are configured to produce an output in response to an electronic signal output by the processor. The visual output devices 1958A and 1958B can be any suitable visual indicia, such as, light-emitting diodes (LEDs), liquid-crystal display (LCD) screens, optical polymers, fiber optic components or the like. In some embodiments, the visual output devices 1958A and 1958B can be coupled to the housing 1110 and/or the locking member 1710 by a label 1910.

The audio output device 1956 is disposed within the housing 1110 such that it can project sound outside of the housing 1110. The audio output device 1956 can be any suitable device for producing sound, such as a micro-speaker a piezoelectric transducer or the like. Such sound output can include, for example, an alarm, a series of beeps, recorded speech or the like. The audio output device 1956 is in electronic communication with the processor and is configured to produce an output in response to an electronic signal output by the processor.

In use, the user activates the electronic circuit system by pushing the start button 1970 to activate the processor, thereby causing the processor to output a predetermined sequence of electronic outputs. In some embodiments, the start button 1970 can activate the processor by providing an input to the processor. In other embodiments, the start button 1970 can activate the processor by placing the battery (not shown in FIGS. 1 and 2) in electronic communication with the processor.

In some embodiments, upon activation, the processor can output an electronic signal to the audio output device 1956 thereby producing a first electronic output instructing the user in how to use the auto-injector 1002. Such a message can state, for example, "please remove the safety tab." Additionally, the first visual output device 1958A can produce a flashing light to further indicate to the user where the locking member 1710 is located. The processor can be configured to repeat the first audible instruction if the locking member 1710 is not removed within a predetermined time period.

When the user removes the locking member 1710, the first switch 1972A changes states thereby triggering the processor to output an electronic output providing a second instruction to the user. The second instruction can be, for example, an audible speech output instructing the user to "please place the base of the device on the outer portion of your thigh." The first visual output device 1958A can produce a lighted output during this audible instruction, thereby visually indicating where the base 1520 is located and/or what portion of the base 1520 should be placed on the thigh.

When the user places the base 1520 against the body, the proximity sensor 1974 provides an input to the processor, thereby triggering the processor to output an electronic output providing a third instruction to the user. The third instruction can be, for example, an audible speech output instructing the user to "push down on the top of the device to activate the injector."

When the injection is completed, the medicament injector 1210 is configured to engage the second switch 1972B, thereby triggering the processor to output an electronic output providing a fourth instruction to the user. Such a post-use instruction can be, for example, an audible speech output instructing the user to seek further medical attention, providing instructions for the safe disposal of the auto-injector 1002 or the like.

Figure 3:
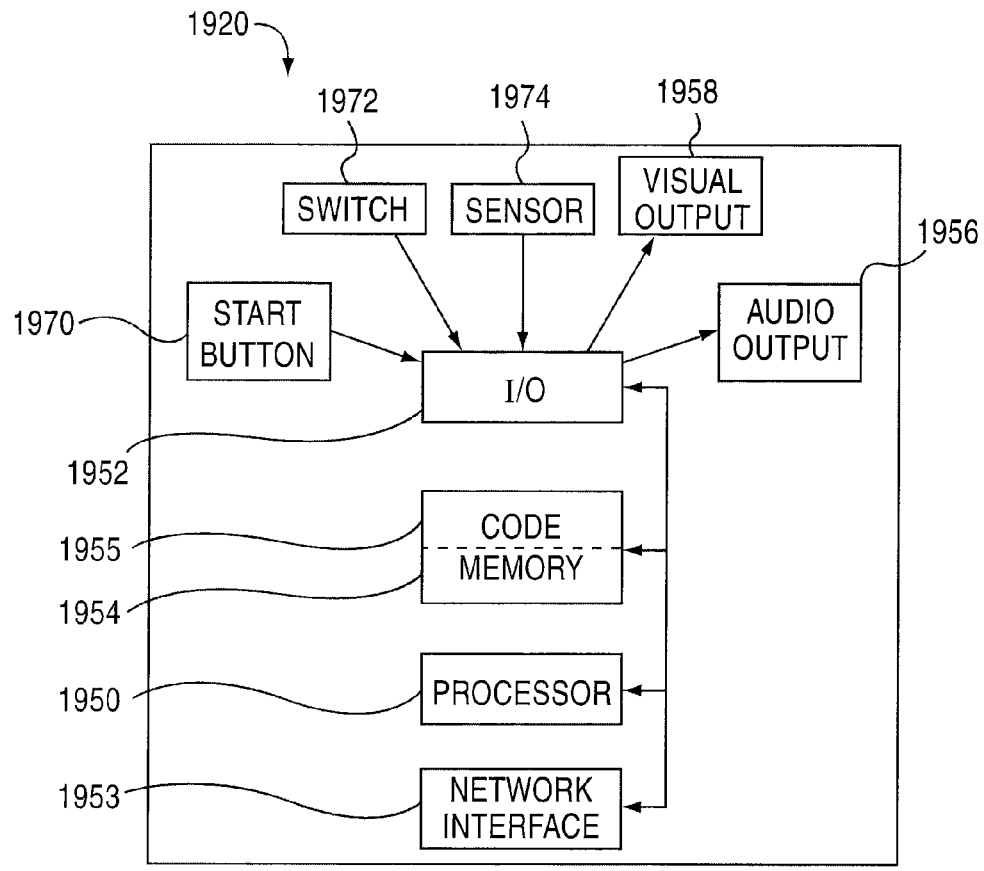
FIG. 3 is a schematic illustration of a portion of the medicament delivery device shown in FIG. 1.

FIG. 3 is a schematic illustration of the electronic circuit system 1920 of the auto-injector 1002. The electronic circuit system 1920 includes a processor 1950 operatively coupled to a memory device 1954. The memory device 1954 can be configured to store processor-readable code 1955 instructing the processor 1950 to perform the functions described above. In some embodiments, the processor-readable code 1955 can be modified and/or updated as circumstances dictate. The electronic circuit system 1920 includes an input/output device 1952 configured to receive electronic inputs from the switches 1972A and 1972B, the proximity sensor 1974 and/or the start button 1970. The input/output device 1952 is also configured to provide electronic signals to the various output devices, such as the visual output devices 1958A and 1958B and the audio output device 1956.

The electronic circuit system 1920 also includes a network interface 1953 configured to couple the electronic circuit system 1920 to a communications network. Such an arrangement can be used, for example, to download replacement processor-readable code 1955 from a central network (not shown) to the memory device 1954. The network interface 1953 can also be configured to transmit information from the electronic circuit system 1920 to a central network, the user's home computer, the user's cell phone or the like.

Figure 4:
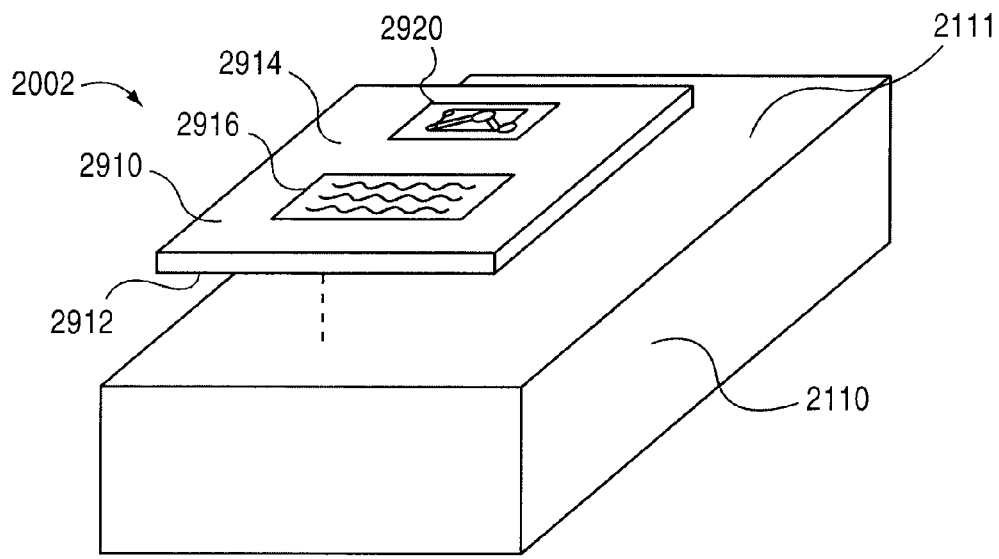
FIG. 4 is a schematic illustration of a medicament delivery device according to an embodiment of the invention.

FIG. 4 is a schematic illustration of a medical device 2002 according to an embodiment of the invention. The medical device 2002, which can be, for example, a medicament delivery device such as an auto-injector, a pen injector, an inhaler, a transdermal delivery system or the like, includes a housing 2110 and a label 2910. The label 2910 is coupled to an outer surface 2111 of the housing 2110. The label 2910 includes a first surface 2912, a second surface 2914 and an electronic circuit system 2920. The first surface 2912 is configured to engage the outer surface 2111 of the housing 2110 to couple the label 2910 to the housing 2110. In some embodiments, the first surface 2912 can include an adhesive to fixedly couple the label 2910 to the housing 2110. The second surface 2914 includes a textual indicia 2916. The textual indicia 2916 can include, for example, a description of the medicament delivery device, a source of the medicament delivery device and/or an instruction associated with the use of the medicament delivery device. Although the first surface 2912 is shown as being opposite the second surface 2914, in other embodiments, the first surface 2912 and the second surface 2914 can be adjacent each other and/or co-planar.

The electronic circuit system 2920 is configured to output an electronic signal. As discussed in more detail herein, the electronic circuit system 2920 can include many components, such as, for example, a processor, a switch, a visual output device and/or an audio output device. The electronic signal can be, for example, an electronic signal communicated to an output device, such as, for example, a visual output device, an audio output device, a haptic output device or the like. In some embodiments, the electronic signal can be associated with an aspect of the medical device 2002, such as an instruction associated with an initial use of the medical device 2002. For example, in some embodiments, the electronic circuit system 2920 can output a text message to a display screen (not shown) disposed on the medical device 2002 instructing the user in the use of the medical device 2002. In other embodiments, the electronic circuit system 2920 can produce an audio output, such as recorded speech, instructing the user in the use of the medical device 2002.

Although the electronic circuit system 2920 is shown as being disposed on the second surface 2914 of the label 2910, in other embodiments, the electronic circuit system can be disposed on the first surface 2912 of the label 2910. In yet other embodiments, the electronic circuit system 2920 can be disposed between the first surface 2912 and the second surface 2914 of the label 2910. In yet other embodiments, the label 2910 can include multiple discrete layers coupled together, within which portions of the electronic circuit system can be disposed.

Figure 5:
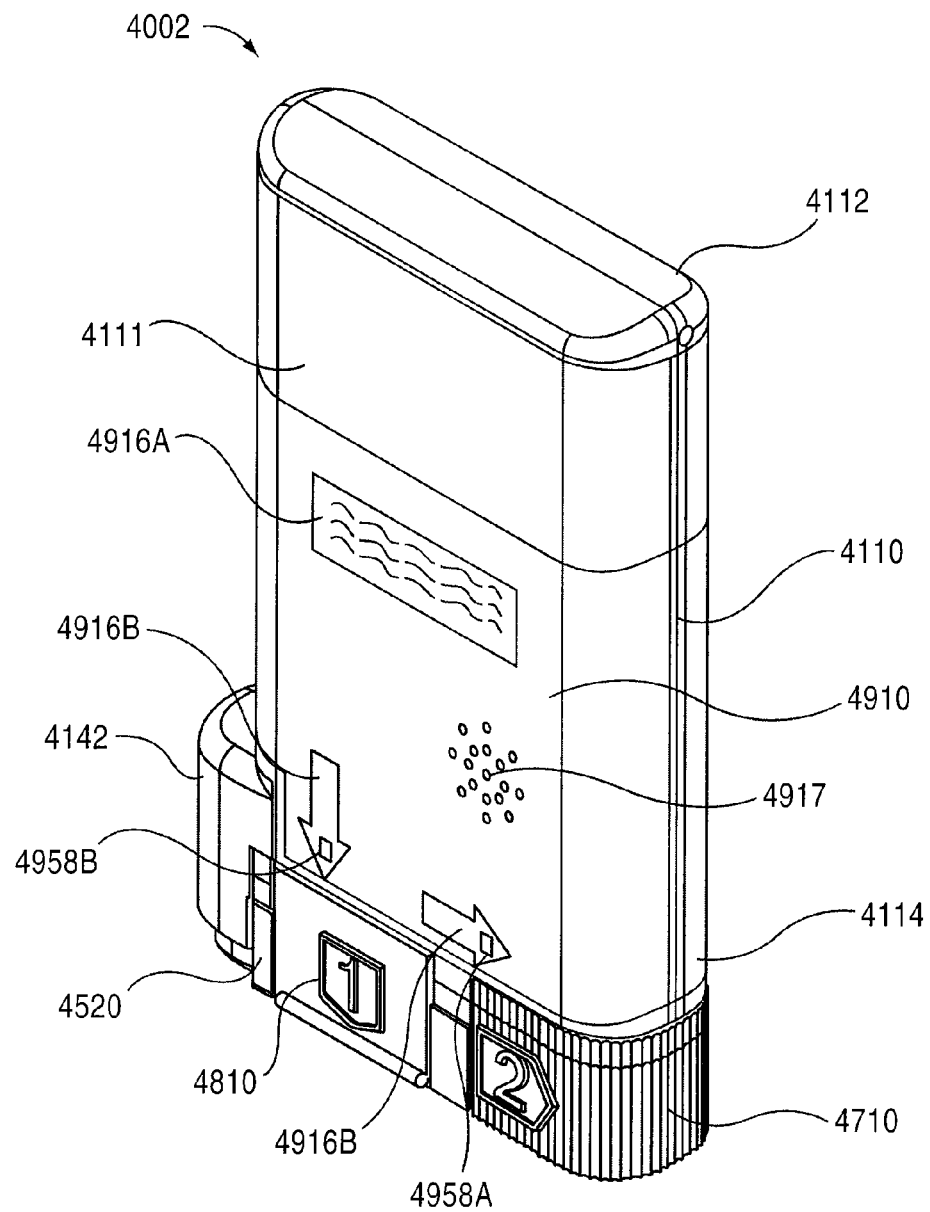
FIG. 5 is a perspective view of an auto-injector according to an embodiment of the invention.

FIG. 5 is a perspective view of an auto-injector 4002 according to an embodiment of the invention. The auto-injector 4002 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, the mechanical components and operation of the auto-injector 4002 are not described in detail herein.

The auto-injector 4002 includes a housing 4110 having a proximal end portion 4112 and a distal end portion 4114. The distal end portion 4114 of the housing 4110 includes a protrusion 4142 to help a user grasp and retain the housing 4110 when using the auto-injector 4002. Said another way, the protrusion 4142 is configured to prevent the auto-injector 4002 from slipping from the user's grasp during use. A base 4520 is movably coupled to the distal end portion 4114 of the housing 4110. A needle guard assembly 4810 is removably coupled to the base 4520. Similarly, a safety lock 4710 is removably coupled to the base 4520. To inject a medicament into the body, the distal end portion 4114 of the housing is oriented towards the user such that the base 4520 is in contact with the portion of the body where the injection is to be made. The base 4520 is then moved towards the proximal end 4112 of the housing 4110 to actuate the auto-injector 4002.

Figure 6:
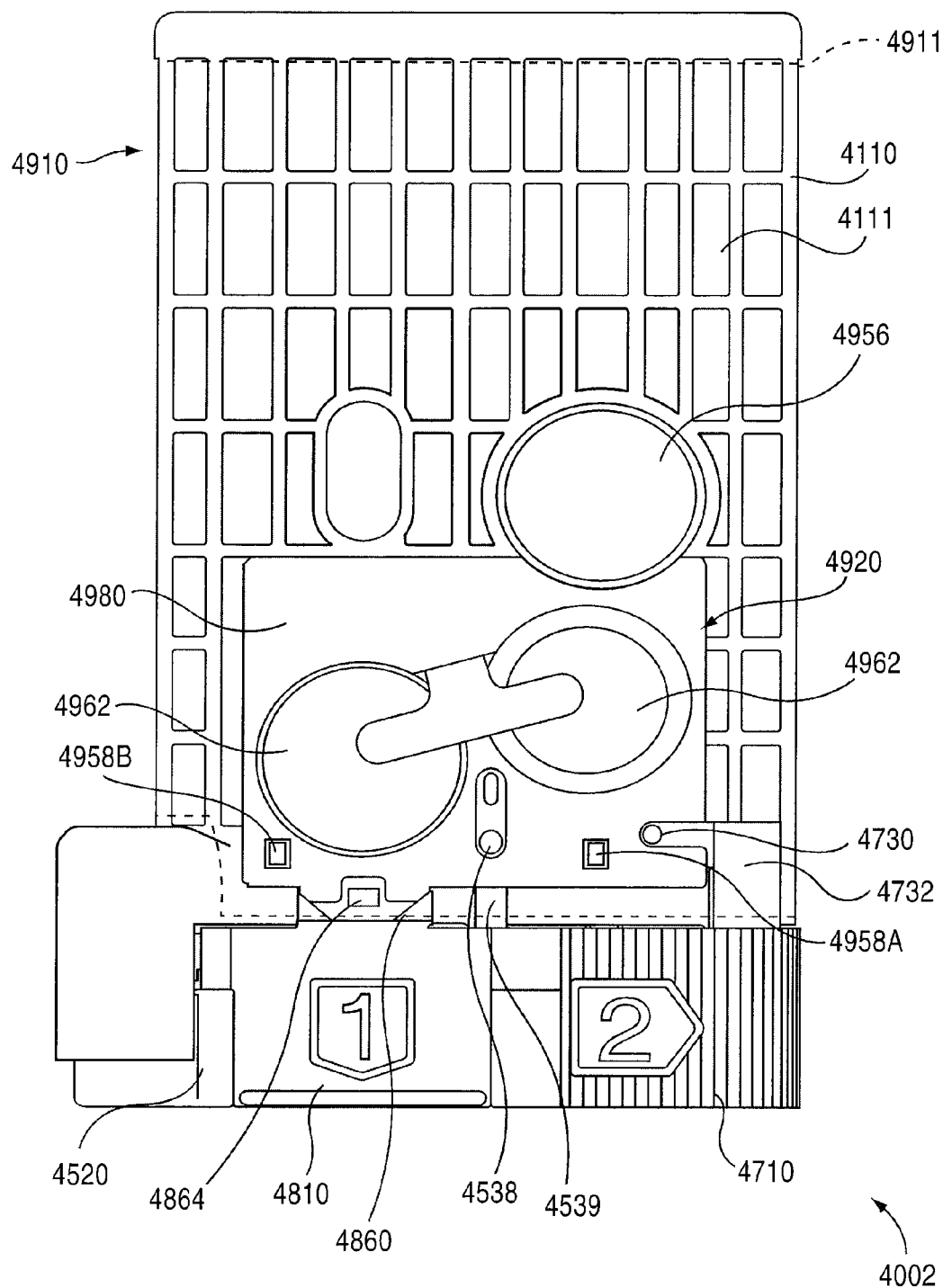
FIG. 6 is a front view of the auto-injector illustrated in FIG. 5, with a portion of the auto-injector illustrated in phantom lines for ease of reference.
Figure 7:
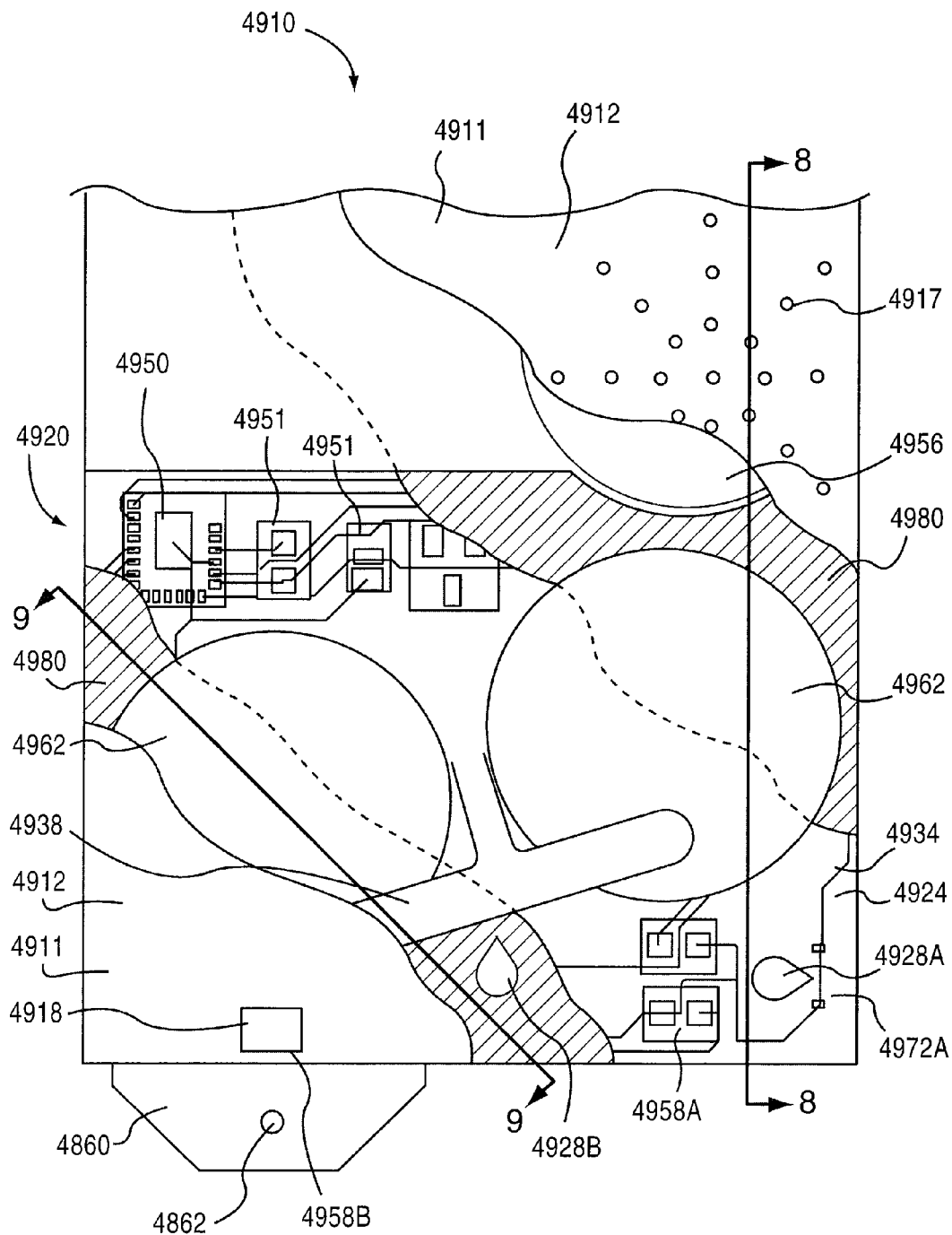
FIG. 7 is a partial cut-away front view of a portion of the auto-injector illustrated in FIG. 5.
Figure 8:
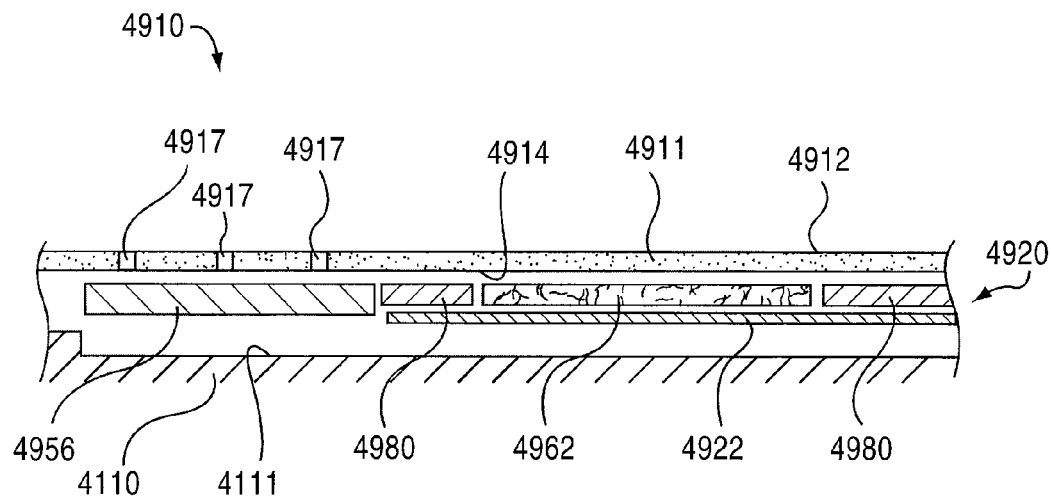
FIG. 8 is a cross-sectional view of a portion of the auto-injector illustrated in FIG. 5 taken along line 8-8 in FIG. 7.
Figure 9:
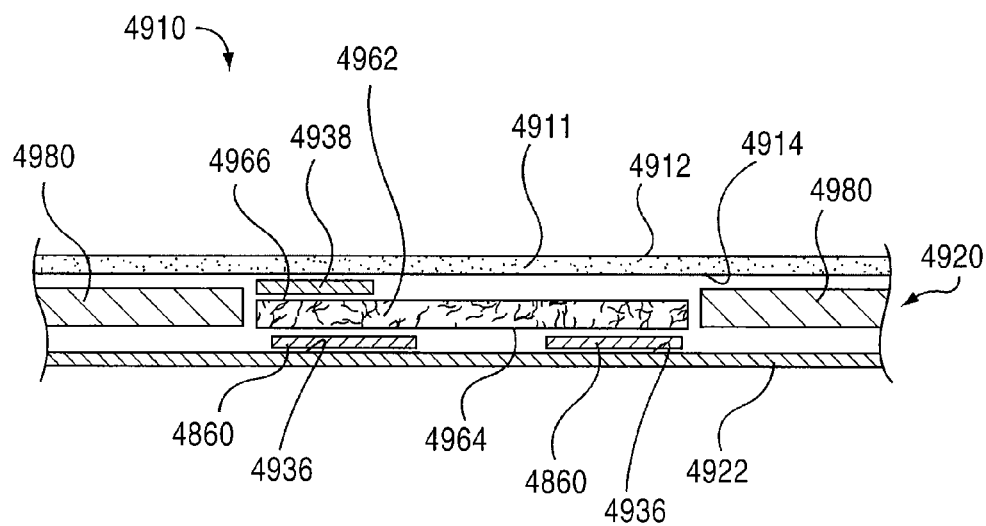
FIG. 9 is a cross-sectional view of a portion of the auto-injector illustrated in FIG. 5 taken along line 9-9 in FIG. 7.

The auto-injector 4002 includes a label 4910 coupled to an outer surface 4111 of the housing 4110. The label 4910 includes an outer layer 4911, an intermediate layer 4980 and an electronic circuit system 4920 (see FIGS. 7-9). FIG. 6 is a front view of the auto-injector 4002 showing the outer layer 4911 of the label 4910 in phantom lines so that the intermediate layer 4980 and an electronic circuit system 4920 can be more clearly seen. As shown in FIGS. 7-9, the outer layer 4911, which, in some embodiments, can be constructed from paper, has a first surface 4912 and a second surface 4914 opposite the first surface 4912. Multiple indicia 4916 are disposed on the first surface 4912. The indicia 4916 include a textual indicia 4916A and two symbolic indicia 4916B. The textual indicia 4916B can be written text describing the medicament delivery device, indicating a source of the medicament delivery device and/or instructing a user in the use of the medicament delivery device. The symbolic indicia 4916B can include, for example, arrows, pointers, trademarks, symbols describing the use of the medicament delivery device or the like. The label 4910 is coupled to the outer surface 4111 of the housing 4110 such that the portion of the first surface 4912 including the indicia 4916 is visible.

A portion of the second surface 4914 of the outer layer 4911 can be coupled to the outer surface 4111 of the housing 4110 by any suitable method. For example, in some embodiments, the second surface 4914 of the outer layer 4911 includes an adhesive configured to bond the outer layer 4911 to the outer surface 4111 of the housing 4110. Other portions of the second surface 4914 of the outer layer 4911 are adjacent the intermediate layer 4980 and portions of the electronic circuit system 4920. In this manner, the outer layer 4911 of the label 4910 retains the intermediate, or spacer, layer 4980 and the electronic circuit system 4920 in a predetermined position against the outer surface 4111 of the housing 4110.

The outer layer 4911 of the label 4910 includes multiple openings 4917 adjacent the audio output device 4956. In this manner, sound waves produced by the audio output device 4956 can be transmitted to an area outside of the housing 4110. Similarly, the outer layer 4911 of the label 4910 includes openings 4918 adjacent the light emitting diodes (LEDs) 4958A and 4958B to allow the user to see the visual output. In some embodiments, the outer layer 4911 of the label 4910 can include a transparent portion adjacent the LEDs 4958A and 4958B to allow the user to see the visual output.

The electronic circuit system 4920 includes a printed circuit board 4922 upon which a microprocessor 4950, two LEDs 4958A and 4958B, two switches 4972A and 4972B and various electronic components 4951, such as, for example, resistors, capacitors and diodes, are mounted. The electronic circuit system 4920 also includes an audio output device 4956, such as, for example, a micro-speaker, coupled to the outer surface 4111 of the housing 4110 adjacent the printed circuit board 4922. The printed circuit board 4922 includes a substrate 4924 upon which a series of electrical conductors 4934, such as for example, copper traces, are etched. The substrate 4924 can be constructed from any material having suitable electrical properties, mechanical properties and flexibility, such as, for example Mylar®, Kapton® or impregnated paper.

A mask layer (not shown) is disposed over the substrate 4924 to electrically isolate selected portions of the electrical conductors 4934 from adjacent components. The electrical conductors 4934 operatively couple the above-mentioned circuit components in a predetermined arrangement. In this manner, the electronic circuit system 4920 can be configured to output, via the LEDs 4958A and 4958B and/or the audio output device 4956, a predetermined sequence of electronic outputs during the use of the auto-injector 4002.

Power is supplied to the electronic circuit system 4920 by two batteries 4962 connected in series. The batteries can be, for example, three volt, "watch-style" lithium batteries. As shown in FIG. 9, each of the batteries 4962 has a first surface 4964 and a second surface 4966 opposite the first surface. The first surface 4964 can be, for example, an electrically negative terminal. Similarly, the second surface 4966 can be an electrically positive terminal. As discussed in more detail herein, the batteries 4962 are positioned such that a first electrical contact portion 4936 of the printed circuit board 4922 can be placed in contact with the first surface 4964 of the battery 4962 and a second electrical contact portion 4938 of the printed circuit board 4922 can be placed in contact with the second surface 4966 of the battery 4962. In this manner, the batteries 4962 can be operatively coupled to the electronic circuit system 4920.

As shown in FIGS. 7 and 9, a battery isolation tab 4860 is movably disposed between the first electrical contact portion 4936 of the printed circuit board 4922 and the first surface 4964 of one of the batteries 4962. The battery isolation tab 4860 can be constructed from any electrically isolative material, such as, for example, Mylar®. As discussed in more detail herein, in this manner, the batteries 4962 can be selectively placed in electronic communication with the electronic circuit system 4920.

The intermediate, or spacer, layer 4980 is disposed between the outer layer 4911 and the electronic circuit system 4920. The intermediate layer 4980 includes openings (not shown) within which various components of the electronic circuit system, such as, for example, the batteries 4962 are disposed. The intermediate layer 4980 is sized to maintain a predetermined spacing between the various components included in the label 4910. The intermediate layer can be constructed from any suitable material, such as, for example, flexible foam having an adhesive surface, polycarbonate or the like.

Figure 10:
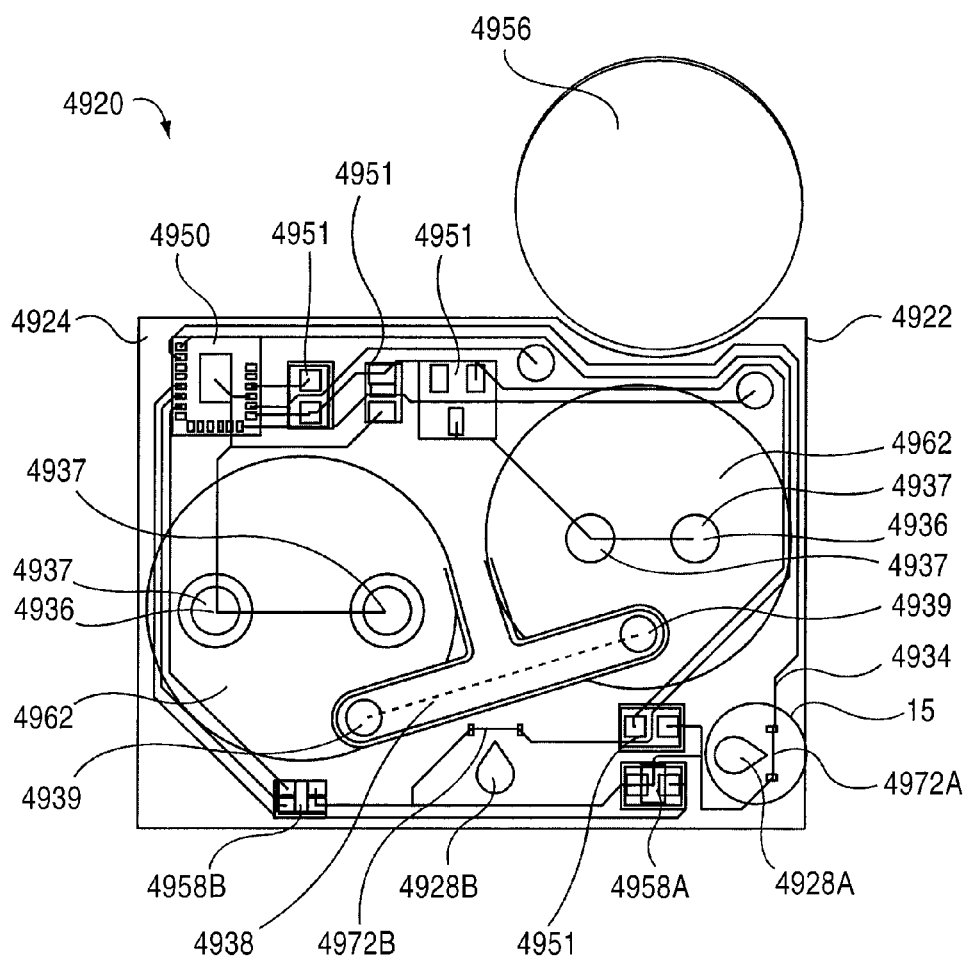
FIG. 10 is a front view of a portion of the auto-injector illustrated in FIG. 5.
Figure 11:
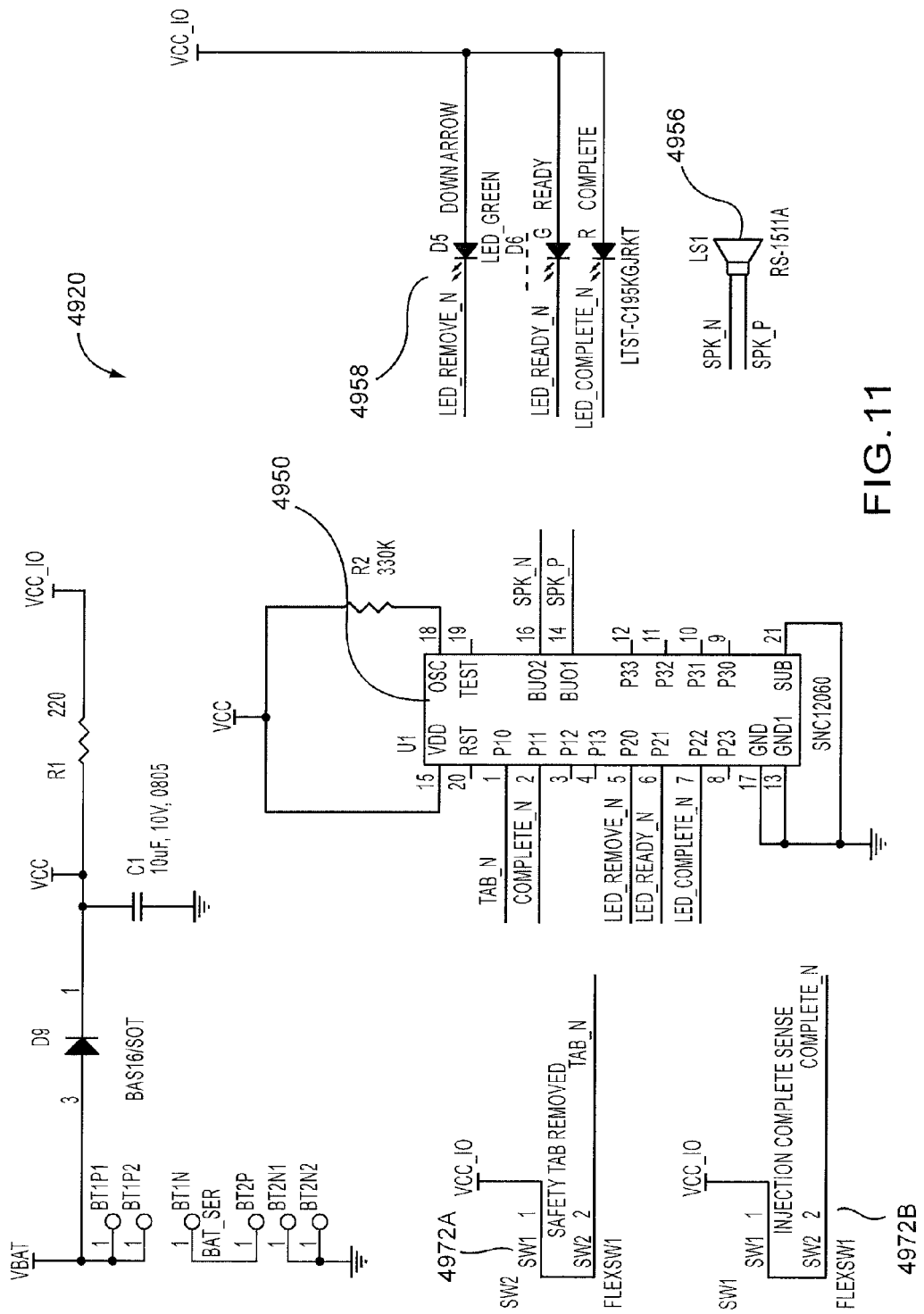
FIG. 11 is a schematic illustration of a portion of the auto-injector illustrated in FIG. 5.

FIG. 10 is a front view of the electronic circuit system 4920 showing the arrangement of the various components (i.e., the microprocessor 4950, LEDs 4958A and 4958B, switches 4972A and 4972B, audio output device 4956 or the like). FIG. 11 is a schematic illustration of the electronic circuit system 4920.

The operation of the auto-injector 4002 and the electronic circuit system 4920 is now discussed with reference to FIGS. 12-14. The actuation of the electronic circuit system 4920 includes several operations that are incorporated into the standard procedures for using the auto-injector 4002. In this manner, the user can actuate the electronic circuit system 4920 without completing any additional operations.

Figure 12:
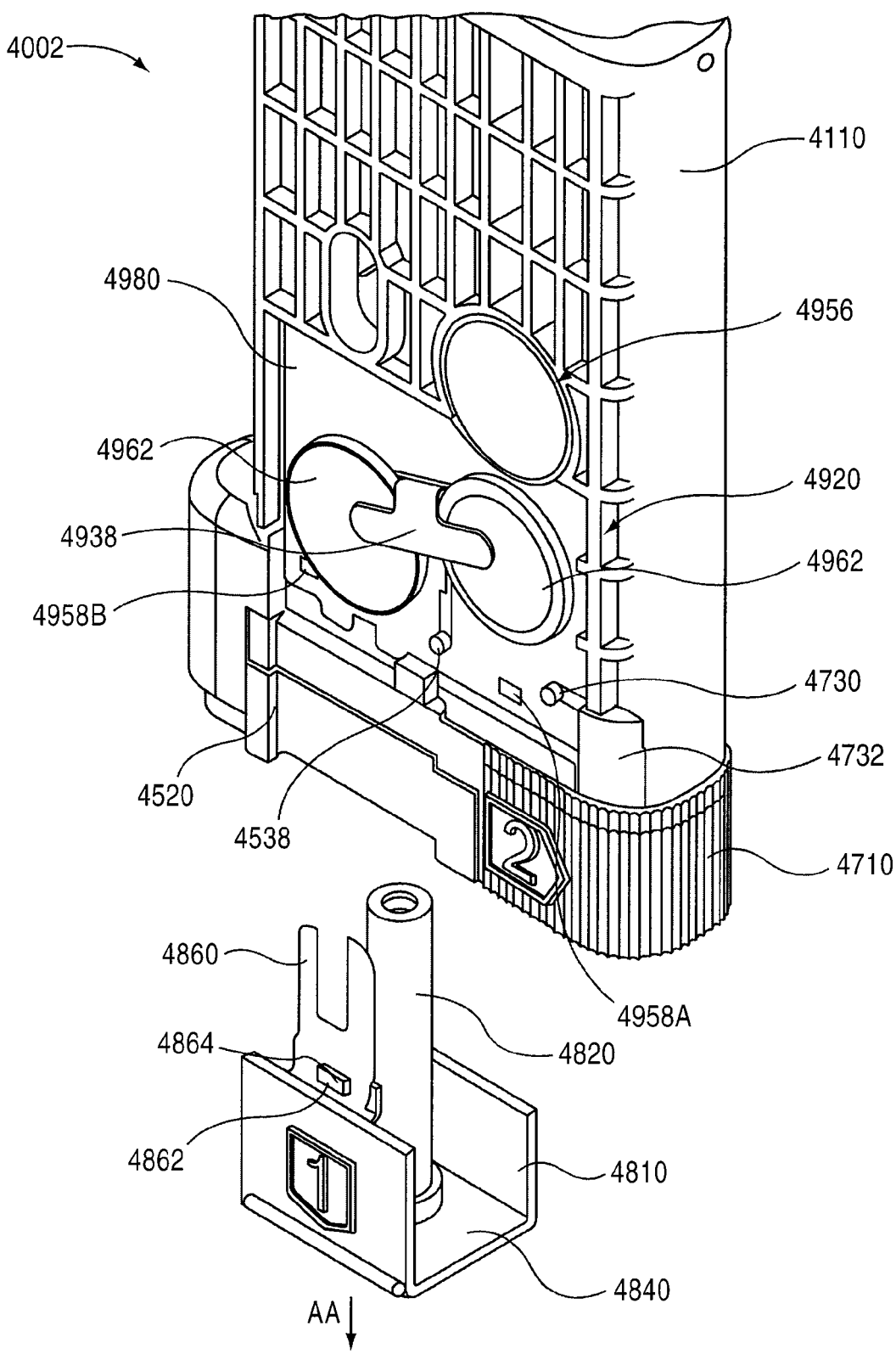
FIG. 12 is a perspective view of a portion of the auto-injector illustrated in FIG. 5 in a second configuration.
Figure 13:
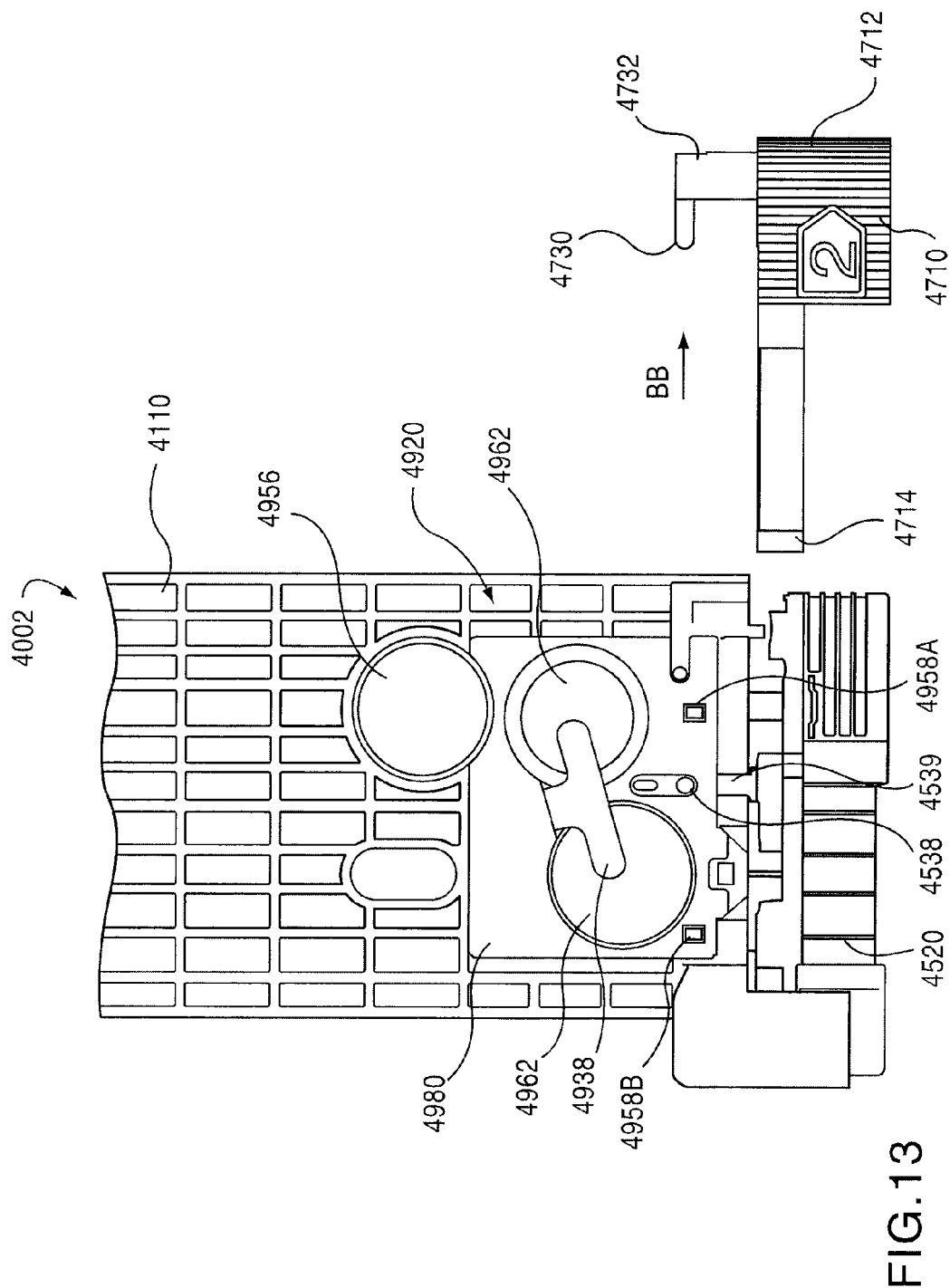
FIG. 13 is a perspective view of a portion of the auto-injector illustrated in FIG. 5 in a third configuration.

Prior to use, the auto-injector 4002 is first enabled by removing the needle guard 4810 and the safety lock 4710 (see FIGS. 12 and 13). As illustrated by arrow AA in FIG. 12, the needle guard 4810 is removed by moving it distally. The needle guard 4810 includes a sheath retainer 4840 and a sheath 4820. The sheath 4820 is configured to receive a portion of the needle (not shown) when the needle guard 4810 is in a first (or installed) position. The sheath retainer 4840 is coupled to the sheath 4820 such that when the sheath retainer 4840 is moved distally away from the base 4520 into a second (or removed) position, the sheath 4820 is removed from the needle.

The sheath retainer 4840 includes an actuator 4864 that is received by an opening 4862 in the isolation tab 4860. Accordingly, when the sheath retainer 4840 is moved distally away from the base 4520, the isolation tab 4860 is removed from the area between the first electrical contact portion 4936 of the printed circuit board 4922 and the first surface 4964 of one of the batteries 4962. In this manner, the batteries 4962 can be operatively coupled to the electronic circuit system 4920 when the needle guard 4810 is removed, thereby actuating the electronic circuit system 4920.

When actuated, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a .WAV file that contains a recorded instruction instructing the user in the operation of the auto-injector 4002. Such an instruction can state, for example, "remove the blue safety tab near the base of the auto-injector." The processor can simultaneously output an electronic signal to the first LED 4958A, thereby causing the first LED 4958A, which is located near the safety lock 4710, to flash a particular color. In this manner, the electronic circuit system 4920 can provide both audible and visual instructions to assist the user in the initial operation of the auto-injector 4002.

In other embodiments, the electronic circuit system 4920 can output an electronic output associated with a description and/or status of the auto-injector 4002 and/or the medicament contained therein. For example, in some embodiments, electronic circuit system 4920 can output an audible message indicating the type of medicament contained in the auto-injector, the expiration date of the medicament, the dosage of the medicament or the like.

As illustrated by arrow BB in FIG. 13, the safety lock 4710 is removed by moving it substantially normal to the longitudinal axis of the housing 4110. The safety lock 4710 has a first end 4712 and a second end 4714. When the safety lock 4710 is in its first (or locked) position, the second end 4714 extends around a portion of the base 4520 to space the base 4520 apart from the distal end portion 4114 of the housing 4110. Additionally, the first end 4714 includes a locking protrusion (not shown) that obstructs portions of the system actuator (not shown) further preventing the base 4520 from being moved proximally towards the housing 4110. Accordingly, when the safety lock 4710 is in its first position, the auto-injector 4002 cannot be actuated.

Figure 15:
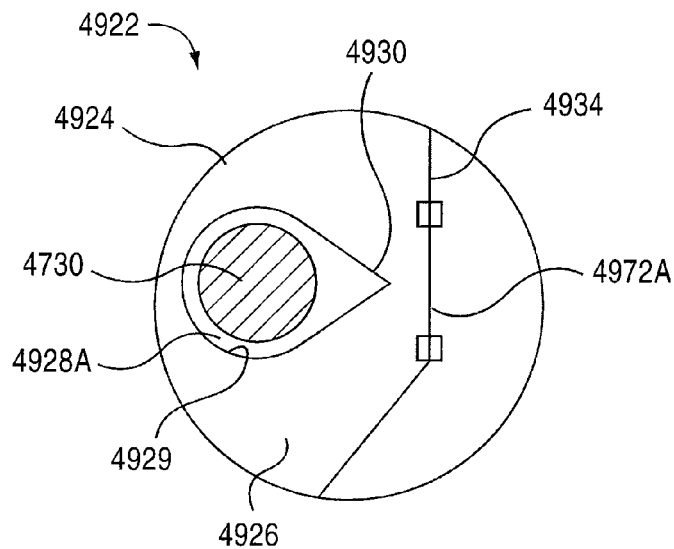
FIGS. 15 and 16 are front views of a portion of the auto-injector labeled as region 15 in FIG. 10, in a first configuration and a second configuration, respectively.
Figure 16:
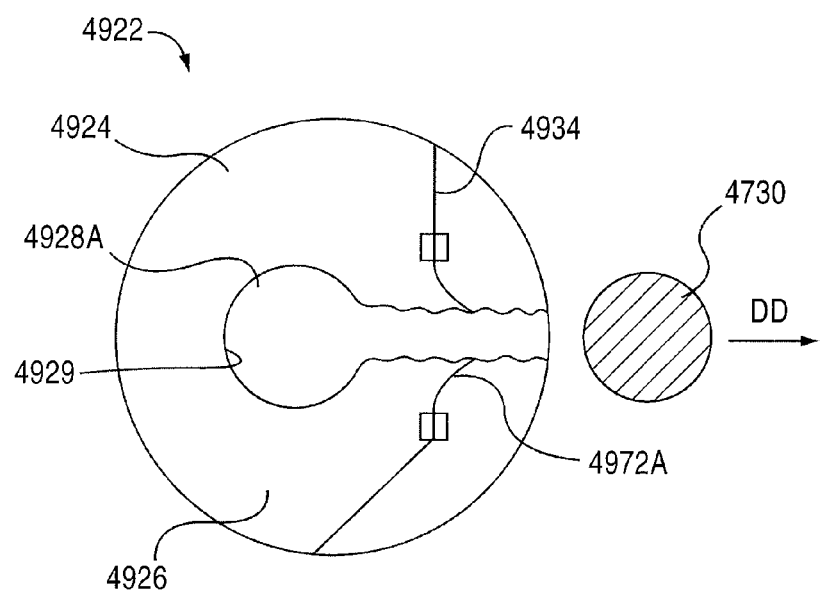

In some embodiments, the safety lock 4710 includes an actuator 4732 that actuates the electronic circuit 4920 to trigger a predetermined output or sequence of outputs when the safety lock 4710 is moved from the first position to a second (or unlocked) position, as shown in FIG. 13. More particularly, as shown in FIGS. 10, 15 and 16, the actuator 4732 includes a protrusion 4730 that is received within a first opening 4928A defined by an actuation portion 4926 of the substrate 4924 when the safety lock 4710 is in the first position. The boundary 4929 of the first opening 4928A has a discontinuous shape, such as, for example, a teardrop shape, that includes a stress concentration riser 4930. The discontinuity and/or the stress concentration riser 4930 of the boundary 4929 can be of any suitable shape to cause the substrate 4924 to deform in a predetermined direction when the protrusion 4730 is moved relative to the first opening 4928A.

As shown in FIGS. 15 and 16, the first opening 4928A is defined adjacent an electrical conductor 4934 that, as discussed above, electronically couples the components included in the electronic circuit system 4920. The electrical conductor 4934 includes a first switch 4972A, which can be, for example a frangible portion of the electrical conductor 4934. In use, when the safety lock 4710 is moved from the first position to the second position, the actuator 4732 moves in a direction substantially parallel to a plane defined by a surface of the actuation portion 4926 of the substrate 4924. The movement of the actuator 4732 causes the protrusion 4730 to move within the first opening 4928A, as indicated by the arrow DD in FIG. 16. The movement of the protrusion 4730 tears the actuation portion 4926 of the substrate 4924, thereby separating the portion of the electrical conductor 4934 including the first switch 4972A. Said another way, when the safety lock 4710 is moved to the second position, the actuator 4732 moves irreversibly the first switch 4972A from a first state (e.g., a state of electrical continuity) to a second state (e.g., a state of electrical discontinuity).

When the actuator 4732 actuates the electronic circuit system 4920 as described above, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a recorded message notifying the user of the status of the auto-injector 4002. Such a status message can state, for example, "The auto-injector is now enabled." The processor can also simultaneously output an electronic signal to the first LED 4958A, thereby causing the first LED 4958A to stop flashing, change color or the like.

In some embodiments, the electronic circuit system 4920 can be configured to output the status message for a predetermined time period, such as, for example, five seconds. After the predetermined time period has elapsed, the electronic circuit system 4920 can output an audible message further instructing the user in the operation of the auto-injector 4002. Such an instruction can state, for example, "Place the base of the auto-injector against the patient's thigh. To complete the injection, press the base firmly against the patient's thigh." In some embodiments, the processor can simultaneously output an electronic signal to the second LED 4958B, thereby causing the second LED 4958B, which is located near the base 4520, to flash a particular color. In this manner, the electronic circuit system 4920 can provide both audible and visual instructions to assist the user in the placement and actuation of the auto-injector 4002. In some embodiments, the electronic circuit system 4920 can be configured to repeat the instructions after a predetermined time period has elapsed.

Figure 14:
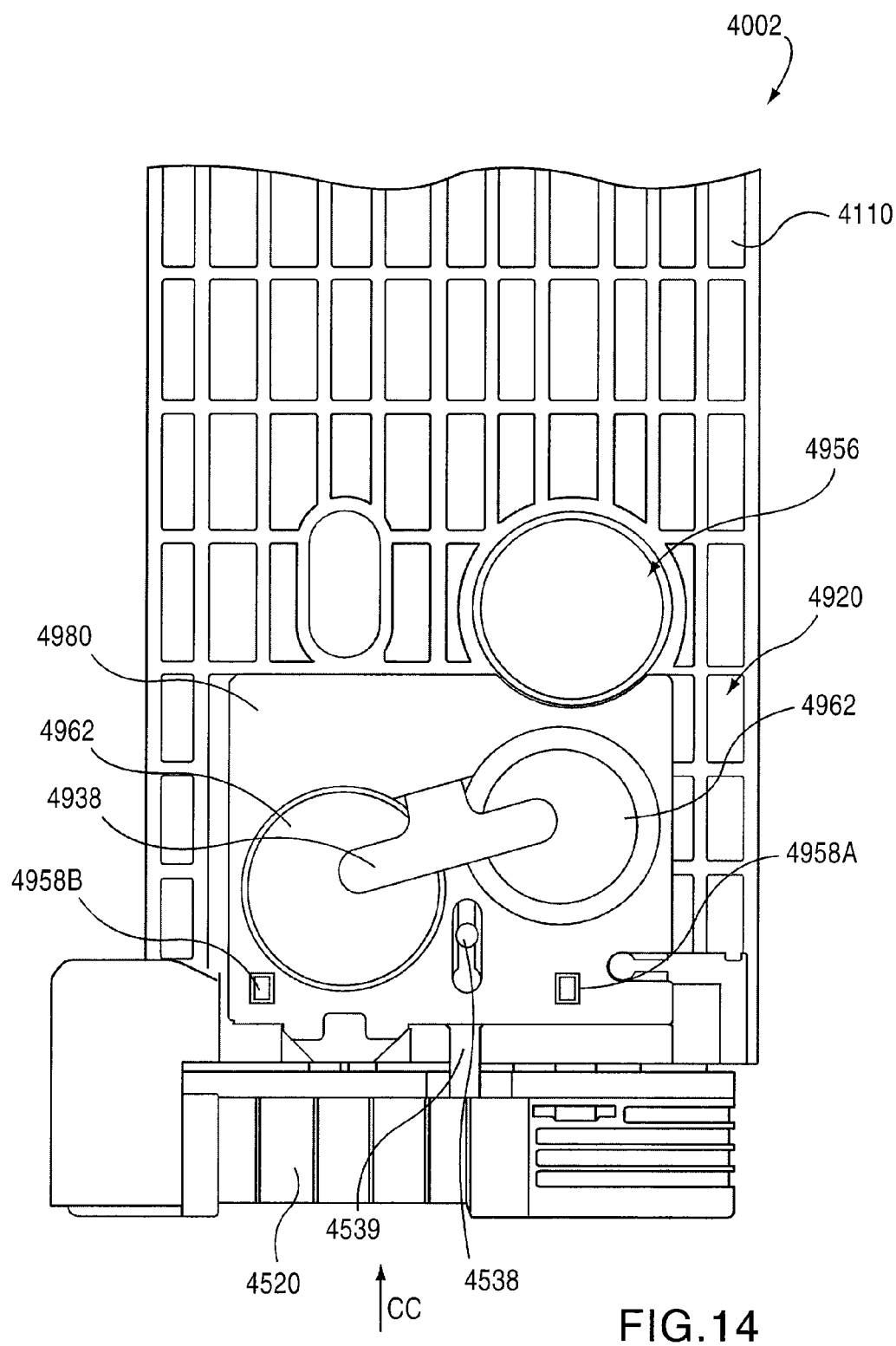
FIG. 14 is a perspective view of a portion of the auto-injector illustrated in FIG. 5 in a fourth configuration.

After the auto-injector 4002 is enabled and placed against the body of the patient, the auto-injector 4002 is actuated by moving the base 4520 proximally towards the housing 4110, as illustrated by arrow CC in FIG. 14. The base 4520 includes an actuator 4538 that actuates the electronic circuit 4920 to trigger a predetermined output or sequence of outputs when the base 4520 is moved from a first position to a second position, as shown in FIG. 13. The actuator 4538 includes a protrusion 4539 that is received within a second opening 4928B (see FIG. 10) defined by the substrate 4924 when the base 4520 is in the first position. The configuration and operation of the protrusion 4539, the second opening 4928B and the second switch 4972B are similar to the configuration and operation of the protrusion 4730, the first opening 4928A and the first switch 4972A, and are therefore not described in detail.

When the actuator 4538 actuates the electronic circuit system 4920, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The processor can also simultaneously output an electronic signal to the first LED 4958A, thereby causing the first LED 4958A to stop flashing, change color or the like, to provide a visual indication that the injection is complete.

Figure 17:
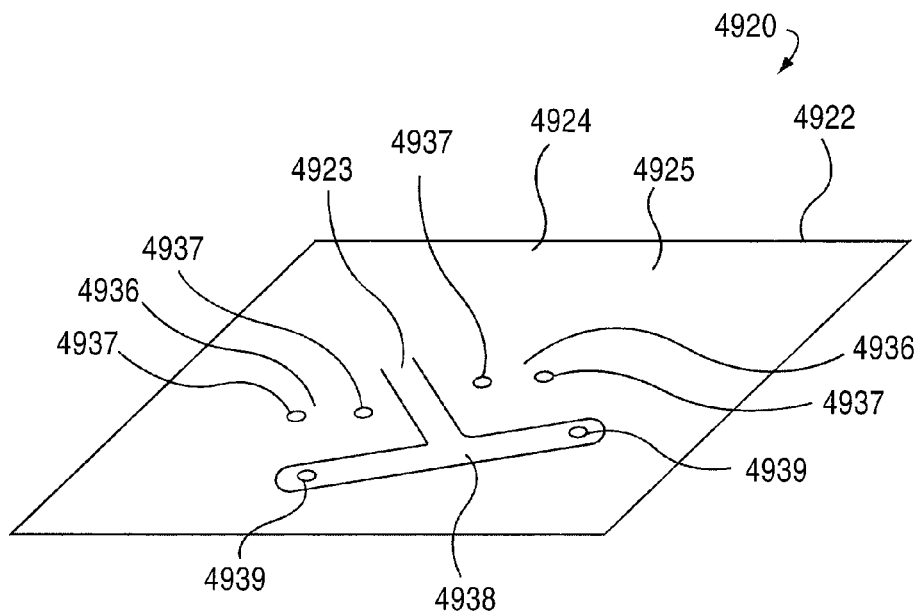
FIGS. 17 through 20 are perspective views of a portion of the auto-injector illustrated in FIG. 10, in a first configuration, a second configuration, a third configuration and a fourth configuration, respectively.

As described above, the batteries 4962 are positioned such that the first electrical contact portions 4936 of the printed circuit board 4922 can be placed in contact with the first surface 4964 of each battery 4962 and the second electrical contact portion 4938 of the printed circuit board 4922 can be placed in contact with the second surface 4966 of each battery 4962. As shown in FIGS. 10 and 17, the first electrical contact portions 4936 each include a pair of electrical contacts 4937 that are operatively coupled to the electronic circuit system 4920. Similarly, the second electrical contact portion 4938 includes a pair of electrical contacts 4939 that is operatively coupled to the electronic circuit system 4920.

Figure 21:
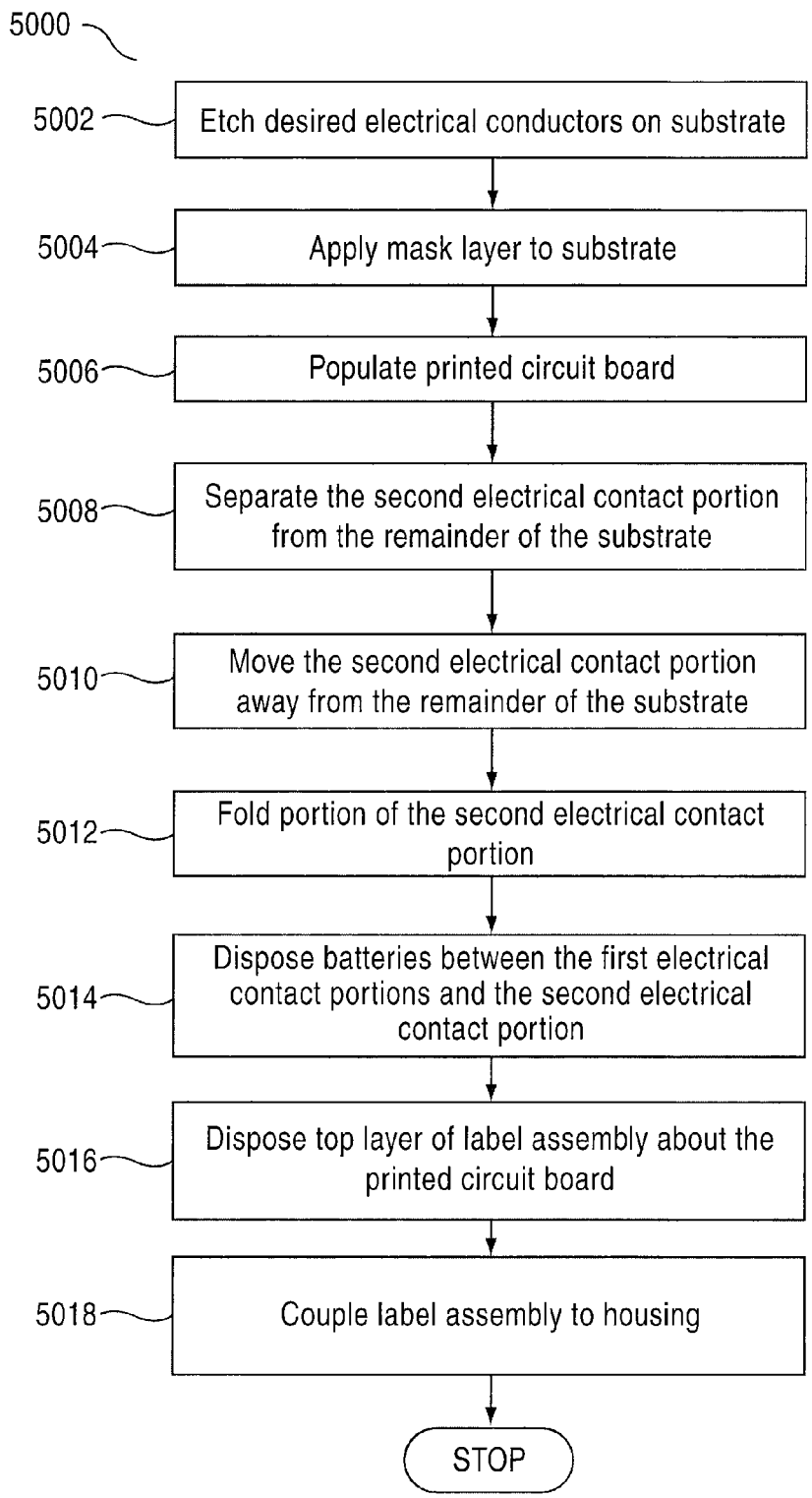
FIG. 21 is a flow chart of a method according to an embodiment of the invention.

The first electrical contact portions 4936 and the second electrical contact portion 4938 are monolithically constructed from the printed circuit board 4922. FIGS. 17-20 are perspective views showing the printed circuit board 4922 in various stages of manufacture. FIG. 21 is a flow chart illustrating a method 5000 for manufacturing a flexible printed circuit board according to an embodiment of the invention. The illustrated method includes disposing a copper layer on the top surface 4925 of the flexible substrate 4924 and etching the desired series of electrical conductors (not shown in FIGS. 17-20) at 5002. A mask layer (not shown) is disposed on portions of the top layer 4925 of the substrate 4924 to electrically isolate selected portions of the electrical conductors from adjacent components at 5004. During this operation, the electrical contacts 4937, 4939 are constructed.

The printed circuit board 4922 is then populated with the microprocessor, switches, output devices and/or other electronic components to form the electronic circuit system 4920 at 5006. For clarity, the circuit components are not shown in FIGS. 17-20. After the printed circuit board 4922 is populated, the portion of the flexible substrate 4924 forming the second electrical contact portion 4938 is separated from the remainder of the substrate 4924 at 5008. As shown in FIG. 17, during this operation, a portion 4923 of the boundary between the second electrical contact portion 4938 and the remainder of the substrate 4924 is left intact.

Figure 18:
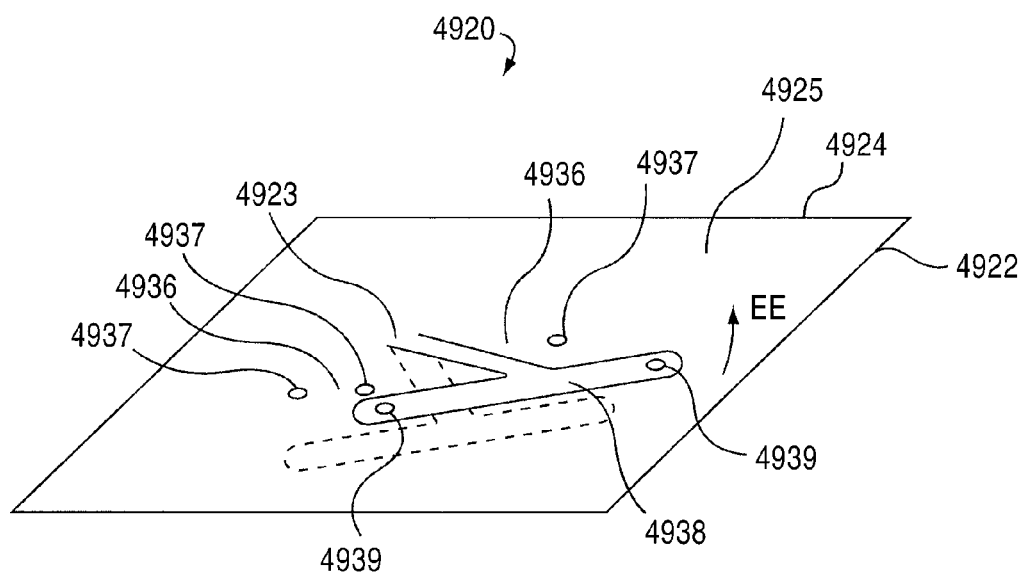
Figure 19:
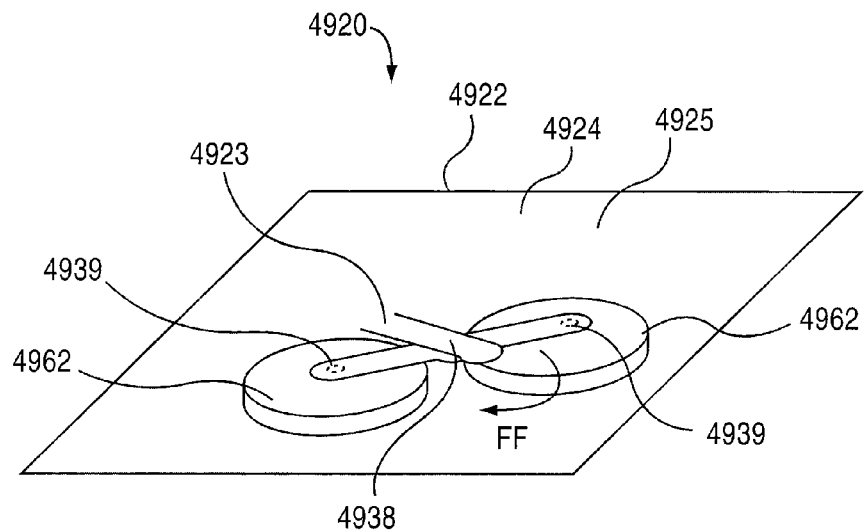
Figure 20:
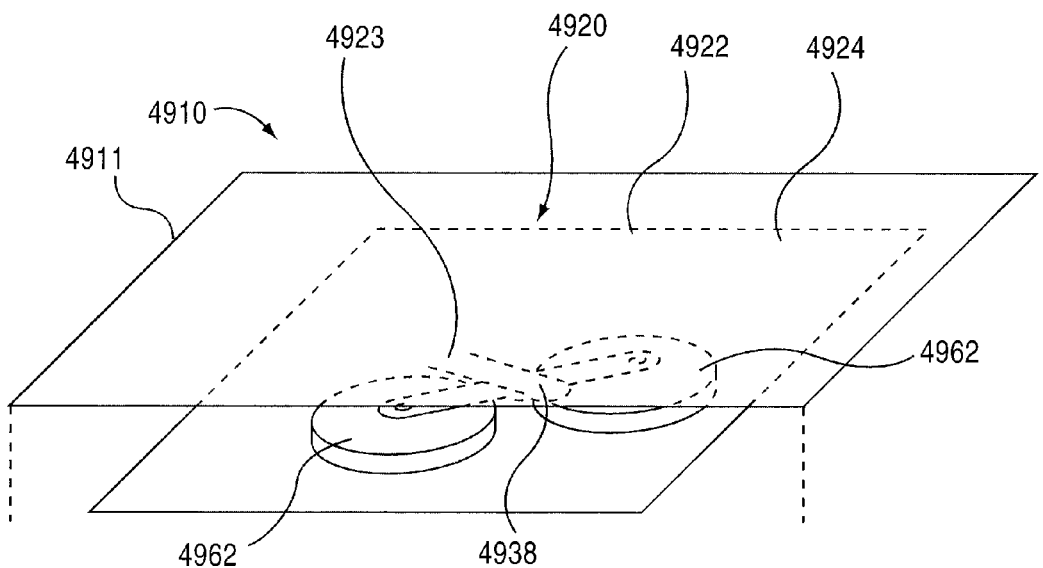

As shown by the arrow EE in FIG. 18, the second electrical contact portion 4938 is then moved upwardly away from the remainder of the substrate 4924 at 5010. In this manner, the second electrical contact portion 4938 is spaced apart from the first electrical contact portions 4936. As shown by the arrow FF in FIG. 19, the portion of the second electrical contact portion 4938 containing the electrical contacts 4939 is then folded so that the electrical contacts 4939 on the second electrical contact portion 4938 are facing the electrical contacts 4937 on the first electrical contact portions 4936, at 5012. In this manner, opposing electrical contacts 4937, 4939 are constructed on the printed circuit board 4922 without disposing electrical conductors on and/or etching multiple surfaces of the printed circuit board 4922.

The batteries 4962 are then disposed between the first electrical contact portions 4936 and the second electrical contact portion 4938 at 5014. Although not shown in FIG. 19, in some embodiments, a battery isolation tab of the type discussed above can be disposed between one of the batteries and the printed circuit board 4922. Once the batteries 4962 are in place, the top layer 4911 of the label 4910 is disposed about the printed circuit board 4922 (see FIG. 20) to maintain the position of the batteries 4962 within the printed circuit board 4922, at 5016. The label assembly 4910 is then coupled to the outer surface of the housing (not shown) at 5018. The label 4910 is coupled to the housing with sufficient tension and/or stretch to maintain the electrical contacts 4937 in electrical communication with the first surface 4964 of each battery 4962 and to maintain the electrical contacts 4939 in electrical communication with the second surface 4966 of each battery 4962. In this manner, the batteries 4962 can be held in place in a printed circuit board 4922 devoid of springs, clips or other rigid members.

As described above, the audio output device 4956, can include, for example, a micro-speaker. In some embodiments, for example, the audio output device 4956 can include an RS-1511A micro-speaker manufactured by Regal Electronics, Inc.

Similarly, the microprocessor 4950 can be a commercially-available processing device dedicated to performing one or more specific tasks. For example, in some embodiments, the microprocessor 4950 can be a commercially-available microprocessor, such as the Sonix SNC 12060 voice synthesizer. Alternatively, the microprocessor 4950 can be an application-specific integrated circuit (ASIC) or a combination of ASICs, which are designed to perform one or more specific functions. In yet other embodiments, the microprocessor 4950 can be an analog or digital circuit, or a combination of multiple circuits.

The microprocessor 4950 can include a memory device (not shown) configured to receive and store information, such as a series of instructions, processor-readable code, a digitized signal, or the like. The memory device can include one or more types of memory. For example, the memory device can include a read only memory (ROM) component and a random access memory (RAM) component. The memory device can also include other types of memory suitable for storing data in a form retrievable by the microprocessor 4950, for example, electronically-programmable read only memory (EPROM), erasable electronically-programmable read only memory (EEPROM), or flash memory.

Figure 22:
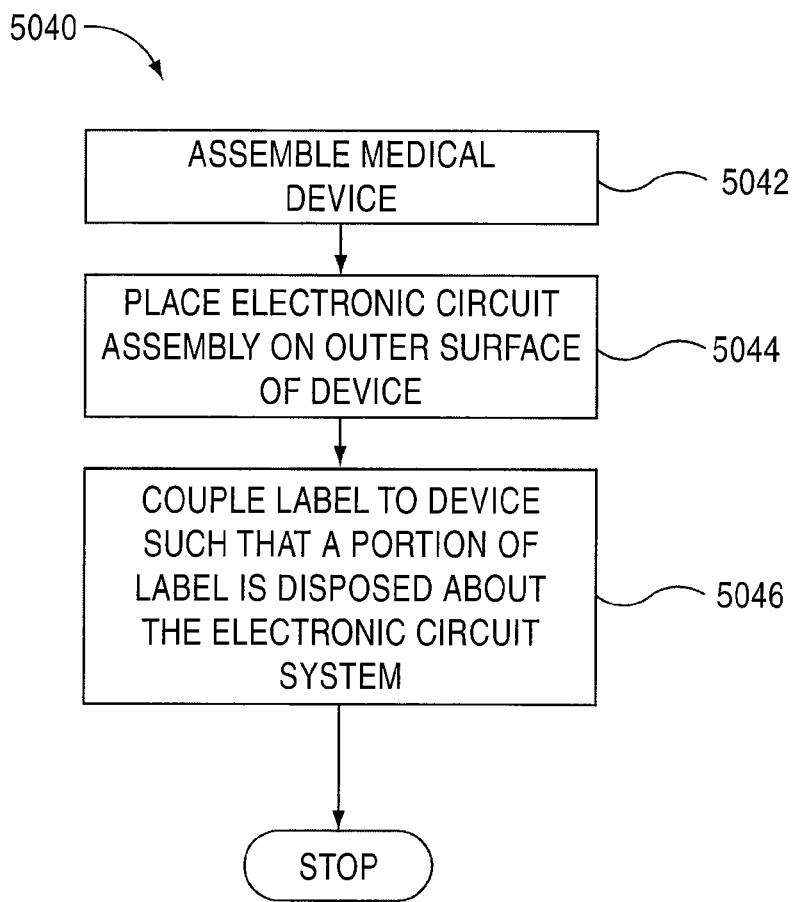
FIG. 22 is a flow chart of a method according to an embodiment of the invention.

FIG. 22 is a flow chart illustrating a method 5040 for manufacturing a medical device according to an embodiment of the invention. The medical device can be any medicament delivery device of the type discussed above, such as, for example, an auto-injector, a pen injector, an inhaler, or a transdermal delivery device. The medical device can also be a medicament container, such as, for example, a pill bottle, a blister pack an intravenous solution bag or the like. The illustrated method includes assembling the medical device, 5042. After the medical device is assembled, an electronic circuit system is placed on an outer surface of the medicament delivery device, 5044. The electronic circuit system can by any electronic circuit system of the type shown and described above. In some embodiments, the electronic circuit system is placed on the outer surface of the medical device in a predetermined orientation. For example, in some embodiments, the electronic circuit system can include openings, such as openings 4928 that are aligned with mating portions of the medical device, such as, for example, protrusions 4730, 4538. In other embodiments, however, the electronic circuit system can be placed on the outer surface of the medical device in any orientation.

After the electronic circuit system is placed on an outer surface of the medical device, a label is coupled to the medical device, 5046. The label, which can be, for example, a label containing a textual indicia, is coupled to the medical device such that a portion of the label is disposed about the electronic circuit system. In this manner, the coupling of the label to the medical device also serves to maintain the electronic circuit system in its position against the outer surface of the medicament delivery device.

Figure 23:
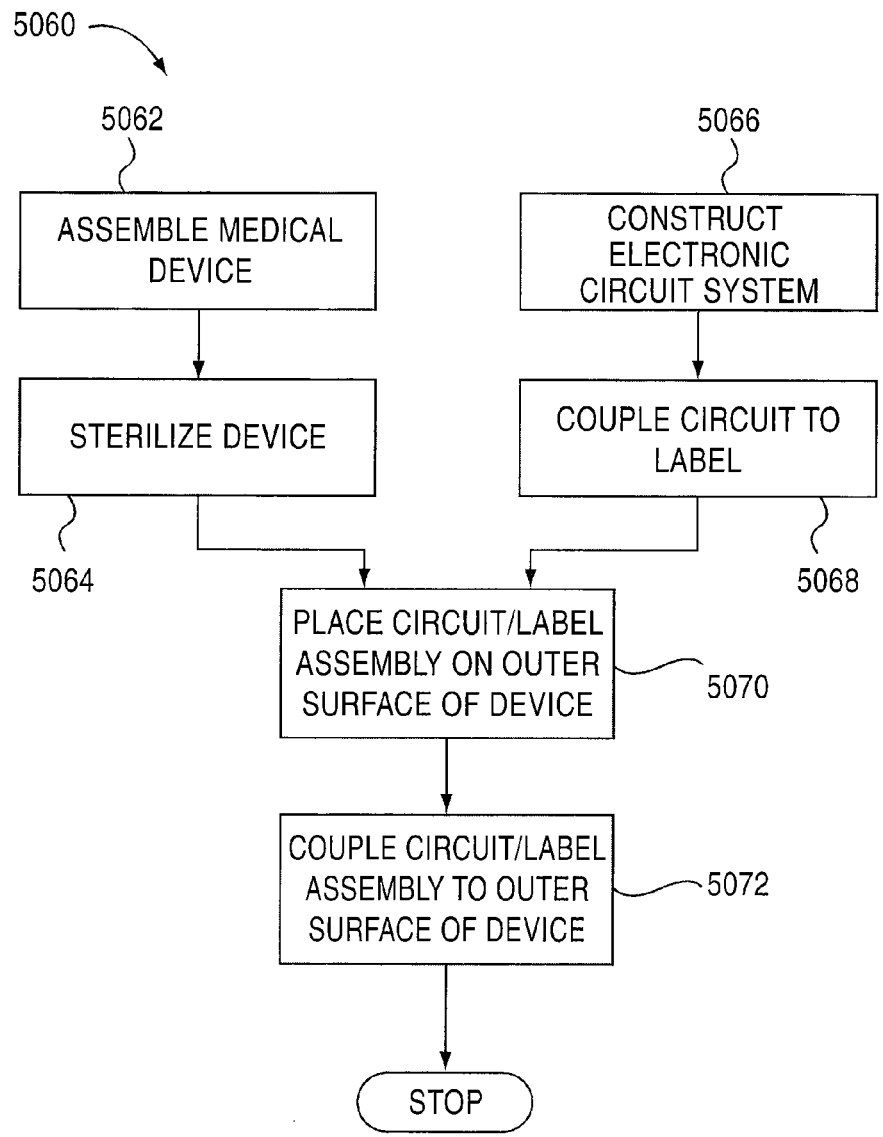
FIG. 23 is a flow chart of a method according to an embodiment of the invention.

FIG. 23 is a flow chart illustrating a method 5060 for manufacturing a medical device according to an embodiment of the invention. The medical device can be any medicament delivery device of the type discussed above, such as, for example, an auto-injector, a pen injector, an inhaler, or a transdermal delivery device. The medical device can also be a medicament container, such as, for example, a pill bottle, a blister pack, an intravenous (IV) bag or the like. The illustrated method includes assembling the medical device, 5062. The medical device is then sterilized using any suitable sterilization process, 5064. In some embodiments, for example, such as those embodiments in which the medicament is epinephrine, the medical device can be sterilized by exposure to ethylene oxide (EtO) gas. In other embodiments, the medical device can be sterilized by exposure to gamma radiation. In yet other embodiments, the medical device can be sterilized by exposure to heat, such as for example, by placing the medicament delivery device into an autoclave.

In parallel with the manufacture of the medical device, the illustrated method includes constructing an electronic circuit system of the type shown and described above, 5066. The electronic circuit system is then coupled to a label, 5068, to form a label assembly. Because the circuit construction is done apart from the manufacture of the medicament delivery device, it is not subjected the sterilization process, which, in some instances, may damage the circuit components.

The illustrated method then includes placing the label assembly on the outer surface of the medical device, 5070. The label assembly is then coupled to the outer surface of the medical device, 5072. In some embodiments, the label assembly can be coupled to the medicament delivery device by an adhesive, an elastic fastener, a shrink wrap or any other suitable method.

While various embodiments of the invention are described herein, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the first surface 4912 of the top layer 4911 of the label 4910 is shown and described as being opposite the second surface 4914 of the top layer 4911 of the label 4910, in other embodiments, the first surface 4912 and the second surface 4914 can be adjacent each other and/or co-planar. Similarly, although the top layer 4911 of the label 4910 is shown and described as covering substantially all of the housing 4110, in some embodiments, the top layer 4911 of the label 4910 can cover only a portion of the housing.

Although the label 4910 is shown and described as including a top layer 4911, an intermediate layer 4980 and a printed circuit board 4922, in some embodiments, the layers comprising the label 4910 can be arranged in any suitable order. For example, in some embodiments, a multi-layered label can include a printed circuit board as an intermediate layer. In other embodiments, a multi-layered label can include a printed circuit board as the outer layer. Moreover, in yet other embodiments, the label need not include multiple layers. For example, in some embodiments, a label can include a single layer that includes an electronic circuit system and textual indicia.

Although the indicia 4916 are shown and described as being visible (e.g., textual indicia and/or symbolic indicia), in some embodiments, a label can include indicia that are haptic. For example, in some embodiments a label can include Braille. In other embodiments, a label can include indicia having a distinct feel, such as for example, a particularly rough or smooth surface.

Although the electronic circuit system 4920 is shown and described as including a printed circuit board 4922 having a flexible substrate 4924, in other embodiments, an electronic circuit system can include a rigid printed circuit board. In yet other embodiments, an electronic circuit system can include a printed circuit board having a substrate having at least a rigid portion.

Moreover, in some embodiments, an electronic circuit system need not include a printed circuit board. For example, in some embodiments, an electronic circuit system can include electronic components operatively coupled by any suitable method other than by a printed circuit board.

Similarly, although the components included in the electronic circuit system 4920 (e.g., the microprocessor 4950, the LEDs 4958A and 4958B or the like) are shown and described as being operatively coupled by electrical conductors 4934, in other embodiments, the components can be operatively coupled without being physically connected. For example, in some embodiments, at least a portion of the components included in an electronic circuit system can be inductively coupled. In other embodiments, at least a portion of the components included in an electronic circuit system can be evanescently coupled.

Although the switches 4972A and 4972B are shown and described as being "tear-through" switches that are monolithically formed from the electrical conductors 4934, in other embodiments, a switch can be formed separately from the electrical conductors 4934. For example, in some embodiments, an electrical circuit system can include a series of first electrical conductors having a first set of characteristics (e.g., the width, height, material from which the conductor is fabricated or the like) and a switch constructed from a second electrical conductor having a second set of characteristics different than the first set of characteristics. In other embodiments, a switch can be a separate component, such as, for example, a microswitch, that is mounted to the printed circuit board. In yet other embodiments, an electrical circuit system can include a "pop-out" switch that includes a biasing member to bias the switch in a predetermined state. In yet other embodiments, an electrical circuit system can include a switch that is disposed at a location other than on a printed circuit board.

Similarly, although the switches 4972A and 4972B are shown and described as being irreversibly movable from a first state to a second state, in other embodiments, a switch can be reversibly movable between a first state and a second state. Moreover, in yet other embodiments, a switch can have more than two distinct states.

Although the actuators 4732, 4539 are shown and described as being configured to move in a direction substantially parallel to the surface of the substrate 4924, in other embodiments, an actuator can be configured to actuate an electronic circuit system by moving in any direction. For example, in some embodiments a circuit actuator can be moved in a direction substantially normal to a portion of an electronic circuit system.

Similarly, although the actuators 4732, 4539 are shown and described as actuating the switches 4972A and 4972B by tearing and/or deforming a portion of the substrate 4924, in other embodiments, a switch can be moved from a first state to a second state without deforming the substrate. For example, in some embodiments, an electronic circuit system can include a printed circuit board having a substrate and a frangible switch tab disposed on the substrate. An electrical conductor and/or a switch can be disposed on the frangible switch tab, such that when the switch tab is removed from the substrate the switch is moved from a first state to a second state. In this manner, the switch can be actuated without tearing and/or deforming a portion of the substrate.

Although the actuators 4732, 4539 are shown and described as being included on the safety lock 4710 and the base 4520, respectively, in other embodiments, the actuators can be included on any component of a medicament delivery device. For example, in some embodiments, an auto-injector can include a start button having an actuator configured to actuate an electronic circuit system. In other embodiments, an auto-injector can include a movable member configured to move a medicament container and/or a needle within a housing of the auto-injector, the movable member including an actuator configured to actuate an electronic circuit system.

Although the safety lock 4710 is shown and described as being removed from the housing 4110 of the auto-injector 4002 when in its second position, in other embodiments, a safety lock can remain coupled to the housing of an auto-injector when in its second position. For example, in some embodiments, a safety lock can be moved from its first position to its second position by rotating a portion of the safety lock.

Certain components of the auto-injector 4002 are shown and described as being coupled together via protrusions and mating openings. The protrusions and/or openings can be disposed on any of the components to be coupled together and need not be limited to only a certain component. For example, the safety lock 4710 is shown and described as including an actuator 4732 having a protrusion 4730 configured to be received within an opening 4928A defined by the substrate 4924. In some embodiments, however, the protrusions can be disposed on the substrate 4924 and the mating openings can be defined by the actuator 4732. In other embodiments, such components can be coupled together in any suitable way, which need not include protrusions and mating openings. For example, in some embodiments, an actuator can be operatively coupled to an actuation portion of a substrate via mating shoulders, clips, adhesive or the like.

Similarly, although certain components of the auto-injector 4002 are shown and described as being constructed from multiple separate components, in some embodiments, such components can be monolithically constructed. For example, the needle guard 4810 and the battery isolation tab 4860 are shown and described as being constructed separately and then coupled together. In other embodiments, a needle guard and a battery isolation tab can be constructed monolithically.

Although the electronic circuit systems are shown and described herein as including a proximity sensor, in other embodiments, an electronic circuit system can include any suitable sensor for providing feedback to the electronic circuit system. For example, in some embodiments, the electronic circuit system can include a pressure sensor configured to sense the internal gas pressure within a gas-powered auto-injector. In this manner, the electronic circuit system can output an instruction and/or a status message when the internal gas pressure crosses a predetermined threshold. For example, in some embodiments, when the internal gas pressure rapidly increases, the electronic circuit system can output a message, such as, for example, "Internal gas chamber has been successfully punctured—injection is in process."

Similarly, in some embodiments, the electronic circuit system can include a temperature sensor configured to sense the temperature of the medicament contained within the medicament delivery device. In this manner, the electronic circuit system can output an instruction and/or a status message when the medicament is too cold for effective delivery. For example, in some embodiments, when the medicament is too cold for effective delivery (this may occur, for example, if the medicament delivery device has been left outside overnight), the electronic circuit system can output a message, such as, for example, "Medicament is too cold—please briskly rub the auto-injector between your hands."

Although the batteries 4962 are shown and described as having a first surface 4964 (an electrically negative terminal) and a second surface 4966 (an electrically positive terminal) opposite the first surface, in other embodiments the batteries can include a first surface and a second surface that are adjacent each other and/or co-planar. In other embodiments, an electronic circuit system can be powered by a battery having any shape and/or any number of surfaces. In yet other embodiments, an electronic circuit system can be powered by any suitable energy storage device, such as, for example, a capacitor, solar cell, spring actuated generator, or the like.

Although the medicament delivery devices have been shown and described above as being primarily single-use medical injectors, in some embodiments a medicament delivery device can include any suitable device for delivering one or more doses of a medicament into a patient's body. For example, in some embodiments, a medicament delivery device can be a pen injector containing multiple doses of a chronic-care medicament, such as, for example, insulin. In such embodiments, an electronic circuit system can output instructions associated with not only an initial use of the medicament delivery device, but also associated with repeated uses, dosage monitoring or the like. In other embodiments, a medicament delivery device can include a transdermal medicament delivery device, an inhaler or a nasal medicament delivery device.

Figure 24:
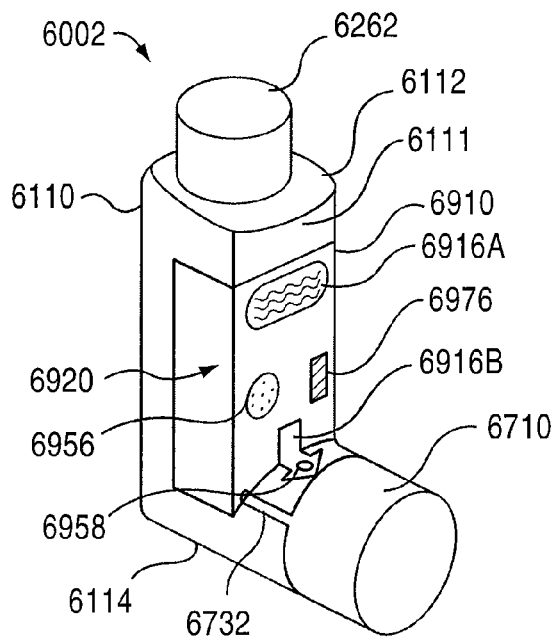
FIGS. 24 and 25 are perspective views of a medicament delivery device according to an embodiment of the invention.
Figure 25:
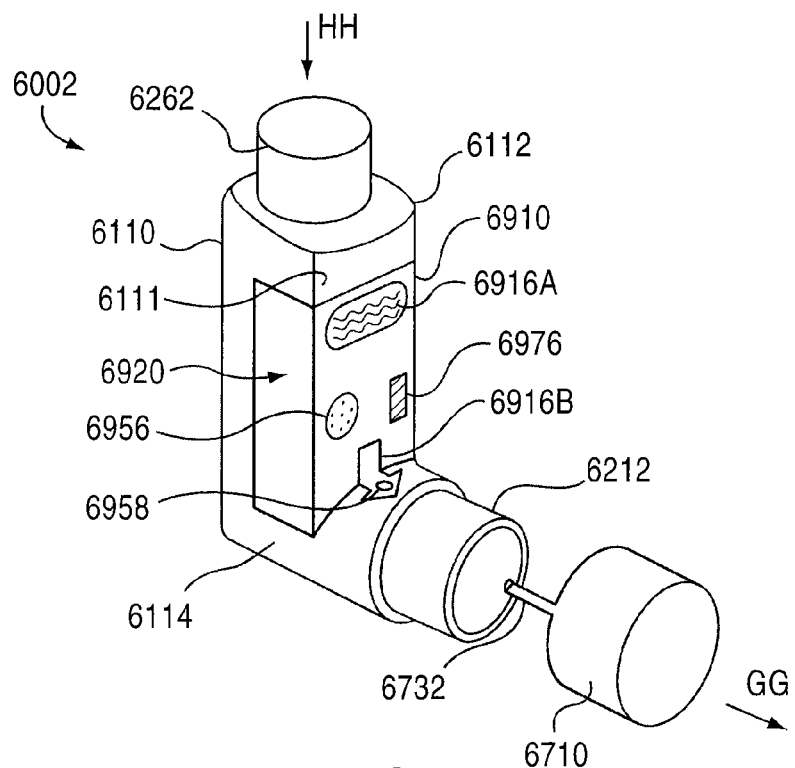

FIGS. 24 and 25 show an inhaler 6002 according to an embodiment of the invention. The inhaler 6002 includes a housing 6110 and a medicament container 6262 movably disposed within the housing 6110. The medicament container 6262 includes a metering mechanism (not shown in FIGS. 24 and 25) configured to discharge a predetermined volume of medicament when the inhaler 6002 is actuated.

The housing 6110 has a proximal end portion 6112 and a distal end portion 6114. An label 6910, which includes at least a portion of an electronic circuit system 6920, is disposed on an outer surface 6111 of the housing 6110. As described above, a portion of the label 6910 can include a textual indicia 6916. Similar to the electronic circuit systems shown and described above, the electronic circuit system 6920 is configured to output at least one electronic signal associated with the user of the inhaler 6002. The electronic circuit system 6920 includes a microprocessor (not shown), a microspeaker 6956 and an LED 6958. The electronic circuit system 6920 also includes a motion sensor 6976, the function of which is discussed in more detail below.

The distal end portion 6114 of the housing 6110 includes a mouthpiece 6212 about which a protective cap 6710 is disposed. Prior to use, the inhaler 6002 is first enabled by removing the protective cap 6710, as shown by the arrow GG in FIG. 25. The protective cap 6710 includes an actuator 6732 that actuates the electronic circuit system 6920 to trigger a predetermined output or sequence of outputs when the protective cap 6710 is removed. In some embodiments, the actuator 6732 can include a protrusion that is received by an actuation portion of the electronic circuit system 6920, in a similar manner as described above. In other embodiments, the actuator 6732 can be configured to engage a microswitch that can be repeatedly moved between a first state and a second state.

When actuated, the electronic circuit system 6920 can output one or more predetermined electronic outputs. For example, in some embodiments, the electronic circuit system 6920 can output an audible message via the microspeaker 6956 instructing the user to "vigorously shake the inhaler for five seconds." The processor can simultaneously enable the motion sensor 6976.

Upon receiving a predetermined input from the motion sensor 6976, which can be any sensor suitable for detecting the rapid motion of the inhaler 6002, the processor can then send an electronic signal to produce a second audible message. Such a message can state, for example, "the inhaler is now sufficiently shaken and is ready for use." In some embodiments, the electronic circuit system 6920 can also output an instruction associated with the correct placement of the inhaler 6002. For example, the electronic circuit system 6920 can output an audible message stating "please place the mouthpiece in your mouth and firmly press down on the medicament container." The electronic circuit system 6920 can also simultaneously output a signal to the LED 6958 to provide a visual indication of where the mouthpiece 6212 is located.

After the inhaler 6002 is enabled and placed within the mouth of the patient, the inhaler 6002 is actuated by moving the medicament container 6262 distally within housing 6110, as illustrated by arrow HH in FIG. 25. In some embodiments, the medicament container 6262 can include an actuator (not shown) that actuates the electronic circuit 6920, in a manner similar to those described above, to trigger a predetermined output or sequence of outputs. For example, in some embodiments, the processor can output an electronic signal associated with recorded speech to the microspeaker 6956. Such an electronic signal can be, for example, associated with a recorded message notifying the user that the injection is complete, instructing the user on post-injection procedures, instructing the user on post-injection medical treatment or the like. Such a status message can state, for example, "The injection is now complete."

In other embodiments, a medicament delivery device can include a transdermal medicament delivery device, such as for example, a medicament patch. In such embodiments, an electronic circuit system can be configured, for example, to output instructions associated with the enablement, placement and/or removal of the transdermal medicament delivery device. For example, in some embodiments, the electronic circuit system can be actuated by removing a protective barrier that seals the portion of the device that contacts the skin.

Figure 26:
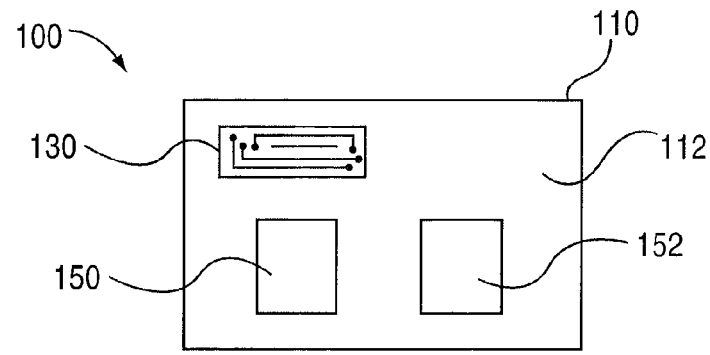
FIGS. 26-28 are schematic illustrations of a medical device according to an embodiment of the invention in a first configuration, a second configuration and a third configuration, respectively.
Figure 27:
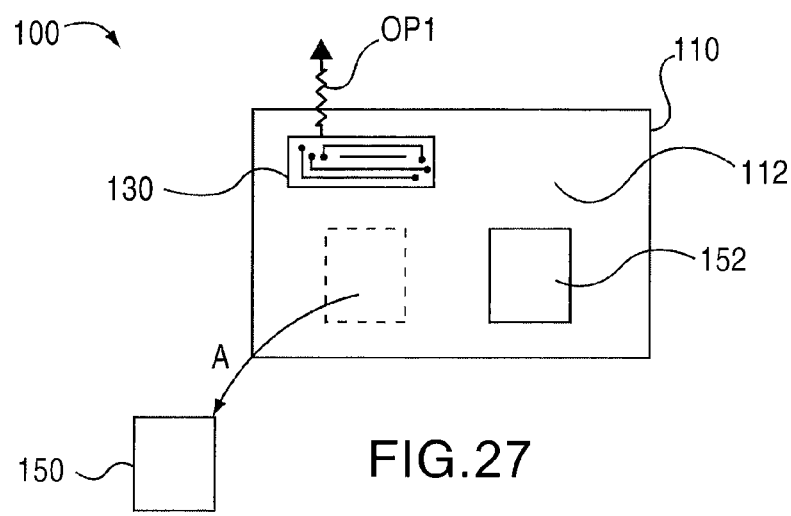
Figure 28:
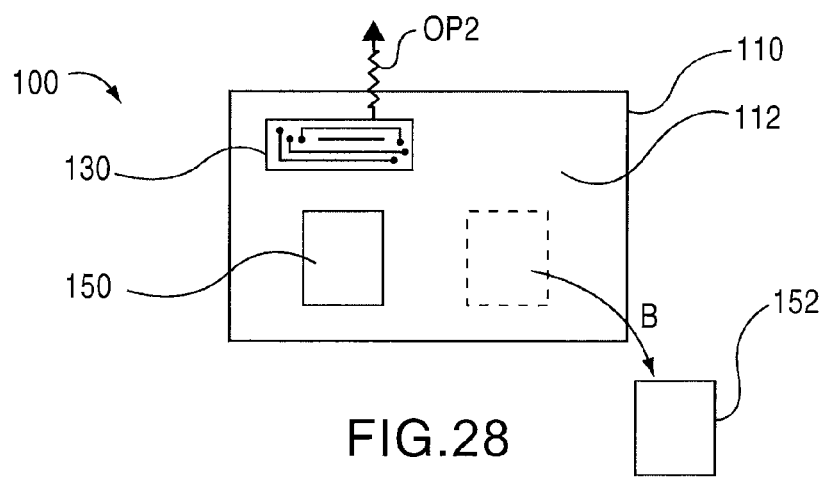

Although the medical devices are shown and described above as being medicament delivery devices, such as, for example, medical injectors, inhalers or the like, in other embodiments, a medical device can include a medicament container, such as, for example, a pill bottle, a blister pack or the like. In yet other embodiments, a medical device can include a container configured to contain one or more medicament delivery devices. For example, FIGS. 26-28 are schematic illustrations of a medical device 100 according to an embodiment of the invention in a first configuration, a second configuration and a third configuration, respectively. The medical device 100 includes a container 110 including an electronic circuit system 130 and defining an internal region 112. The internal region 112 is configured to contain one or more medicament delivery devices. Disposed within the internal region 112 are at least a first medicament delivery device 150 and a second medicament delivery device 152. The first medicament delivery device 150 and/or the second medicament delivery device 152 can be any suitable medicament delivery device, such as, for example, an auto-injector, a pen injector, an inhaler or the like.

As shown in FIG. 27, the electronic circuit system 130 is configured to output a first electronic output OP1 when the first medicament delivery device 150 is removed from the internal region 112 of the container 110, as indicated by the arrow A. As discussed in more detail herein, the first electronic output OP1 can be associated with an identification of the first medicament delivery device 150, an identification of a physical condition and/or an instruction for using the first medicament delivery device 150. Moreover, the first electronic output OP1 can include a visual output, an audible output and/or a haptic output. For example, in some embodiments, the first electronic output OP1 can be associated with an audible message instructing a user in the use of the first medicament delivery device 150. Such an audible message can state, for example, "You have removed an auto-injector containing Epinephrine. To actuate the auto-injector, first remove the red safety tab located at the end of the auto-injector." In other embodiments, for example, the first electronic output OP1 can be associated with a visual text message instructing to perform a series of tests on and/or observe the symptoms exhibited by a patient to determine whether the patient is suffering from a certain physical condition (e.g., anaphylactic shock).

Similarly, as shown in FIG. 28, the electronic circuit system 130 is configured to output a second electronic output OP2 when the second medicament delivery device 152 is removed from the internal region 112 of the container 110, as indicated by the arrow B. The second electronic output OP2, which is different than the first electronic output OP1, can include a visual output, an audible output and/or a haptic output. Moreover, as with the first electronic output OP1, the second electronic output OP2 can be associated with at least one of an identification of the second medicament delivery device 152, an identification of a physical condition and/or an instruction for using the second medicament delivery device 152. In this manner, the electronic circuit system 130 can provide the user with information about the particular medicament delivery device that has been removed from the container 110.

Although the second electronic output OP2 is described as being different than the first electronic output OP1, in some embodiments, the second electronic output OP2 can be the same as the first electronic output OP1. In some embodiments, for example, the second electronic output OP2 can include the same information as previously output via the first electronic output OP1 along with additional information. In this manner, the second electronic output OP2 can confirm the instructions and/or information provided by the first electronic output OP1.

The container 110 can be any container suitable for containing a plurality of medicament delivery devices. For example, in some embodiments, the container 110 can be a box-like structure that includes a lid or cover that can be repeatedly opened and closed to selectively expose the internal region 112 of the container 110 to an area outside the container 110. In other embodiments, the container 110 can include a frangible portion that can be irreversibly moved to expose the internal region 112 of the container 110 to allow access to the first medicament delivery device 150 and/or the second medicament delivery device 152.

The container 110 can be either portable or permanently installed at a particular location. For example, in some embodiments, the container 110 can be configured to be moved by the user. For example, in such embodiments, a user may carry the container 110 to events, such as picnics, field trips, children's camps or the like, where the likelihood of use increases. In other embodiments, the container 110 can be removably coupled to a mounting area within a building, such as a restaurant, airport and/or shopping mall. In this manner, when a user recognizes an emergency situation, the user can locate the container 110 and move it to the area in which the emergency situation is occurring. In yet other embodiments, the container 110 can be permanently coupled to a wall of a building.

The container 110 can be constructed from any suitable material, such as, for example, plastic, metal alloys, insulative foam, fabric or any combination thereof. In some embodiments, for example, the container 110 can include a hard, plastic outer casing and an insulative, shock-absorbing inner liner. In some embodiments, the container 110 can be constructed from a waterproof material and/or can be configured to float. In some embodiments, the container 110 can be constructed from a material configured to prevent light from reaching the interior region 112 of the container. In this manner, the container can prevent the medicaments contained therein from being exposed to light that can impact the chemical structure and/or stability of the medicament.

Although the container 110 is shown and described above as containing a first medicament delivery device 150 and a second medicament delivery device 152 having similar sizes and/or shapes, in some embodiments, a container can be configured to include medicament delivery devices of different sizes and/or shapes. For example, in some embodiments, a container can be configured to include a medical injector having a long, narrow shape and an inhaler having a wider shape.

Figure 29:
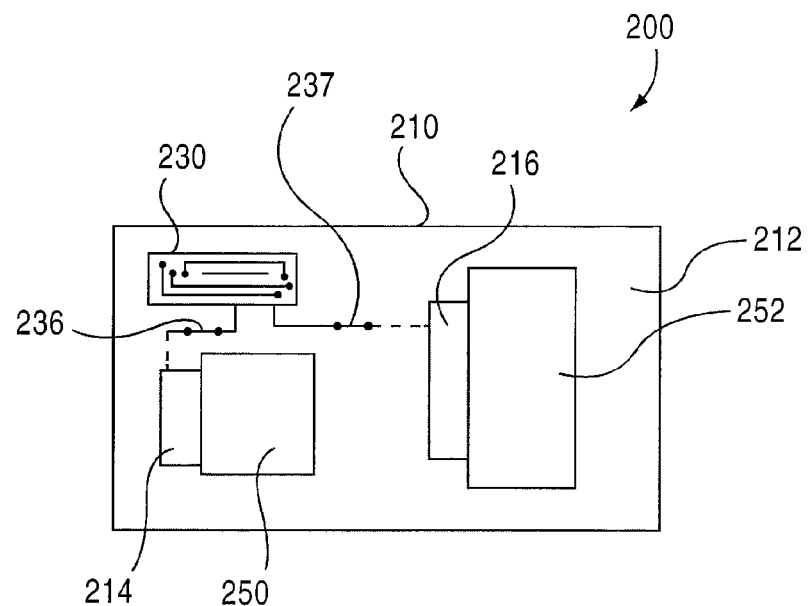
FIGS. 29-31 are schematic illustrations of a medical device according to an embodiment of the invention in a first configuration, a second configuration and a third configuration, respectively.
Figure 30:
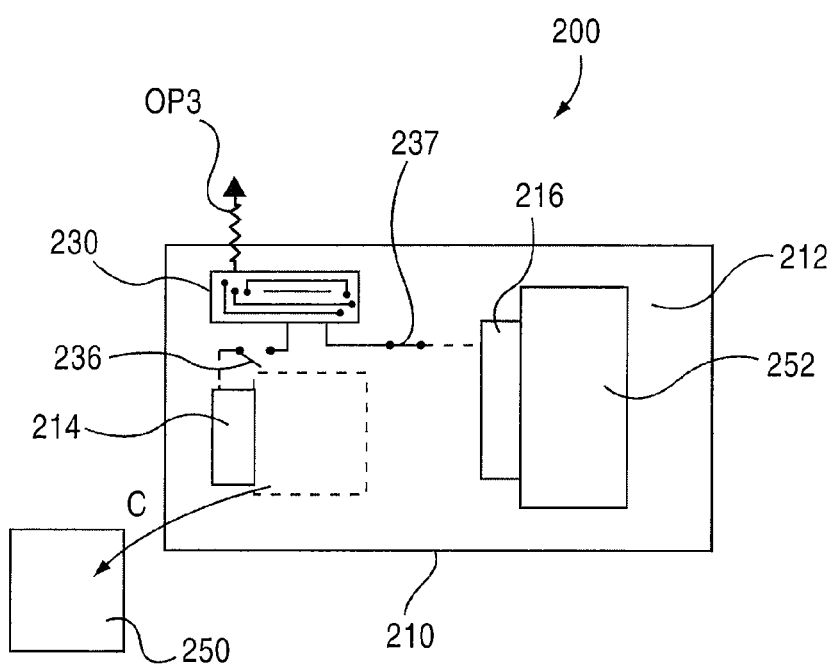
Figure 31:
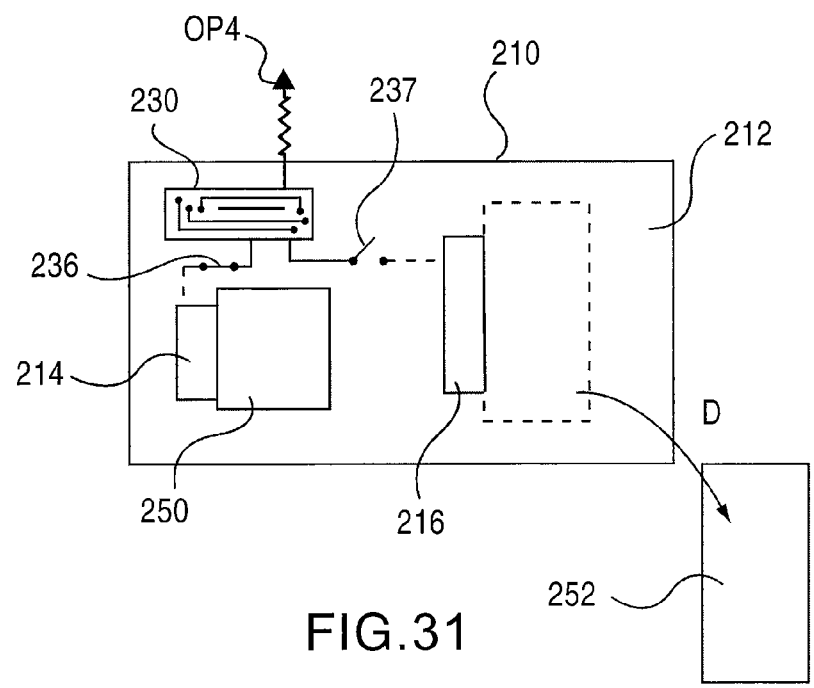

FIGS. 29-31 are schematic illustrations of a medical device 200 according to one such embodiment of the invention in a first configuration, a second configuration and a third configuration, respectively. The medical device 200 includes a container 210 including an electronic circuit system 230 and defining an internal region 212. The internal region 212 includes a first retainer 214 and a second retainer 216. The first retainer 214 retains a first medicament delivery device 250 within the internal region 212 of the container. Similarly, the second retainer 216 retains a second medicament delivery device 252 within the internal region 212 of the container.

The electronic circuit system 230 includes a first switch 236 associated with the first retainer 214 and a second switch 237 associated with the second retainer 216. The first switch 236 is configured move between a first state (e.g., closed) and a second state (e.g., opened) when the first medicament delivery device 250 is removed from the first retainer 214. Similarly, the second switch 237 is configured move between a first state and a second state when the second medicament delivery device 252 is removed from the second retainer 216. In this manner, the electronic circuit system 230 can output electronic outputs based on the state of the first switch 236 and/or the second switch 237.

More particularly, as shown in FIG. 30, the electronic circuit system 230 is configured to output a first electronic output OP3, of the type described above, when the first medicament delivery device 250 is removed from the first retainer 214, as indicated by the arrow C. Similarly, as shown in FIG. 31, the electronic circuit system 230 is configured to output a second electronic output OP4, of the type described above, when the second medicament delivery device 252 is removed from the second retainer 216, as indicated by the arrow D. Said another way, the electronic circuit system 230 is configured to output the first electronic output OP3 in response to the first switch 236 moving between its first state and its second state. Similarly, the electronic circuit system 230 is configured to output the second electronic output OP4 in response to the second switch 237 moving between its first state and its second state.

The first retainer 214 can be any structure that cooperates with the first medicament delivery device 250 to retain the first medicament delivery device 250 within the internal region 212 of the container 210. Similarly, the second retainer 216 can be any structure that cooperates with the second medicament delivery device 252 to retain the second medicament delivery device 252 within the internal region 212 of the container 210. In some embodiments, for example, the first retainer 214 can be a recessed portion (not shown in FIGS. 29-31) of the internal region 212 having a shape to receive at least a portion of the first medicament delivery device 250. Such a recess can include, for example, an edge, a contour or a ridge that forms an interference fit with a portion of the first medicament delivery device 250 when the first medicament delivery device 250 is received within the first retainer 214. In other embodiments, for example, the first retainer 214 and/or the second retainer 216 can be a clip configured to engage a portion of the first medicament delivery device 250 and/or the second medicament delivery device 252, respectively, to retain the first medicament delivery device 250 and/or the second medicament delivery device 252 in the internal region 212. In yet other embodiments, the first retainer 214 and/or the second retainer 216 can be an elastic member, such as an elastic band configured to engage a portion of the first medicament delivery device 250 and/or the second medicament delivery device 252. In yet other embodiments, the first retainer 214 and/or the second retainer 216 can include a frangible member, such as a removable plastic covering configured to retain the first medicament delivery device 250 and/or the second medicament delivery device 252 in the internal region 212.

In some embodiments, the first retainer 214 can be uniquely associated with the first medicament delivery device 250 and/or the second retainer 214 can be uniquely associated with the second medicament delivery device 252. In this manner, the first medicament delivery device 250 can only be associated with the first switch 236 and the second medicament delivery device 252 can only be associated with the second switch 237. Said another way, such an arrangement prevents second medicament delivery 252 from inadvertently being retained by the first retainer 214, which could result in the electronic circuit system 230 outputting the first electronic output OP3 when the second medicament delivery device 252 is removed from the container 210 or vice-versa. Moreover, by using the first retainer 214 and the second retainer 216, the internal region 212 can be adapted to contain a variety of different medicament delivery devices having different sizes, shapes and/or characteristics. For example, in those embodiments in which the first retainer 214 is a recessed portion of the internal region 212, the shape of the recess can be uniquely associated with a shape of the first medicament delivery device 250, thereby preventing the second medicament delivery device 252 from being received within the first retainer 214. Similarly, in some embodiments, the second retainer 216 can be a recessed portion of the internal region 212, of the type described above, having a shape to receive at least a portion of the second medicament delivery device 252.

Although the retainers are described above as cooperating with the medicament delivery devices to retain the medicament delivery devices within the internal region 212 of the container 210, in some embodiments, the first retainer 214 and/or the second retainer 216 can perform additional functions. For example, in some embodiments, the first retainer 214 can electronically couple an electronic circuit system (not shown in FIGS. 29-31) disposed on the first medicament delivery device 250 to the electronic circuit system 230. The electronic circuit system included in the first medicament delivery device 250 can be of the type shown and described above with reference FIGS. 1-25. Similarly, the second retainer 216 can electronically couple an electronic circuit system (not shown in FIGS. 29-31) disposed on the second medicament delivery device 252 to the electronic circuit system 230. In this manner, the first retainer 214 and/or the second retainer 216 can be used as a battery charging port, a data exchange port or the like.

Figure 32:
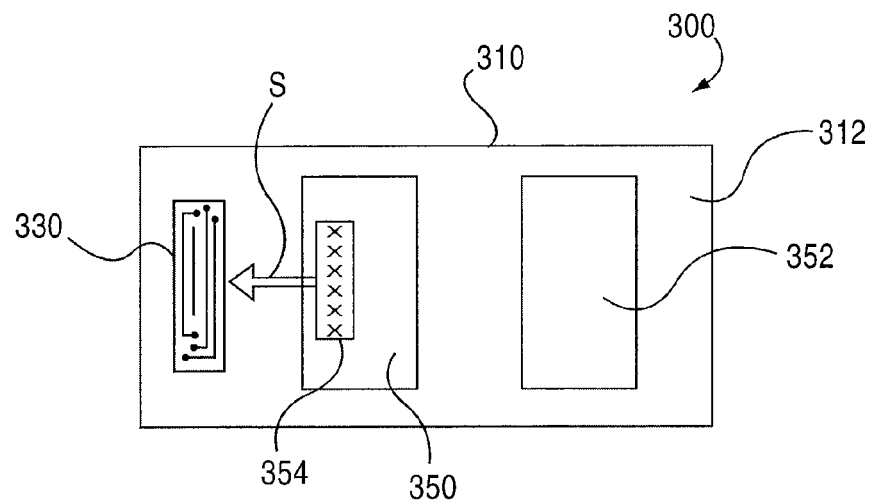
FIG. 32 is a schematic illustration of a medical device according to an embodiment of the invention.

FIG. 32 is a schematic illustration of a medical device 300 according to an embodiment of the invention. Because the medical device 300 is similar in many respects to the medical devices shown and described above, the medical device 300 is shown in only one configuration. The medical device 300 includes a container 310 including an electronic circuit system 330 and defining an internal region 312. The internal region 312 includes a first medicament delivery device 350 and a second medicament delivery device 352 of the types described above.

The electronic circuit system 330 is configured to output a first electronic output (not shown in FIG. 32), of the type described above, when the first medicament delivery device 350 is removed from the internal region 312 of the container 310. Similarly the electronic circuit system 330 is configured to output a second electronic output (not shown in FIG. 32), of the type described above, when the second medicament delivery device 352 is removed from the internal region 312 of the container 310.

Moreover, as shown in FIG. 32, the first medicament delivery device 350 includes a label 354, such as, for example, a radio frequency identification ("RFID") tag, configured to output a signal S that can be received by the electronic circuit system 330. In some embodiments, the signal S can indicate the position of the first medicament delivery device 350 (e.g., whether the first medicament delivery device 350 is outside the internal region 312). In other embodiments, the signal S can include information characterizing the first medicament delivery device 350. For example, in some embodiments, the signal S can be associated with the contents of the first medicament delivery device 350 (e.g., the amount and type of medicament contained therein), an expiration date of the first medicament delivery device 350, a dosage of the first medicament delivery device 350 and/or a use instruction associated with the first medicament delivery device 350. In this manner, the electronic circuit system 330 can receive the signal S and produce the first electronic output (not shown in FIG. 32) to include information contained within the signal S. Said another way, this arrangement allows the electronic circuit system 330 to produce an electronic output that is unique to the medicament delivery devices contained within the container 310.

In some embodiments, for example, the first electronic output can be associated with an audible message including information contained from the signal S, such as for example, the expiration date of the medicament contained within the first medicament delivery device 350. Such an audible message can state, for example, "You have removed an auto-injector containing DOSE mg of Epinephrine. The expiration date of this device is EXPIRATION DATE. If the current date is later than EXPIRATION DATE please select another auto-injector from within the container." In other embodiments, for example, the first electronic output can be a message providing the user with use instructions or other information contained within the signal S that is uniquely associated with the first medicament delivery device 350. For example, such a message can prompt a user to call a phone number unique to the manufacturer of the first medicament delivery device 350 for assistance before, during or after the use of the first medicament delivery device 350. In yet other embodiments, as described in more detail herein, the electronic circuit system 330 can automatically call such a phone number when the first medicament delivery device 350 is removed from the internal region 312 of the container 310.

The label 354 can be any device suitable for outputting the signal S that includes information associated with the first medicament delivery device 350 and that can be received by the electronic circuit system 330. For example, in some embodiments, the label 354 can include a passive RFID tag. In other embodiments, the label can include an active RFID tag.

In some embodiments, label 354 can include its own electronic circuit system, similar to the electronic circuit systems described above with reference to FIGS. 1-25. In such embodiments, the label 354 can produce multiple signals associated with the first medicament delivery device 350 based on the ongoing status of the medicament delivery device 350 as determined by the electronic circuit system included within the label 354. For example, in some embodiments, the first medicament delivery device 350 can include its own electronic circuit system having various switches, sensors or the like, such that when the user completes certain operations (e.g., removing the needle guard, removing the safety tab, etc.), a signal S can be transmitted to the electronic circuit system 330 of the container 310. The electronic circuit system 330 of the container 310 can then output one or more electronic outputs of the type described above to provide information to the user that is unique to the status of the first medicament delivery device 350.

Although the label 354 is shown and described as outputting a signal S that can be received by the electronic circuit system 330, in other embodiments, the label 354 can be a passive device that does not output an electronic signal, but rather, contains information associated with the medicament delivery device 350 in a machine-readable format. For example, in such embodiments, the label 354 can include a bar code portion containing information associated with the medicament delivery device 350. In other embodiments, the label 354 can include a magnetic strip containing information associated with the medicament delivery device 350.

Figure 33:
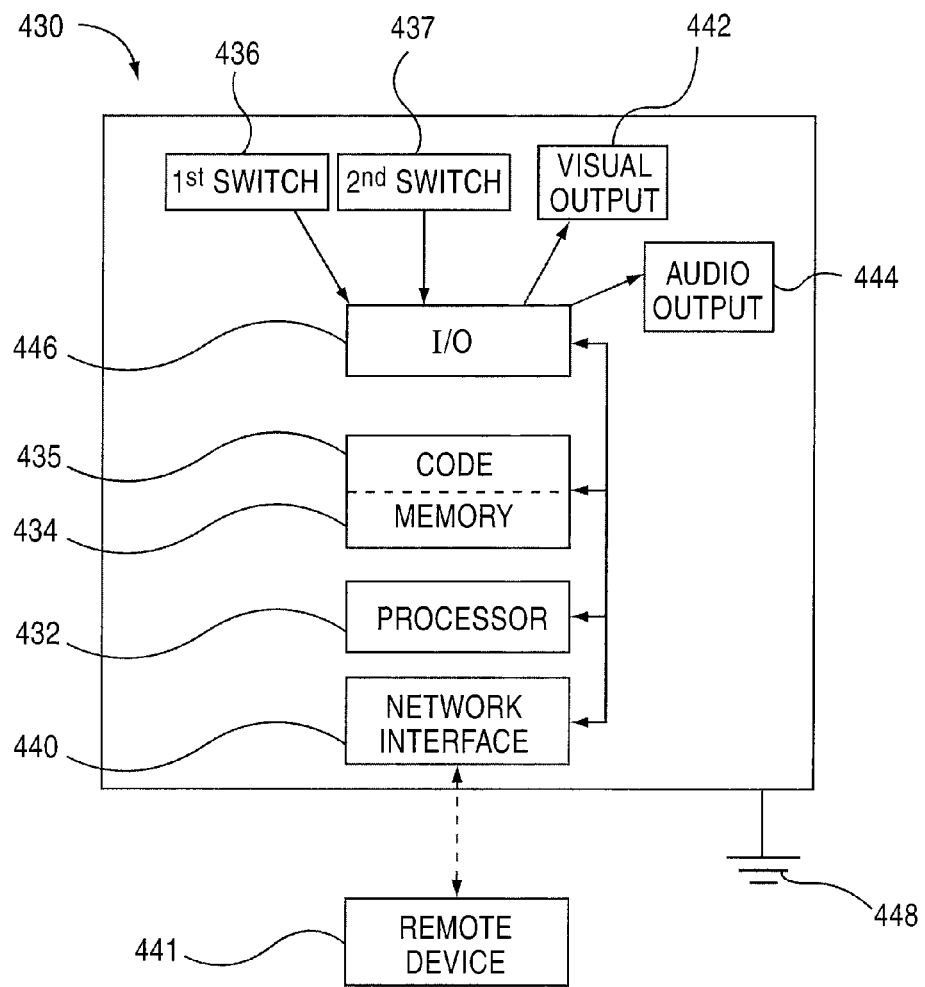
FIG. 33 is a perspective view of a medical device according to an embodiment of the invention in a first configuration.

The electronic circuit systems shown and described above can include many components operatively coupled to perform the functions described herein. For example, FIG. 33 is a schematic illustration of an electronic circuit system 430 according to an embodiment of the invention. The electronic circuit system 430 includes a processor 432 operatively coupled to a memory device 434. The memory device 434 can be configured to store processor-readable code 435 instructing the processor 432 to perform the functions described herein. In some embodiments, the processor-readable code 435 can be modified and/or updated as circumstances dictate. The electronic circuit system 430 includes an input/output device 446 configured to receive electronic inputs from a first switch 436 and/or a second switch 437. In some embodiments, the input/output device 446 can receive inputs from an RFID tag (as described above), the user's voice (e.g., through a microphone), a keyboard, a touch screen, a proximity sensor and/or any other suitable device. The input/output device 446 is also configured to provide electronic signals to various output devices, such as, for example, a visual output device 442, an audio output device 444, a haptic output device (not shown in FIG. 33) a wireless receiver (e.g., an RFID tag, a cellular phone system or the like) and/or a wired receiver (e.g., a wired network).

The visual output device 442 can be any suitable device for producing visual indicia, such as, light-emitting diodes (LEDs), liquid-crystal display (LCD) screens, optical polymers, fiber optic components or the like. Similarly, the audio output device 444 can be any suitable device for producing sound, such as a micro-speaker a piezo-electric transducer or the like. Such sound output can include, for example, an alarm, a series of beeps, recorded speech or the like.

In some embodiments, the electronic circuit system 430 includes a network interface 440 configured to operatively couple the electronic circuit system 430 to a remote device 441, either via a wired connection or via a wireless connection. The remote device 441 can be, for example, a remote communications network, a computer, a cell phone, a personal digital assistant (PDA) or the like. Such an arrangement can be used, for example, to download replacement processor-readable code 435 from a central network to the memory device 434. In some embodiments, the electronic circuit system 430 can download information associated with a medicament delivery device, such as an expiration date, a recall notice, updated use instructions or the like.

The network interface 440 can also be configured to transmit information from the electronic circuit system 430 to a central network, such as, for example, an emergency response network. In some embodiments, for example, the electronic circuit system 430 can notify an emergency responder when a medicament delivery device is removed and/or actuated. In other embodiments, the electronic circuit system 430 can transmit information to a third party, such as a physician, an emergency contact and/or the manufacturer of a medicament device, when the medicament delivery device is removed and/or actuated. Such information can include, for example, the location of use, the date and/or time of use or the like.

As shown in FIG. 33, power is supplied to the electronic circuit system 430 by a power source 448. The power source 448 can be any suitable power source, such as, for example, a DC power source and/or an AC power source. In some embodiments, for example, power can be provided to the electronic circuit system 430 by an AC circuit within the building in which the medical device is located. In other embodiments, power can be provided to the electronic circuit system 430 by one or more batteries. In yet other embodiments, power can be provided to the electronic circuit system 430 by both an AC circuit (e.g. as the primary source of power) and by batteries (e.g. as the secondary source of power). In yet other embodiments, the electronic circuit system 430 can be powered by any suitable energy storage device, such as, for example, a capacitor, solar cell or the like.

The processor 432 can be a commercially-available processing device dedicated to performing one or more specific tasks. For example, in some embodiments, the microprocessor 432 can be a commercially-available microprocessor, such as the Sonix SNC 12060 voice synthesizer. Alternatively, the processor 432 can be an application-specific integrated circuit (ASIC) or a combination of ASICs, which are designed to perform one or more specific functions. In yet other embodiments, the processor 132 can be an analog or digital circuit, or a combination of multiple circuits.

The memory device 434 can include one or more types of memory. For example, in some embodiments, the memory device 434 can include a read only memory (ROM) component and a random access memory (RAM) component. The memory device 432 can also include other types of memory suitable for storing data in a form retrievable by the processor 432, for example, electronically-programmable read only memory (EPROM), erasable electronically-programmable read only memory (EEPROM) and/or flash memory.

Although the medical devices shown and described herein include one electronic circuit system, in some embodiments, a medical device can include multiple electronic circuit systems configured to perform the functions described herein.

Figure 34:
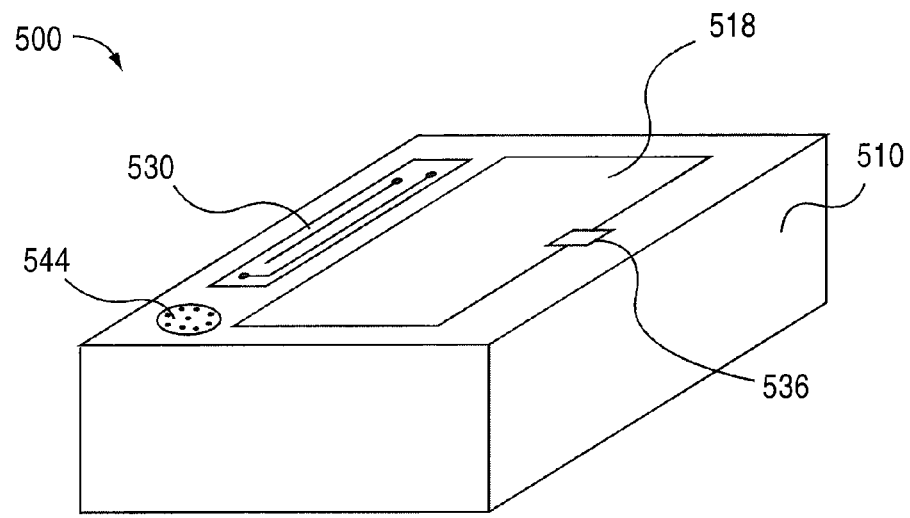
FIG. 34 is a perspective view of the medical device shown in FIG. 33 in a second configuration.
Figure 35:
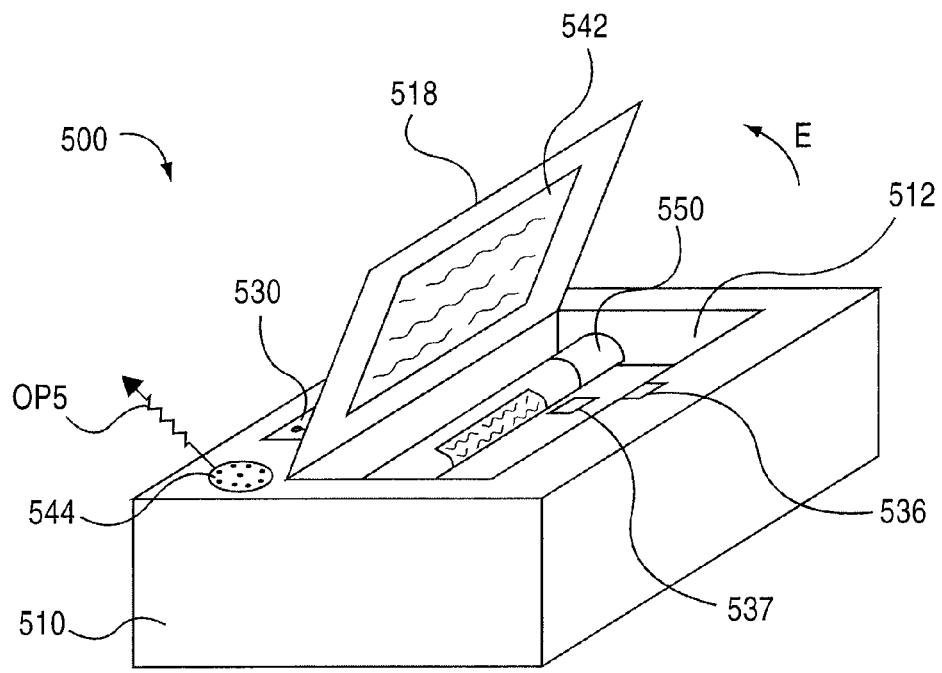
FIG. 35 is a perspective view of the medical device shown in FIG. 33 in a third configuration.
Figure 36:
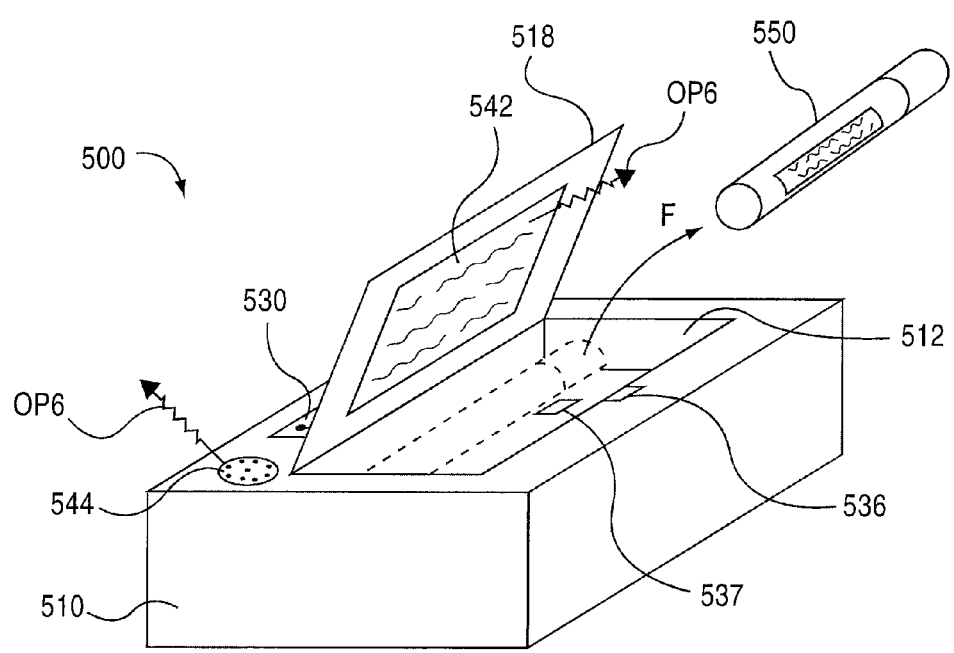
FIG. 36 is a schematic illustration of a portion of a medical device according to an embodiment of the invention.

Although the containers shown and described above include multiple medicament delivery devices, in some embodiments, a container can include only one medicament delivery device. For example, FIGS. 34-36 show a medical device 500 including a container 510 that contains a medicament delivery device 550, such as, for example a pen injector or an auto-injector. As described above, the container 510 defines an internal region 512 in which the medicament delivery device 550 is contained. The container includes an electronic circuit system 530 configured to produce one or more electronic outputs of the type described above. More particularly, the electronic circuit system 530 includes a speaker 544 and an LCD screen 542.

The container 510 also includes a movable portion 518, such as, for example, a hinged lid, that has a first position (see FIG. 34) and a second position (see FIGS. 35-36). When the movable portion 518 is in the first position, the movable portion 518 covers the internal region 512 of the container 510. Conversely, when the movable portion 518 is in the second position, at least a portion of the internal region 512 of the container 510 is exposed. Said another way, when the movable portion 518 is in the second position, the medicament delivery device 550 can be removed from the internal region 512 of the container 510.

The electronic circuit system 530 is operatively coupled to a first switch 536 and a second switch 537. The first switch 536 is configured to move between a first state (e.g., closed) and a second state (e.g., opened) when the movable portion 518 moves between its first position and its second position, as indicated by arrow E in FIG. 35. The electronic circuit system 530 is configured to output a first output OP5 via the speaker 544 when the first switch 536 is moved from its first state to its second state. The first output OP5 can be a recorded speech output associated with an identification of the medicament delivery device 550, an identification of patient symptoms (e.g., instructions for assessing the physical condition of the patient) and/or an instruction for using the medicament delivery device 550. For example, in some embodiments the first output OP5 can state "You have activated the allergic reaction response kit. This kit includes an auto-injector containing DOSE mg of Epinephrine. Before using this auto-injector, please ensure that the patient is exhibiting the following symptoms . . . " Although described as an audible output, in other embodiments, the first output OP5 can be any type of electronic output as described above.

The second switch 537 is configured to move between a first state (e.g., closed) and a second state (e.g., opened) when the medicament delivery device 550 is removed from the internal region 512 of the container 510, as indicated by the arrow F in FIG. 36. The electronic circuit system 530 is configured to output a second output OP6 via the speaker 544 and/or the LCD screen 542 when the second switch 537 is moved from its first state to its second state. The second output OP6 can be, for example, a recorded speech output and/or a video output associated with an identification of the medicament delivery device 550, an identification of patient symptoms (e.g., instructions for assessing the physical condition of the patient) and/or an instruction for using the medicament delivery device 550. For example, in some embodiments the second output OP6 can be an audio-visual output via both the speaker 544 and the LCD screen 542 providing step-by-step instructions for using the medicament delivery device 550.

Although the movable member 518 is shown and described as being a hinged lid, in some embodiments, the movable member can be coupled to the container in any suitable fashion. For example, in some embodiments, the movable member 518 can be a removable cover that is slidingly coupled to the container. In other embodiments, the movable member 518 can be a removable cover that is threadedly coupled to the container (i.e., a removable cap). In yet other embodiments, the movable member 518 can be a removable cover that is coupled to the container via an interference fit. In yet other embodiments, the movable member 518 can be a frangible cover that is irreversibly removed from the container during use of the medical device. For example, in some embodiments the movable member 518 can be a frangible cover that provides a tamperproof seal, a sanitary seal, or the like.

Figure 37:
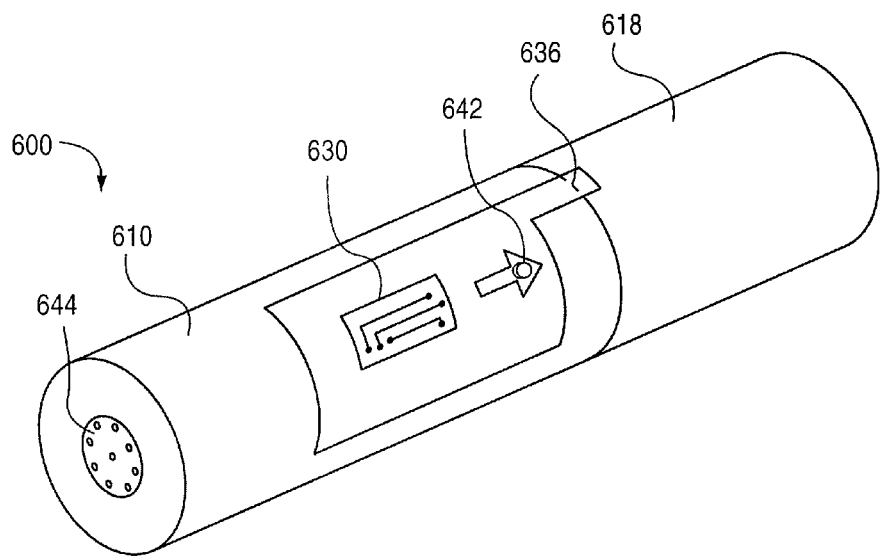
FIGS. 37-39 are schematic illustrations of a medical device according to an embodiment of the invention in a first configuration, a second configuration and a third configuration, respectively.
Figure 38:
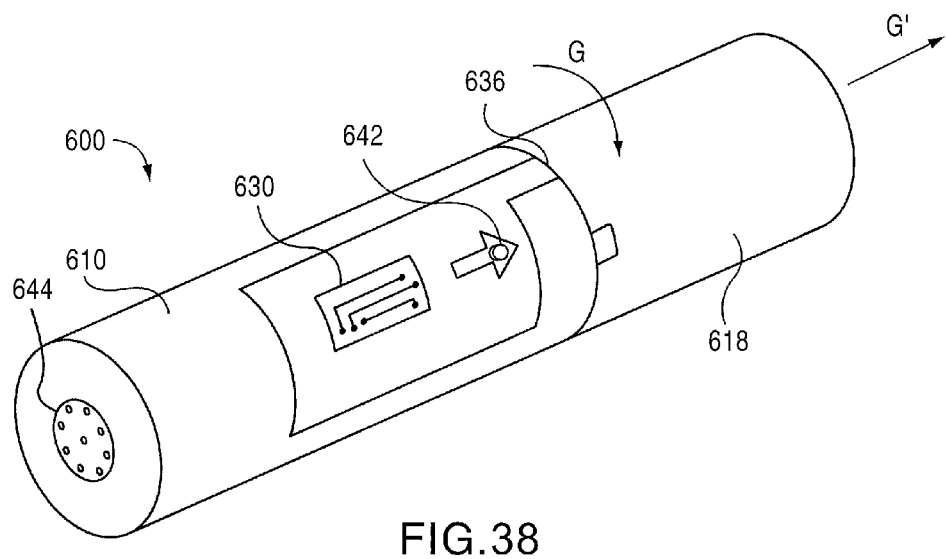
Figure 39:
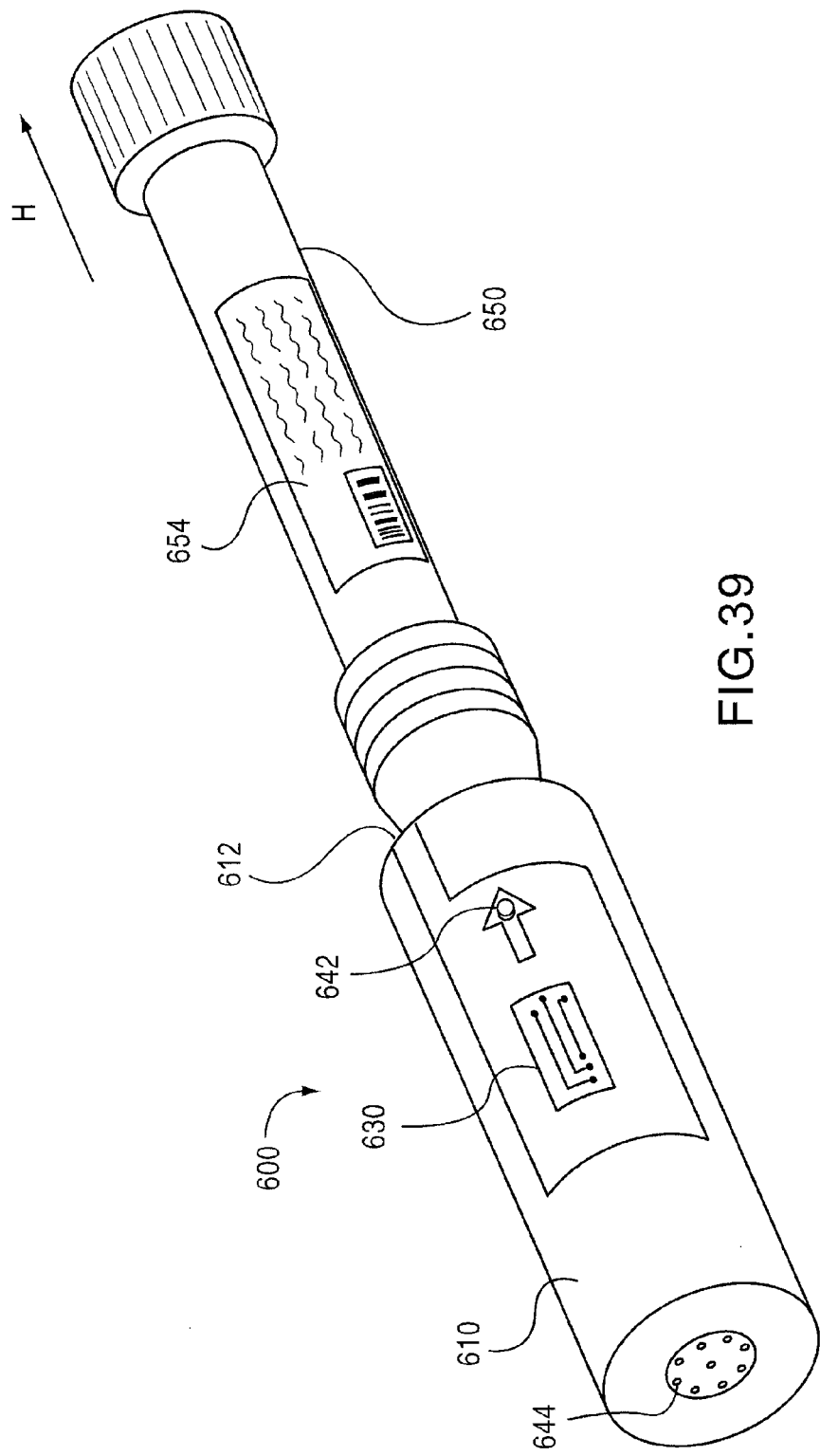

Although the containers are shown and described above as being rigid, box-like containers, in other embodiments, a container can have any suitable shape and/or flexibility. For example, in some embodiments, a container can be a flexible, pouch-like container. Such a container can be more easily carried in certain circumstances, such as, for example at outdoor events (e.g., children's camps, concerts, picnics or the like). In other embodiments, a container can be a tube configured to contain all or a portion of a medicament delivery device. For example, FIGS. 37-39 show a medical device 600 including a tube-shaped container 610 and a retainer 618. The container 610 defines an internal region 612 (see FIG. 39) in which at least a portion of a medicament delivery device 650 can be contained.

The retainer 618, which can be, for example, a mating tube-shaped lid, is movably coupled to the container 610 to retain the medicament delivery device 650 within the internal region 612. Said another way, the retainer 618 has a first position (FIG. 37) and a second position (FIG. 13). When the retainer 618 is in the first position, the retainer 618 prevents the medicament delivery device 650 from being removed from the internal region 612 of the container 610. When the retainer 618 is in the second position, the medicament delivery device 650 can be removed from the internal region 612 of the container 610.

The medical device 600 includes an electronic circuit system 630 coupled to the container 610. The electronic circuit system 630 includes a speaker 644 and a light emitting diode (LED) 642 for providing an electronic output associated with the use of the medicament delivery device 650, as described herein. In some embodiments, the electronic circuit system can be, for example, a flexible circuit included in a label coupled to an outer surface of the container 610, similar to the electronic circuit systems described above with reference to FIGS. 1-25.

The electronic circuit system 630 is configured to output a first electronic output via the LED 642 and/or the speaker 644 when the retainer 618 is moved relative to the container 610, as indicated by arrows G and/or G' in FIG. 38 As described above, the first electronic output can be associated with an identification of the medicament delivery device 650, an identification of a physical condition and/or an instruction for using the medicament delivery device 650. For example, in some embodiments, the first electronic output can be associated with an audible message instructing a user in the use of the medicament delivery device 650. Such an audible message can state, for example, "You have activated an interactive auto-injector containing DOSE mg of Epinephrine. Please remove the top of the container by twisting and pulling as indicated by the flashing arrow. After removing the top of the container, please remove the auto-injector from the container by firmly pulling on the exposed end of the auto-injector."

The electronic circuit system 630 can be prompted to output the first electronic output by a switch 636 configured to change states when the retainer 618 is moved relative to the container 610. The switch 636 can be any suitable electronic switch having at least two states. For example, in some embodiments, the switch 636 can be a single-use "tear-through" switch, as described above with reference to FIGS. 1-25. In other embodiments, a switch can be a multi-use switch, such as a microswitch.

Similarly, the electronic circuit system 630 is configured to output a second electronic output via the LED 642 and/or the speaker 644 when the medicament delivery device 650 is removed from the internal region 612 defined by the container 610, as shown by arrow H in FIG. 39. The second electronic output can be associated with an identification of the medicament delivery device 650, an identification of a physical condition and/or an instruction for using the medicament delivery device 650. For example, in some embodiments, the second electronic output can be an audible message stating, "To activate the auto-injector, first remove the needle guard. The needle guard is at the bottom of the auto-injector and contains the number one inside of an arrow pointing downward. Remove the needle guard by pulling in the direction of the arrow."

As shown in FIG. 39, the medicament delivery device 650 includes a label 654 containing information associated with the medicament delivery device 650 arranged in a machine-readable format. The electronic circuit system 630 is configured to receive (e.g., "read") the information contained in the label 654 and include at least a portion of the information in the first electronic output and/or the second electronic output. In this manner, the electronic circuit system 630 can be configured to produce an electronic output that is unique to the medicament delivery device 650 contained within the container 610. This arrangement allows the container 610 to be reused with any number of different medicament delivery devices 650. Moreover, this arrangement allows the container 610 to track the usage of a chronic-care medicament delivery devices. For example, in some embodiments, the electronic circuit system 630 can track each use of the medicament delivery device 650 and log such information on the label 654.

The label 654 can be any device suitable for containing information associated with the medicament delivery device 650 in a machine-readable format. For example, in some embodiments, the label 654 can include a bar code portion containing information associated with the medicament delivery device 650. In other embodiments, the label 654 can include a magnetic strip containing information associated with the medicament delivery device 650. In yet other embodiments, the label 654 can include a passive RFID tag containing information associated with the medicament delivery device 650. In yet other embodiments, the label 654 can include an active RFID tag containing information associated with the medicament delivery device 650.

Although the retainer 618 is shown as covering the internal region 612 defined by the container 610, in some embodiments, the retainer 618 can allow access to the internal region 612 while still retaining the medicament delivery device 650 within the internal region 612. For example, in some embodiments, the retainer 618 can be a clip, a strap or the like.

Although the medicament delivery device 650 is shown in FIGS. 37-38 as being disposed entirely within the container 610 and the retainer 618, in some embodiments, only a portion of the medicament delivery device 650 is disposed within the container 610 and/or the retainer 618. For example, in some embodiments, a container can be a sleeve configured to be disposed about a portion of a medicament delivery device, such as a chronic care pen injector. The retainer can function to retain the pen injector within the sleeve and/or to prevent the pen injector from being actuated (e.g., the retainer can act as a locking member). In use, the user can activate the electronic circuit system by depressing a start button disposed on the container. Alternatively, in some embodiments, the electronic circuit system can be activated by removing the retainer from the pen injector and/or the container. In yet other embodiments, the electronic circuit system can be activated by moving the pen injector relative to the container (i.e., twisting the pen injector within the container). Upon activation, the electronic circuit system then "reads" a label and outputs a first electronic output and/or a second electronic output, as described above.

Figure 40:
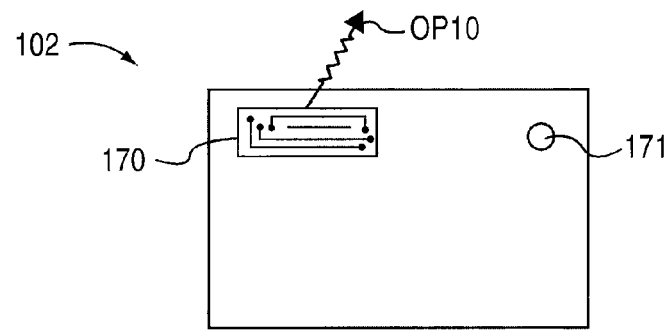
FIG. 40 is a schematic illustration of a simulated medicament delivery device according to an embodiment of the invention.

Although the medical devices are shown and described above as including medicament delivery devices, such as, for example, medical injectors, inhalers or the like, in other embodiments, a medical device can include a simulated medicament delivery device. FIG. 40 is a schematic illustration of a simulated medicament delivery device 102 according to an embodiment of the invention. In some embodiments, the simulated medicament delivery device 102 can correspond to an actual medicament delivery device (i.e., a device actually configured to deliver a medicament, not shown in FIG. 40) and can be used, for example, to train a user in the operation of the corresponding actual medicament delivery device.

The simulated medicament delivery device 102 includes an electronic circuit system 170 configured to output an electronic output OP10 associated with the use of the simulated medicament delivery device 102. As described herein, in some embodiments, for example, the electronic output OP10 can be associated with an identification of the simulated medicament delivery device 102, an identification of certain components of the simulated medicament delivery device 102 (e.g., a top portion, a safety lock, or the like), an identification of a physical condition for which a patient may require the medicament delivery device (not shown in FIG. 40) and/or an instruction for using the simulated medicament delivery device 102 and/or the corresponding actual medicament delivery device (not shown in FIG. 40).

Moreover, the electronic output OP10 can include any type of electronic output and/or signal discussed herein, such as, for example, a visual output, an audible output and/or a haptic output. For example, in some embodiments, the electronic output OP10 can be a signal associated with an audible message (e.g., recorded speech) identifying the simulated medicament delivery device 102. Such an audible message can state, for example, "You have removed an auto-injector trainer that will teach you how to use an actual auto-injector. This trainer does not contain any medicament. If this an actual emergency, please dial 911 or locate an actual auto-injector." In some embodiments, an audible output can instruct a user in the use of the simulated medicament delivery device 102. Such an audible message can state, for example, "The first step in using an actual auto-injector is to identify the key features of the auto-injector. The key features of the auto-injector are the safety lock and the actuator button . . . " In other embodiments, the electronic output OP10 can be associated with a visual indicator that identifies one or more components of the simulated medicament delivery device 102.

In some embodiments, the user can activate the electronic circuit system 170 by pushing the start button 171, which prompts the electronic circuit system 170 to output at least the electronic output OP10. In some embodiments, for example, when the start button 171 is actuated, the electronic circuit system 170 can output a predetermined sequence of electronic outputs. As described above, in some embodiments, the start button 171 can activate the electronic circuit system 170 by providing an input to a processor (not shown in FIG. 40). In other embodiments, the start button 171 can activate the electronic circuit system 170 by placing a battery (not shown in FIG. 40) in electronic communication with a portion of the electronic circuit system 170.

The simulated medicament delivery device 102 can simulate the actual medicament delivery device in any number of ways. For example, in some embodiments, the simulated medicament delivery device 102 can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device 102 can include components that correspond to the components of the actual medicament delivery device. In this manner, the simulated medicament delivery device 102 can simulate the look, feel and sounds of the actual medicament delivery device. For example, in some embodiments, the simulated medicament delivery device 102 can include external components (e.g., a housing, a needle guard, a sterile cover, a safety lock or the like) that correspond to external components of the actual medicament delivery device. In some embodiments, the simulated medicament delivery device 102 can include internal components (e.g., an actuation mechanism, a spring, a compressed gas source, a medicament container or the like) that correspond to internal components of the actual medicament delivery device.

In some embodiments, however, the simulated medicament delivery device 102 can be devoid of a medicament and/or those components that cause the medicament to be delivered (e.g., a needle, a nozzle or the like). In this manner, the simulated medicament delivery device 102 can be used to train a user in the use of the actual medicament delivery device without exposing the user to a needle and/or a medicament. Moreover, the simulated medicament delivery device 102 can have features to identify it as a training device to prevent a user from mistakenly believing that the simulated medicament delivery device 102 can be used to deliver a medicament. For example, in some embodiments, the simulated medicament delivery device 102 can be of a different color than a corresponding actual medicament delivery device. Similarly, in some embodiments, the simulated medicament delivery device 102 can include a label clearly identifying it as a training device.

The simulated medicament delivery device 102 can simulate any number of medicament delivery devices. For example, in some embodiments, the simulated medicament delivery device 102 can simulate a medical injector, such as an auto-injector, a pen injector or the like. In other embodiments, the simulated medicament delivery device 102 can simulate an inhaler. In yet other embodiments, the simulated medicament delivery device 102 can simulate a transdermal delivery device.

In some embodiments, the simulated medicament delivery device 102 can repeatedly simulate the actual medicament delivery device. For example, in some embodiments, after the simulation is complete the electronic circuit system can be reset, for example, by pushing the start button 171. In this manner, the simulated medicament delivery device 102 can be configured to repeat the electronic output OP10 or predetermined sequence of electronic outputs during subsequent simulations.

Figure 41:
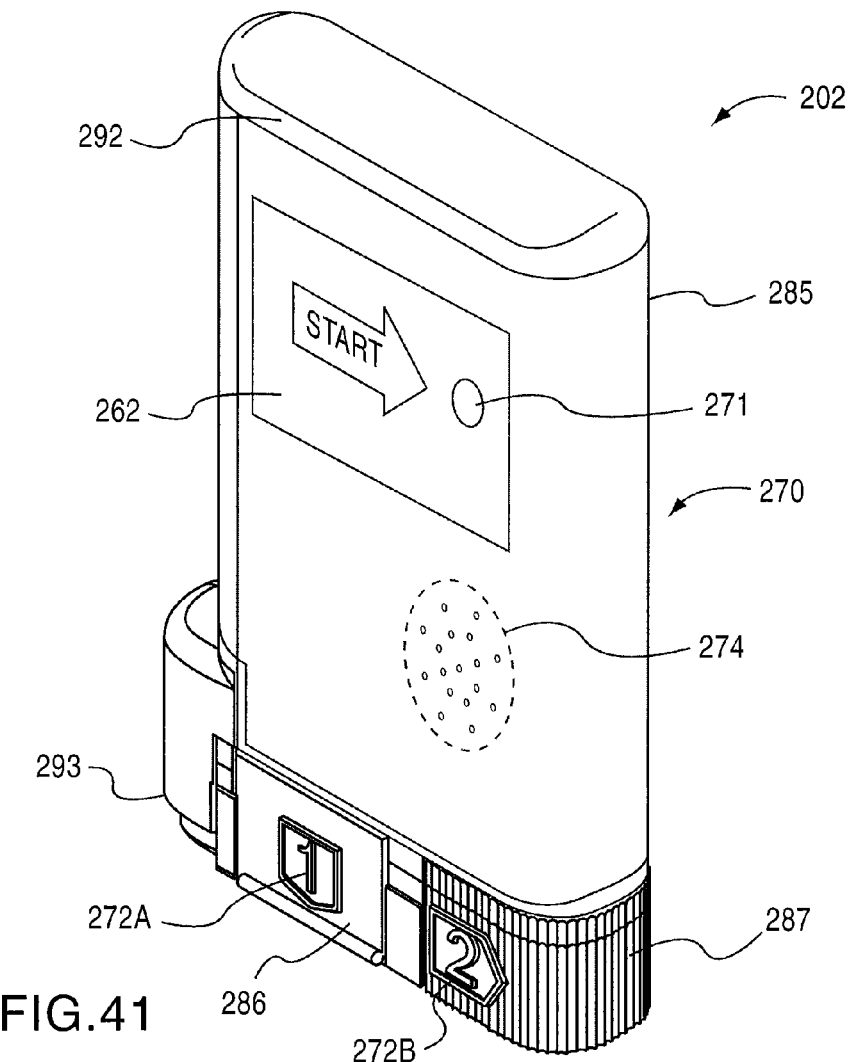
FIG. 41 is a perspective view of a simulated auto-injector according to an embodiment of the invention.
Figure 42:
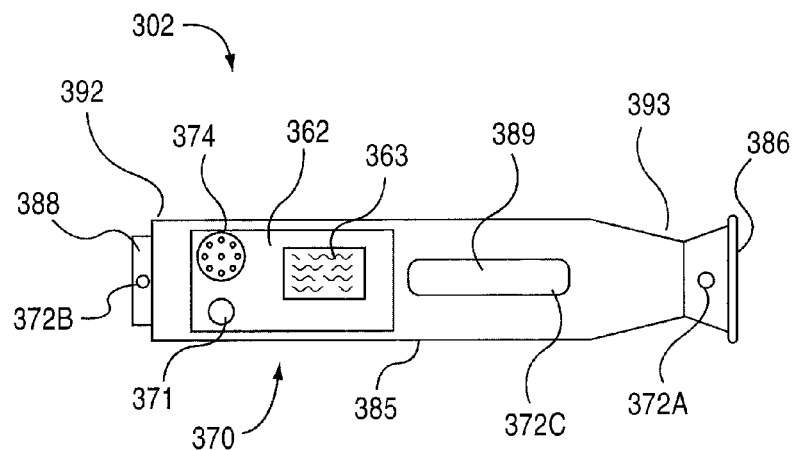
FIGS. 42-46 are front are front views of a simulated auto-injector according to an embodiment of the invention, in a first configuration, second configuration, third configuration, fourth configuration and fifth configuration, respectively.

FIG. 41 is a perspective view of a simulated auto-injector 202 according to an embodiment of the invention. The simulated auto-injector 202 is configured to simulate an auto-injector (not shown in FIG. 41) similar to the auto-injectors described herein and in U.S. patent application Ser. No. 11/562,061, entitled "Devices, Systems and Methods for Medicament Delivery," filed Nov. 21, 2006, which is incorporated herein by reference in its entirety.

The simulated auto-injector 202 includes a housing 285 having a proximal end portion 292 and a distal end portion 293. A simulated needle guard assembly 286 is removably coupled to the distal end portion 293 of the housing 285. The simulated needle guard assembly 286 is configured to simulate an actual needle guard assembly (e.g., needle guard assembly 4810 shown and described above with reference to FIGS. 5, 12-14). Similarly, a simulated safety lock 287 is removably coupled to the distal end portion 293 of the housing 285. The simulated safety lock 287 is configured to simulate an actual safety lock (e.g., safety lock 4710 shown and described above with reference to FIGS. 5, 12-14).

The simulated auto-injector 202 includes an electronic circuit system 270 and a label 262. The label 262 can be any suitable label of the type described herein. In some embodiments, for example, the label 262 can include at least a portion of the electronic circuit system 270 (i.e., portions of an electronic conductors, portions of a printed circuit board, a battery, an LED or the like). In other embodiments, the label 262 can be devoid of any portion of the electronic circuit system 270.

The electronic circuit system 270 includes a start button 271, a speaker 274 and two LEDs 272A, 272B. The electronic circuit system 270 can be any electronic circuit system of the type shown and described herein. For example, in some embodiments, the electronic circuit system 270 can include a flexible printed circuit board to electronically coupled the components contained therein. Moreover, the electronic circuit system 270 can be disposed in any suitable manner relative to the housing 285. In some embodiments, for example, the electronic circuit system 270 can be integrated with the simulated medicament delivery device 202. Said another way, in some embodiments, the electronic circuit system 270 can be contained within the housing 285 and/or the electronic circuit system 270 can be assembled concurrently and/or using common processes with the simulated medicament delivery device 202. In other embodiments, the electronic circuit system 270 can be partially-integrated with the simulated medicament delivery device 202. Said another way, in some embodiments, at least a portion of the electronic circuit system 270 can be contained within the housing 285 and/or at least a portion of the electronic circuit system 270 can be assembled concurrently and/or using common processes with the simulated medicament delivery device 202. In yet other embodiments, the electronic circuit system 270 can be disposed entirely on an outer surface of the housing 285 and/or the electronic circuit system 270 can be assembled using separate processes from those used to manufacture the simulated medicament delivery device 202. In some embodiments, for example, the electronic circuit system can be included in the label 262. In other embodiments, the label 262 can be used to secure the electronic circuit system to an outer portion of the housing 285.

To activate the electronic circuit system 270, the user first pushes the start button 271. As described above, when actuated, the electronic circuit system 270 can output one or more electronic outputs. For example, in some embodiments, an electronic output can be associated with an audio and/or a visual output used to describe the features of and/or identify component of the simulated medicament delivery device 202. For example, in some embodiments, the first LED 272A, the output of which is shaped as the numeral "1," can output a flashing light of a first color while the speaker 274 simultaneously outputs a recorded voice message stating "the simulated needle guard is identified by the FIRST COLOR flashing light shaped as the numeral one." Similarly, the second LED 272BA, the output of which is shaped as the numeral "2," can output a flashing light of a second color different than the first color while the speaker 274 simultaneously outputs a recorded voice message stating "the simulated safety lock is identified by the SECOND COLOR flashing light shaped as the numeral two." In this manner, the electronic circuit system 270 can provide both audible and visual instructions to assist the user in the operation of the simulated medicament delivery device 202.

In some embodiments, the electronic circuit system 270 can output at least one electronic output in response to a switch (not shown in FIG. 41) being moved between a first state and a second state. For example, similar to the needle guard assembly 4810 shown and described above with reference to FIG. 12, the simulated needle guard assembly 286 can include an actuator configured to actuate a switch contained within the electronic circuit system 270. The switch can be any suitable switch of the types shown and described above.

For example, in some embodiments, a switch can be a "tear-through" switch configured to move irreversibly from a first state to a second state. In other embodiments, a switch can be a microswitch configured to repeatedly move between a first state and a second state. In this manner, the electronic circuit system 270 can output instructions when the user moves the simulated needle guard assembly 286 relative to the housing 285. Such instructions can state, for example, "You have now removed the needle guard assembly. The next step is to remove the safety lock. Please pull the safety lock as indicated by the flashing arrow." In a similar manner, the simulated safety lock 287 can include an actuator configured to actuate a switch contained within the electronic circuit system.

Although the simulated medicament delivery device 202 is shown as including a start button 271 to activate the electronic circuit system (not shown in FIG. 41), in other embodiments, an electronic circuit system 270 can be activated by any suitable means. For example, in some embodiments, the electronic circuit system can be activated by removing the simulated needle guard assembly 286, as described above with reference to FIG. 12. In other embodiments, the electronic circuit system 270 can be activated by removing the simulated safety lock 287, as described above with reference to FIG. 13. In yet other embodiments, the electronic circuit system 270 can be activated by removing the simulated medicament delivery device 202 from a container (not shown in FIG. 41), as shown and described above with reference to FIGS. 26-39.

FIGS. 42-46 are front views of a simulated auto-injector 302 according to an embodiment of the invention. The simulated auto-injector 302 includes a housing 385 having a proximal end portion 392 and a distal end portion 393. The housing defines a window 389, which can, for example, simulate a status window of a corresponding actual auto-injector (not shown in FIGS. 42-46), as described below. A simulated needle guard assembly 386 is removably coupled to the distal end portion 393 of the housing 385. Similarly, a simulated safety lock 387 is disposed at the distal end portion 393 of the housing (see FIG. 43). The proximal end portion 392 of the housing 385 includes a simulated injector actuation button 388. The simulated injector actuation button 388 is configured to simulate an actuation button of the corresponding auto-injector.

The simulated auto-injector 302 includes an electronic circuit system 370 and a label 362. The label 362 can include a textual indicia 363 and can be any suitable label of the type described herein. In some embodiments, for example, the label 362 can include at least a portion of the electronic circuit system 370 (i.e., portions of an electronic conductor, portions of a printed circuit board, a battery, an LED or the like). In other embodiments, the label 362 can be devoid of any portion of the electronic circuit system 370.

The electronic circuit system 370 includes a start button 371, a speaker 374 and three visual output devices 372A, 372B and 372C. The visual output devices 372A, 372B and 372C can be, for example, LEDs, LCDs, organic polymer devices and/or fiber optic devices. The electronic circuit system 370 also includes a force sensor 377 (shown in FIG. 43) and a position sensor (not shown in FIGS. 42-46). The above described components can be electronically coupled together by any suitable mechanism, such as, for example a printed circuit board of the types shown and described herein.

As described above, to activate the electronic circuit system 370, the user pushes the start button 371. When actuated, the electronic circuit system 370 can output one or more electronic outputs. For example, in some embodiments, the first visual output device 372A can output a flashing light while the speaker 374 simultaneously outputs a recorded voice message stating "Please remove the simulated needle guard, which is at the end of the injector as indicated by the flashing light."

Figure 43:
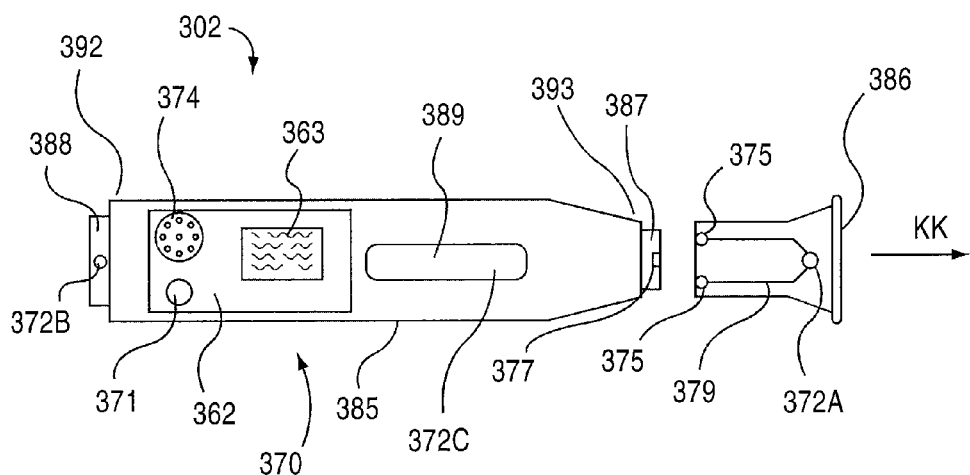

As illustrated by arrow KK in FIG. 43, the simulated needle guard 386 is removed by moving it along the longitudinal axis of the housing 385. When the simulated needle guard 386 is removed, the portion of the electronic circuit system 370 that includes the first visual output device 372A is no longer electronically coupled to the remainder of the electronic circuit system 370. Accordingly, the first visual output device 372A becomes deactivated when the simulated needle guard 386 is removed. Moreover, the terminals 375 of the electronic conductors 379 can form a portion of a switch, such that when the simulated needle guard 386 is removed, the switch changes from a first state to a second state, thereby prompting the electronic circuit system 370 to output an additional electronic output. For example, in some embodiments, the speaker 374 can output a recorded voice message stating "Please place the simulated auto-injector against your thigh. Do not tilt the simulated auto-injector. When in the proper position, please press firmly against the thigh before actuating the auto-injector."

In addition to prompting the electronic circuit system 370 to output additional visual and/or audible outputs, the removal of the simulated needle guard 386 can also activate the position sensor (not shown in FIGS. 42-46). The position sensor can be any suitable sensor for sensing a position, location and/or orientation of the simulated auto-injector 302. For example, in some embodiments, the position sensor can be configured to sense the angle Θ between the longitudinal axis of the housing 385 and the surface of the target T (see FIG. 44). In other embodiments, the position sensor can be configured to sense the absolute angle of the longitudinal axis of the housing based on gravity. In yet other embodiments, the position sensor can be capacitance sensor, a temperature sensor, an optical sensor or any other suitable sensor for determining when the distal end 393 of the simulated medicament delivery device 302 is in contact with the target T. In this manner, the position sensor can provide feedback to the user to ensure that the simulated medicament delivery device 302 is correctly positioned relative to the target T.

Figure 44:
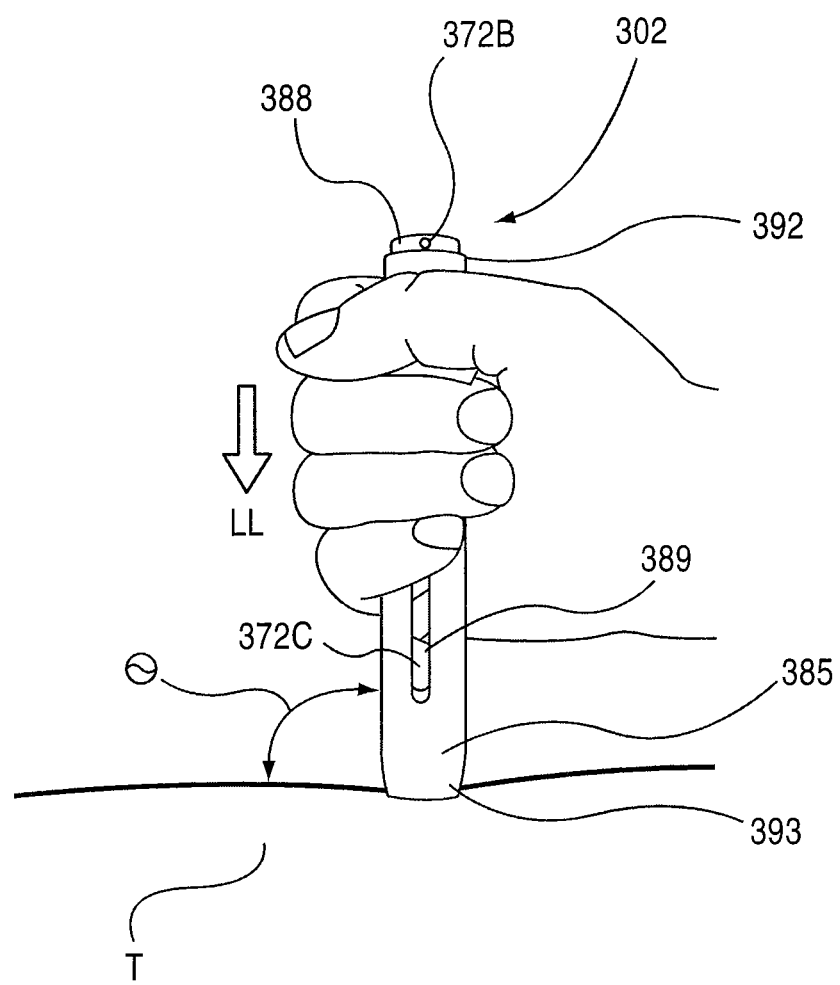
Figure 45:
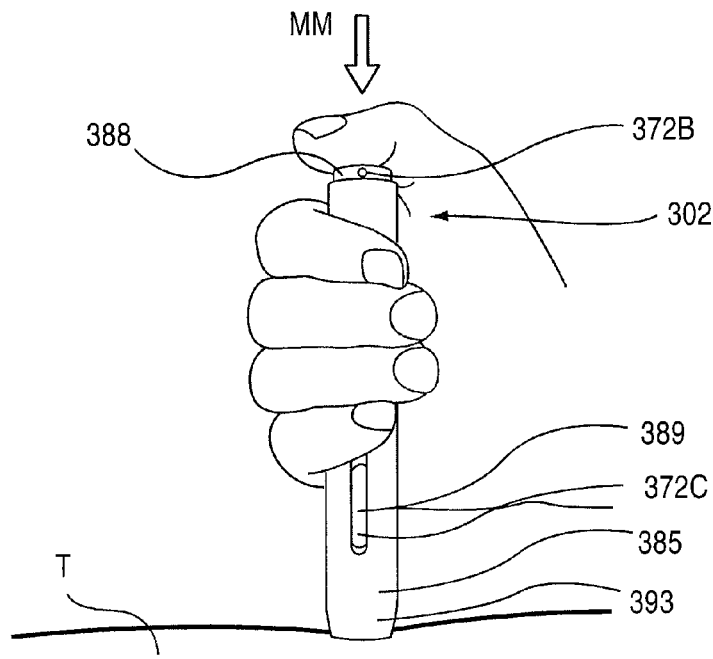

Similarly, when the user presses the simulated medicament delivery device 302 against the target T, as shown by the arrow LL in FIG. 44, the force sensor 377 can sense the force and/or pressure between the target T and the simulated safety lock 387. In this manner, the force sensor 377 can provide feedback to the user to ensure that the simulated medicament delivery device 302 is pressed against the target T with sufficient force to move the safety lock of an actual medicament delivery device (not shown in FIGS. 42-46). The force sensor 377 can also provide feedback to the user to ensure that the simulated medicament delivery device 302 is not pressed too firmly against the target T. The force sensor 377 can be any sensor suitable for sensing a force and/or pressure, such as for example, a strain-gauge load sensor, a piezo-electric sensor or the like.

In some embodiments, after the simulated medicament delivery device 302 is correctly positioned with sufficient force against the target T, the force sensor 377 can prompt the electronic circuit system 370 to output an additional electronic output or sequence of electronic outputs. For example, in some embodiments, the second visual output device 372B can output a flashing light while the speaker 374 simultaneously outputs a recorded voice message stating "The simulated auto-injector is now correctly positioned against your body. Please press the injector actuation button at the top of the auto-injector as indicated by the flashing light."

In some embodiments, the electronic circuit system 370 can include a timer (not shown in FIGS. 42-46) to determine the duration of any of the various operations discussed herein. In this manner, the electronic circuit system 370 can repeat a previous electronic output if no action has been sensed within a predetermined amount of time. For example, in some embodiments, the electronic circuit system 370 can repeat the electronic output prompting the user to remove the simulated needle guard 386 if a predetermined time period has elapsed after the start button 371 is pushed and before the simulated needle guard 386 is removed. In some embodiments, the electronic circuit system 370 can augment the electronic output prompting the user to remove the simulated needle guard 386 if a predetermined time period has elapsed after the start button 371 is pushed and before the simulated needle guard 386 is removed. The electronic output can be augmented, for example, by automatically increasing the volume of the audible output, changing the characteristics (e.g., the color, flash rate or the like) of the visual outputs or the like.

In other embodiments, the electronic circuit system 370 can output an electronic output to instruct the user to move to the next operation after a predetermined amount of time has elapsed. For example, in some embodiments, the speaker 374 can output a recorded voice message stating "Release the actuation button. Do not continue to hold the actuation button down" when the duration between when the user presses the simulated injector actuation button 388 (as shown by arrow MM in FIG. 45) and when the user releases the simulated injector actuation button 388 (as shown by arrow NN in FIG. 46) exceeds a predetermined duration. In this manner, the electronic circuit system 370 can provide feedback to the user to ensure that the simulated medicament delivery device 302 is used properly.

Figure 46:
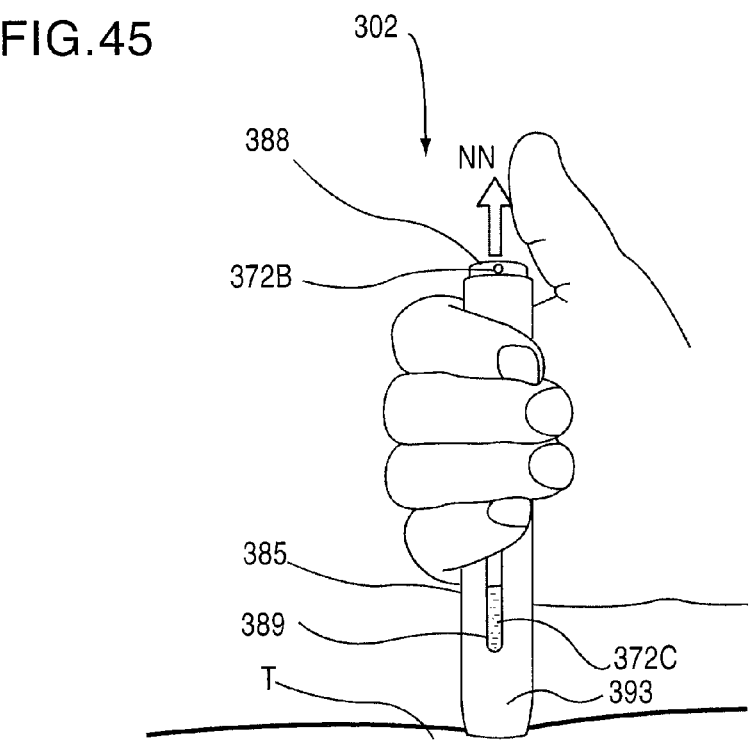

As shown in FIG. 46, the third visual output device 372C is visible through the window 389 defined by the housing 385. In some embodiments, the third visual output device 372C and the window 389 can collectively simulate a status window of the actual medicament delivery device (not shown in FIG. 46). For example, in some embodiments, the third visual output device 372C can gradually change color to simulate an associated color change of a status window that alerts a user when an actual injection is complete.

Although the simulated medicament delivery devices are shown and described as including external components and/or internal components to simulate actual medicament delivery devices, in some embodiments, a simulated medicament delivery device can be devoid of certain components, such as, for example, springs, actuation mechanisms or the like. For example, in some embodiments, a simulated medicament delivery device can include an electronic circuit system configured to output an electronic output to simulate any one of a tactile sensation, an audible sensation, a visual sensation, an olfactory sensation and/or a taste sensation associated with a use of the medicament delivery device. In this manner, the simulated medicament delivery device can simulate a medicament delivery device without mechanical components and/or medicament, which can be make the simulated medicament delivery device expensive, unsafe to use, difficult to use, difficult to reset for repeated use or the like.

Figure 47:
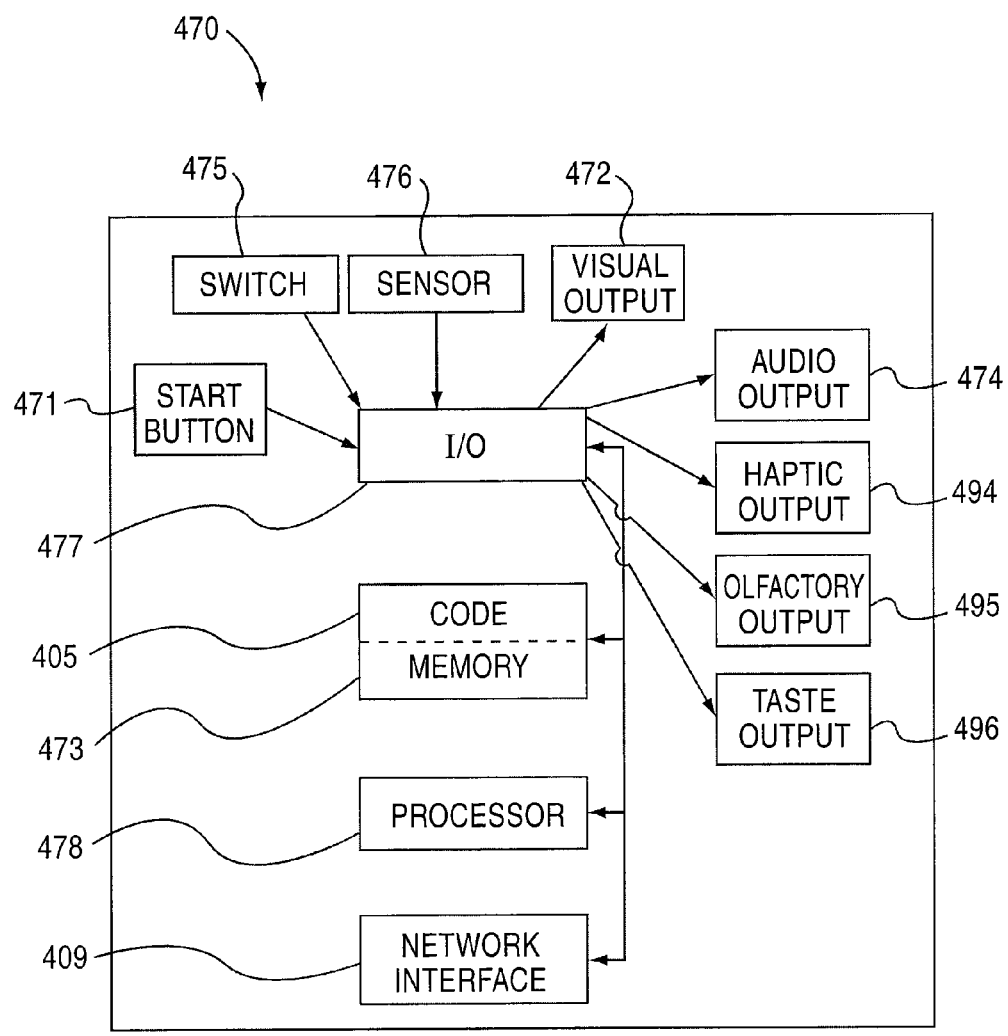
FIG. 47 is a schematic illustration of a medical device according to an embodiment of the invention.

FIG. 47 is a schematic illustration of an electronic circuit system 470 according to an embodiment of the invention configured to cooperate with a housing (not shown in FIG. 47) to simulate a medicament delivery device (not shown in FIG. 47). The electronic circuit system 470 includes a processor 478 operatively coupled to a memory device 473, of the types shown and described above with reference to FIGS. 3 and 33. The memory device 473 can be configured to store processor-readable code 405 instructing the processor 478 to perform the functions described herein. In some embodiments, the processor-readable code 405 can be modified and/or updated as circumstances dictate.

The electronic circuit system 470 includes an input/output device 477 configured to receive electronic inputs from a switch 475 and/or a sensor 476, as described above. In some embodiments, the input/output device 477 can receive inputs from any suitable device, such as an RFID tag (as described above), the user's voice (e.g., through a microphone), a start button 471 or the like. The input/output device 477 is also configured to output electronic signals to various output devices, such as, for example, a visual output device 472, an audio output device 474, a haptic output device 494, an olfactory output device 495, a taste output device 496, a wireless receiver (e.g., an RFID tag, a cellular phone system or the like) and/or a wired receiver (e.g., a wired network).

The visual output device 472 can be any suitable device for producing visual indicia, such as, light-emitting diodes (LEDs), liquid-crystal display (LCD) screens, optical polymers, fiber optic components or the like. In this manner, the electronic circuit system 470 can simulate a particular visual feature of a medicament delivery device, such as, for example, a change in the color of a status window.

Similarly, the audio output device 474 can be any suitable device for producing sound, such as a micro-speaker, a piezo-electric transducer or the like. Such audible output can include, for example, an alarm, a series of beeps, recorded speech or the like. In this manner, the electronic circuit system 470 can simulate a particular audible feature of a medicament delivery device, such as, for example, a series of clicks associated with the actuation of the medicament delivery device and/or the delivery of the medicament.

The haptic output device 494 can be any suitable device for producing a haptic output, such as a vibrator, a piezo-electric device, a heater, a cooler or the like. In this manner, the electronic circuit system 470 can simulate a particular feel of a medicament delivery device. For example, in some embodiments, a simulated medicament delivery device can be configured to simulate a transdermal medicament delivery device by simulating the thermal feel of a medicament delivery area against the skin. In other embodiments, a simulated medicament delivery device can be configured to simulate an auto-injector by simulating the vibration associated with the actuation of the auto-injector.

The olfactory output device 495 can be any suitable device for producing a scent output. In this manner, the electronic circuit system 470 can simulate a particular smell associated with a medicament delivery device. For example, in some embodiments, a simulated medicament delivery device can be configured to simulate an inhaler by simulating the smell of a medicament as it is being delivered orally.

Similarly, the taste output device 495 can be any suitable device for producing a simulated taste. In this manner, the electronic circuit system 470 can simulate a particular taste associated with a medicament delivery device. For example, in some embodiments, a simulated medicament delivery device can be configured to simulate an inhaler by simulating the taste of a medicament as it is being delivered orally.

In some embodiments, the electronic circuit system 470 can include a network interface 409 configured to operatively couple the electronic circuit system 470 to a remote device (not shown in FIG. 47), as described above. The network interface 409 can also be configured to transmit information from the electronic circuit system 470 to a central network, such as, for example, a doctor's office, as described above.

Figure 48:
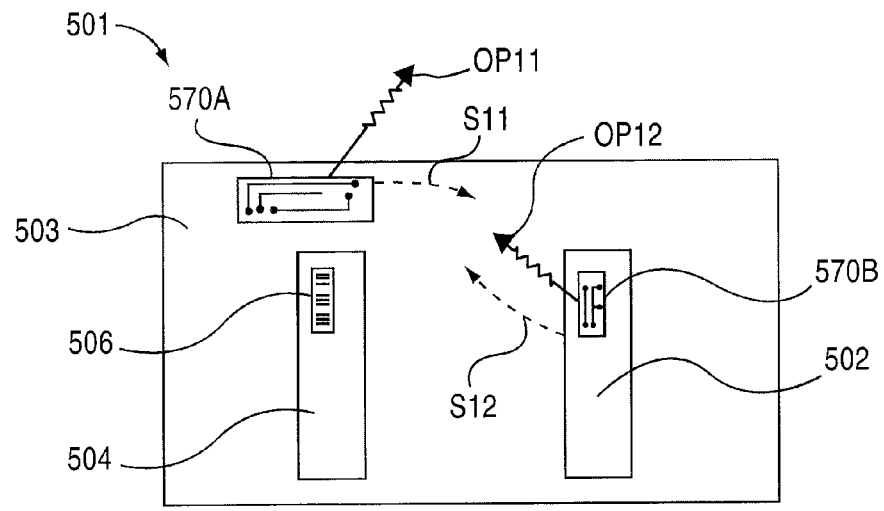
FIG. 48 is a schematic illustration of a medical device according to an embodiment of the invention.

In some embodiments, a simulated medicament delivery device can be included in a kit. FIG. 48 is a schematic illustration of a medical device 501 according to an embodiment of the invention. The medical device 501 includes a container 503, a medicament delivery device 504 and a simulated medicament delivery device 502. The container 503, which includes a first electronic circuit system 570A, can be similar to the containers shown and described above with reference to FIGS. 26-39. The medicament delivery device 502, which includes a label 506 can be similar to the medicament delivery devices shown and described herein. Similarly, the simulated medicament delivery device 502, which includes a second electronic circuit system 570B, can be similar to the simulated medicament delivery devices shown and described above with reference to FIGS. 40-47.

The first electronic circuit system 570A can output an electronic output OP11, of the type described above, when a user presses a start button (not shown in FIG. 48), when the container 503 is opened, when the medicament delivery device 504 is removed from the container and/or when the simulated medicament delivery device 502 is removed from the container. Moreover, the label 506 can contain information associated with the medicament delivery device 504 in a machine-readable format. Accordingly, the first electronic circuit system 570A can receive (e.g., "read") the information contained in the label 506 and include at least a portion of the information in the electronic output OP11. In this manner, as described above, the first electronic circuit system 570A can be configured to produce an electronic output OP11 that is unique to the medicament delivery device 504 contained within the container 503. For example, in some embodiments, the electronic output OP11 can notify a user when the medicament delivery device 504 has been removed from the container 503 and alert the user to the presence of the simulated medicament delivery device 502.

Similarly, the second electronic circuit system 570B can output an electronic output OP12, of the type described above, when a user presses a start button (not shown in FIG. 48), when the simulated medicament delivery device 502 is removed from the container 503 or the like. Moreover, similar to the function of the first electronic circuit system 570A, the second electronic circuit system 570B can also receive (e.g., "read") the information contained in the label 506 and include at least a portion of the information in the electronic output OP12. For example, in some embodiments, the electronic output OP11 can notify a user of a status (e.g., the dosage, expiration date or the like) of the medicament delivery device 504.

In some embodiments, the second electronic circuit system 570B can output a signal S12 that can be received by the first electronic circuit system 570A. In some embodiments, the signal S12 can indicate that the simulated medicament delivery device 502 has been removed from the container 503. In other embodiments, the signal S12 can include information associated with the use of the simulated medicament delivery device 502 and/or the medicament delivery device 504. For example, in some embodiments, the signal S12 can be associated with an identification of the simulated medicament delivery device 502, an identification of certain components of the simulated medicament delivery device 502 and/or a status of the simulated medicament delivery device 502, as described above. In this manner, the first electronic circuit system 570A can receive the signal S12 and produce the electronic output OP11 to include information contained within the signal S12. Said another way, this arrangement allows the first electronic circuit system 570A and the second electronic circuit system 570B to cooperatively output the electronic output OP11. For example, in some embodiments, the simulated medicament delivery device 502 can output a signal S12 that prompts the first electronic circuit system 570A to augment the electronic output OP12 (e.g., by displaying an output on a larger LCD screen or the like) previously output by the simulated medicament delivery device 502.

Similarly, in some embodiments, the first electronic circuit system 570A can output a signal S11 that can be received by the second electronic circuit system 570B. In some embodiments, the signal S11 can include, for example, updated use instructions that have been received by the first electronic circuit system 570A (e.g., via a wireless network). As described above, the second electronic circuit system 570B can receive the signal S11 and produce the electronic output OP12 to include information contained within the signal S1. This arrangement allows the first electronic circuit system 570A and the second electronic circuit system 570B to cooperatively to produce the electronic output OP12.

Although the first electronic circuit system 570A and the second electronic circuit system 570B are each shown and described as being configured to output at least an electronic output (e.g., OP11 and OP12, respectively) and a signal (e.g., S11 and S12, respectively), the use of separate terms is made for clarity. Accordingly, there is no distinction between signals and electronic outputs.

Although the medicament delivery device 504 is shown and described as including a label 506 containing information associated with the medicament delivery device 504 in a machine-readable format, in some embodiments, the medicament delivery device can include its own electronic circuit system. In such embodiments, the electronic circuit system of the medicament delivery device can cooperate with the first electronic circuit system 570A and/or the second electronic circuit system 570B to produce various electronic outputs, as described above.

In some embodiments the medical device 501 can include a simulated target (not shown in FIG. 48) to simulate a portion of a body for use with the simulated medicament delivery device 502. In some embodiments, the simulated target can be a skin pad that simulates a portion of a thigh or an arm. In other embodiments, the simulated target can be a strap or band that is placed around a portion of the user's body to provide a target for use with the simulated medicament delivery device 502 and/or the medicament delivery device 504. In some embodiments, a simulated target can include its own electronic circuit system. In such embodiments, for example, the simulated target can include one or more LEDs to provide a visual indication of a location for receiving a medicament, a force sensor to sense the force and/or pressure between the simulated target and the simulated medicament delivery device 502, or the like.

Figure 49:
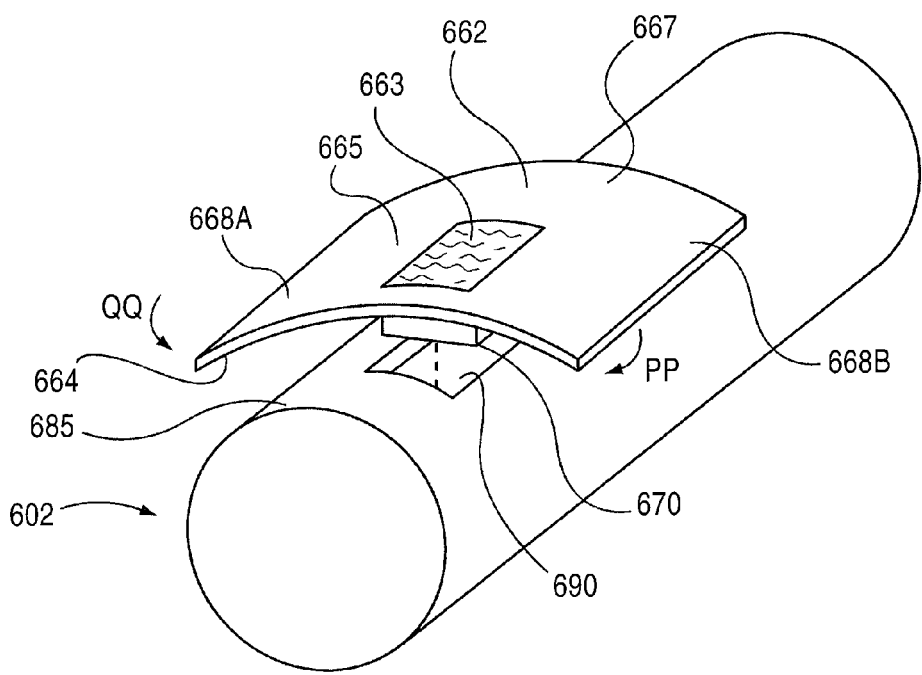
FIG. 49 is a perspective view of a simulated medicament delivery device according to an embodiment of the invention.

Although the labels are shown and described above as including a portion of an electronic circuit system and/or securing an electronic circuit system to an outer portion of a simulated medicament delivery device, in some embodiments, a label and a housing of a simulated medicament delivery device can cooperatively contain an electronic circuit system. For example, FIG. 49 is a perspective view of a simulated medicament delivery device 602 according to an embodiment of the invention. The simulated medicament delivery device 602 includes a housing 685, an electronic circuit system 670 and a label 662.

The label 662 includes a first surface 664 and a second surface 665. The first surface 664 is configured to be coupled to the housing 685 of the simulated medicament delivery device 602. In some embodiments, for example, the first surface 664 can include an adhesive to secure the label 662 to the housing 685. The second surface 665 includes an indicia 663, which can be for example, a textual indicia (e.g., a name of the device, use instructions or the like) or a symbolic indicia (e.g., an arrow pointing to a start button). Although the first surface 664 is shown as being opposite the second surface 665, in other embodiments, the first surface 664 and the second surface 665 can be adjacent each other and/or co-planar.

The label 662 also includes a rigid portion 667 disposed between two flexible portions 668A and 668B. The flexible portions 668A and 668B are configured to conform to the surface of the housing 685, as shown by the arrows PP and QQ in FIG. 49. The rigid portion 667 includes the electronic circuit system 670. The rigid portion 667 can be constructed from any suitable material, such as, for example, plastic, that can protect the electronic circuit system 670. Conversely, the flexible portions 668A and 668B can be constructed from any suitable flexible material, such as, for example, paper, flexible foam, Mylar®, Kapton® or the like. This arrangement allows the label 662 to be wrapped around the housing 685 to securely couple the electronic circuit system 670 within an opening 690 defined by the housing 685. Said another way, the label 662 and the housing 685 cooperatively define an enclosed region 690 within which at least a portion of the electronic circuit system 670 can be disposed.

Although the electronic circuit systems are shown and described above as outputting a single electronic output in response to an input (e.g., the movement of a safety lock, pressing a start button, the removal of a medicament delivery device, the change in position of a hinged lid, etc.), in some embodiments, an electronic circuit system can output a sequence of electronic outputs in response to such an input. In some embodiments, for example, when a medicament delivery device is removed from a container, an electronic circuit system disposed on the medicament delivery device and/or container can output a predetermined sequence of use instructions over a predetermined time period. For example, upon removing the medicament delivery device, the first instruction can be an audible output indicating the type of medicament delivery device removed. After a predetermined time period, the electronic circuit system can then output a second instruction, which can be a visual output instructing the user in how to diagnose the patient and/or prepare the patient for the medicament. In a similar manner, the electronic circuit system can provide additional outputs to instruct the user in the use of the medicament delivery device. Moreover, in some embodiments, the electronic circuit system can output an electronic output instructing the user in post-use procedures, such as for example, the disposal of the medicament delivery device, instructions for follow-up treatment or the like.

Although the electronic circuit systems are shown and described above as outputting recorded speech in English, in other embodiments, the electronic circuit system can output recorded speech in any language. In yet other embodiments, the electronic circuit system can output recorded speech in multiple languages. In yet other embodiments, the user can select the language in which the recorded speech is to be output.

For example, although electronic circuit systems are shown and described above as outputting one or more outputs directed towards a single, immediate user, in some embodiments, an electronic circuit system can output multiple outputs directed towards multiple different classes of users. For example, in some embodiments, an electronic circuit system can output a first electronic output to the immediate user and second electronic output to a remotely located emergency response team. In such embodiments, the second electronic output can be, for example, a phone call, a page, an e-mail or the like. For example, in some embodiments, the second electronic output can be an e-mail to the parents and/or caregivers of a child. Moreover, such a second electronic output can be transmitted either wirelessly or through a wired network.

Although the electronic circuit systems are shown and described above as outputting one or more outputs in response to one or more switches, in other embodiments an electronic circuit system can output an electronic output in response to any number of different inputs. For example, in some embodiments, an electronic circuit system can output an electronic output based on input from the user provided via a keyboard, a touch screen, a microphone or any other suitable input device. In this manner, the electronic outputs can be produced in response to direct feedback from the user.

Some embodiments of the invention relate to a computer storage product with a computer-readable medium having instructions or computer code thereon for performing various computer-implemented operations. The media and computer code may be those specially designed and constructed for the purposes of the invention, or they may be of the kind well known and available to those having skill in the computer software arts. Examples of computer-readable media include, but are not limited to: magnetic storage media such as hard disks, floppy disks, and magnetic tape; optical storage media such as Compact Disc/Digital Video Discs ("CD/DVDs"), Compact Disc-Read Only Memories ("CD-ROMs"), and holographic devices; magneto-optical storage media such as floptical disks; carrier wave signals; and hardware devices that are specially configured to store and execute program code, such as Application-Specific Integrated Circuits ("ASICs"), Programmable Logic Devices ("PLDs"), and ROM and RAM devices. Examples of computer code include, but are not limited to, micro-code or micro-instructions, machine instructions, such as produced by a compiler, and files containing higher-level instructions that are executed by a computer using an interpreter. For example, an embodiment of the invention may be implemented using Java, C++, or other object-oriented programming language and development tools. Additional examples of computer code include, but are not limited to, control signals, encrypted code, and compressed code.

Although various embodiments have been described as having particular features and/or combinations of components, other embodiments are possible having a combination of any features and/or components from any of embodiments where appropriate. For example, in some embodiments a medical device can include a container including an electronic circuit system, two or more medicament delivery devices and a movable portion. In such embodiments, each of the medicament delivery devices can be associated with a switch. Moreover, the movable portion can also be associated with a switch. In this manner, the electronic circuit system can be configured to output a first electronic output when the movable portion is moved, a second electronic output when the first medicament delivery device is removed from the container and a third electronic output when the second medicament delivery device is removed from the container.

Although the simulated medicament delivery devices and the actual medicament delivery devices are shown and described above as being separate, in some embodiments a single device can contain certain features and perform certain functions of both the a simulated medicament delivery device and an actual medicament delivery device. For example, in some embodiments, a medicament delivery device can be moved between a simulation configuration and a medicament delivery configuration. For example, in some embodiments, a simulated medicament delivery device can be configured to receive an actual medicament delivery device to subsequently move from a simulation configuration to a medicament delivery configuration.

What is claimed is:

1. An apparatus, comprising:
a simulated medicament delivery device having a housing, a removable member and a simulated actuator member;
an electronic circuit system coupled to the simulated medicament delivery device, the electronic circuit system configured to produce a plurality of electronic outputs, the electronic circuit system including a switch operably coupled to the removable member such that the removable member actuates the switch in response to the removable member being removed from the housing, the electronic circuit system configured to produce a first electronic output from the plurality of electronic outputs in response to the switch being actuated, the electronic circuit system configured to output a second electronic output from the plurality of electronic outputs in response to the simulated actuator member being manipulated, at least one of the first electronic output or the second electronic output including at least one of a visual output, an audible output or a tactile output that simulates the actuation of an actual medicament delivery device; and
a container configured to receive at least a portion of the simulated medicament delivery device, the electronic circuit system configured to produce a recorded speech output in response to the portion of the simulated medicament delivery device being removed from the container.

2. The apparatus of claim 1, wherein:
the recorded speech output is a first recorded speech output; and
the electronic circuit system is configured to produce a second recorded speech output in response to the simulated actuator member being manipulated.

3. The apparatus of claim 1, wherein:
the recorded speech output is a first recorded speech output; and
the electronic circuit system includes a visual output device, the electronic circuit system configured to produce a second recorded speech output and a visual output via the visual output device to collectively identify the removable member.

4. The apparatus of claim 1, wherein the electronic circuit system is configured to produce a plurality of recorded speech outputs in a plurality of different languages.

5. The apparatus of claim 1, wherein:
the recorded speech output is a first recorded speech output; and
the electronic circuit system includes a sensor configured to detect at least one of a position, location or orientation of the simulated medicament delivery device, the electronic circuit system configured to produce a second recorded speech output in response to an input received from the sensor.

6. The apparatus of claim 1, wherein:
the electronic circuit system is configured to produce the visual output adjacent to identify the simulated actuator member.

7. The apparatus of claim 1, wherein:
the recorded speech output is a first recorded speech output; and
the electronic circuit system includes a light output device, the first electronic output includes a light output produced via the light output device and a second recorded speech output, the light output and the second recorded speech output configured to identify a location of the simulated actuator member.

8. The apparatus of claim 1, wherein the plurality of electronic outputs is produced in a sequence determined based on input received from at least one of the switch, a sensor or a timer.

9. The apparatus of claim 1, wherein:
the electronic circuit system is configured to repeat at least one electronic output from the plurality of electronic outputs when no user interaction with the simulated medicament delivery device has been detected by the electronic circuit system within a time period after the at least one electronic output was first produced.

10. The apparatus of claim 1, wherein:
the electronic circuit system includes at least one of a position sensor, a force sensor, a pressure sensor or an optical sensor; and
the electronic circuit system is configured to output a third electronic output in response to an input received from the at least one of the position sensor, the force sensor or the optical sensor.

11. The apparatus of claim 1, wherein:
the simulated medicament delivery device further includes a label configured to be coupled to the housing of the simulated medicament delivery device; and
at least a portion of the electronic circuit system is disposed within the label.

12. The apparatus of claim 1, wherein:
the removable member container is removed from about the portion of the simulated medicament delivery device.

13. The apparatus of claim 1, wherein the removable member is a simulated needle guard disposed about an end portion of the simulated medicament delivery device, the apparatus further comprising:
a contact member coupled to the end portion of the simulated medicament delivery device such that the contact member is exposed when the simulated needle guard is removed from the end portion of the simulated medicament delivery device, the contact member configured to contact a body to simulate use of the actual medicament delivery device.

14. The apparatus of claim 1, wherein the simulated medicament delivery device is devoid of a medicament delivery mechanism such that the simulated medicament delivery device is incapable of delivering a medicament.

15. An apparatus, comprising:
a simulated medicament delivery device having a contact member coupled to an end portion of the simulated medicament delivery device, the contact member configured to contact a target location to simulate use of an actual medicament delivery device;
a removable member configured to be coupled to the end portion of the simulated medicament delivery device; and
an electronic circuit system coupled to the simulated medicament delivery device, the electronic circuit system including a visual output device on the removable member, the electronic circuit system configured to produce a visual output via the visual output device to identify the removable member in response to the electronic circuit system being actuated, the electronic circuit system includes a switch operably coupled to the contact member, the electronic circuit system configured to produce an electronic output when the switch is actuated.

16. The apparatus of claim 15, wherein:
the electronic circuit system is configured to produce a first recorded speech output to identify the removable member; and
the contact member actuates the switch in response to the contact member contacting the target location at a force greater than a predetermined force threshold, the electronic circuit system configured to produce a second recorded speech when the switch is actuated.

17. The apparatus of claim 15, wherein:
the electronic circuit system is configured to output a recorded speech output in response to the manipulation of a simulated actuator.

18. The apparatus of claim 15, wherein:
the electronic circuit system includes a sensor configured to detect at least one of a position, location or orientation of the simulated medicament delivery device, the electronic circuit system configured to produce a recorded speech output in response to an input received from the sensor.

19. The apparatus of claim 15, wherein:
the visual output is a first visual output;
the simulated medicament delivery device includes a simulated actuator configured to simulate an actuator of the actual medicament delivery device; and
the electronic circuit system is configured to produce a second visual output to collectively identify the simulated actuator.

20. The apparatus of claim 15, wherein the electronic circuit system is configured to produce a plurality of recorded speech outputs in a sequence determined based on input received from at least one of a switch, a sensor or a timer.

21. The apparatus of claim 15, wherein:
the electronic circuit system is configured to produce a recorded speech output in response to the contact member contacting the body at a force greater than a predetermined force threshold.

22. An apparatus, comprising:
a simulated medicament delivery device having a contact member coupled to a housing, the contact member configured to contact a target location to simulate a use of a corresponding medicament delivery device used to deliver a medicament to the target location;
an electronic circuit system coupled to the housing of the simulated medicament delivery device, the electronic circuit system including a switch, the electronic circuit system configured to produce a first electronic instruction in response to the switch being moved from a first state to a second state, the electronic circuit system configured to produce a second electronic instruction in response to the contact member being moved into contact with the target location; and
a removable member configured to be coupled to an end portion of the simulated medicament delivery device, the removable member having an end portion and a switch portion extending from the end portion of the removable member, the switch portion disposed within the housing and in contact with the switch of the electronic circuit system when the removable member is coupled to the end portion of the simulated medicament delivery device, the end portion of the removable member covering the contact member when the removable member is coupled to the end portion of the simulated medicament delivery device,
the switch portion configured to move the switch between the first state and the second state when the removable member is removed from the simulated medicament delivery device, the contact member being exposed when the removable member is removed from the simulated medicament delivery device.

23. The apparatus of claim 22, wherein at least one of the first electronic instruction or the second electronic instruction includes a recorded speech output.

24. The apparatus of claim 22, wherein:
the simulated medicament delivery device includes a simulated actuator configured to simulate an actuator of the corresponding medicament delivery device; and
the electronic circuit system is configured to produce a visual output via a light output device disposed adjacent the simulated actuator.

25. The apparatus of claim 22, wherein:
the simulated medicament delivery device is a simulated auto-injector;
the removable member is a simulated needle guard; and
the electronic circuit system is configured to produce a recorded speech output and a visual output to collectively identify the simulated needle guard.

26. The apparatus of claim 22, wherein the electronic circuit system is configured to produce a plurality of recorded speech outputs in a sequence determined based on input received from at least one of the switch, a sensor or a timer.

27. The apparatus of claim 22, wherein:
the electronic circuit system is configured to repeat the first electronic instruction when no user interaction with the simulated medicament delivery device has been detected by the electronic circuit system within a time period after the first electronic instruction was first produced.

28. The apparatus of claim 22, wherein at least one of the first electronic instruction or the second electronic instruction includes a signal associated with at least one of a visual output or an audible output.

29. The apparatus of claim 22, wherein:
the first electronic instruction is a recorded speech output; and
the electronic circuit system includes a visual output device disposed on the end portion of the simulated medicament delivery device, the electronic circuit system configured to produce the recorded speech output and a visual output via the visual output device to collectively identify the end portion in response to the removable member being removed from the end portion of the simulated medicament delivery device.

30. The apparatus of claim 22, wherein at least one of the first electronic instruction or the second electronic instruction includes an instruction for using at least one of the simulated medicament delivery device or the corresponding medicament delivery device.

31. The apparatus of claim 22, wherein at least one of the first electronic instruction or the second electronic instruction is associated with an orientation of the simulated medicament delivery device.

* * * * *